(12) United States Patent
Johnson et al.

(10) Patent No.: US 7,976,530 B2
(45) Date of Patent: Jul. 12, 2011

(54) INFUSION CATHETER WITH COMPOSITE TIP

(75) Inventors: Benjamin A. Johnson, Woodbury, MN (US); Matthew H. Adams, Zimmerman, MN (US); James G. Skakoon, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/799,312

(22) Filed: May 1, 2007

(65) Prior Publication Data

US 2008/0103483 A1    May 1, 2008

Related U.S. Application Data

(63) Continuation-in-part of application No. 11/589,697, filed on Oct. 30, 2006, and a continuation-in-part of application No. 11/589,694, filed on Oct. 30, 2006, now Pat. No. 7,766,394.

(51) Int. Cl.
*A61M 25/00* (2006.01)

(52) U.S. Cl. ...................................... 604/524

(58) Field of Classification Search .................. 604/524, 604/527
See application file for complete search history.

(56) References Cited

U.S. PATENT DOCUMENTS

| | | |
|---|---|---|
| 3,181,895 A | 5/1965 | Cator |
| 3,766,915 A | 10/1973 | Rychlik |
| 4,306,566 A | 12/1981 | Sinko |
| 4,328,813 A | 5/1982 | Ray |
| 4,350,159 A | 9/1982 | Gouda |
| 4,917,670 A | 4/1990 | Hurley et al. |
| 5,078,702 A | 1/1992 | Pomeranz |
| 5,092,848 A * | 3/1992 | deCiutiis .................. 604/170.01 |
| 5,092,850 A | 3/1992 | Buma |
| 5,104,705 A | 4/1992 | Quackenbush |
| 5,135,554 A | 8/1992 | Rogers, Jr. et al. |
| 5,231,996 A | 8/1993 | Bardy et al. |
| 5,254,107 A * | 10/1993 | Soltesz .......................... 604/525 |

(Continued)

FOREIGN PATENT DOCUMENTS

DE    3900635 A1 *  7/1990

(Continued)

OTHER PUBLICATIONS

"Cable Design Options and Capabilities" datasheet [online]. Polymicro Technologies, LLC, Phoenix, Arizona, 2006 [retrieved on Aug. 15, 2007]. Retrieved from the Internet:<URL:http://www.polymicro.com/catalog/4_8.htm>; 2 pgs.

(Continued)

*Primary Examiner* — Kevin C Sirmons
*Assistant Examiner* — Andrew M Gilbert
(74) *Attorney, Agent, or Firm* — Mueting, Raasch & Gebhardt, P.A.

(57) ABSTRACT

A catheter for use with a medical infusion or other fluid system. The catheter may include a flexible elongate tubular core that is resistant to radial collapse, and a separate tubular tip member forming the catheter distal tip. The catheter may further include a flexible, e.g., elastomeric, jacket that surrounds at least a portion of the tubular core. The jacket may have a radial compliance that is greater than that of the tubular core. The jacket may further define an outer diameter that is about 4 to about 6 times greater than an outer diameter of the core.

10 Claims, 29 Drawing Sheets

U.S. PATENT DOCUMENTS

| | | | |
|---|---|---|---|
| 5,314,463 A | | 5/1994 | Camps et al. |
| 5,364,357 A | | 11/1994 | Aase |
| 5,403,311 A | * | 4/1995 | Abele et al. .................... 606/49 |
| 5,454,491 A | | 10/1995 | Liu |
| 5,464,446 A | | 11/1995 | Dreessen et al. |
| 5,478,328 A | | 12/1995 | Silverman et al. |
| 5,599,326 A | | 2/1997 | Carter |
| 5,630,806 A | | 5/1997 | Inagaki et al. |
| 5,683,370 A | * | 11/1997 | Luther et al. .................. 604/528 |
| 5,720,720 A | | 2/1998 | Laske et al. |
| 5,762,637 A | * | 6/1998 | Berg et al. ..................... 604/264 |
| 5,820,610 A | | 10/1998 | Baudino et al. |
| 5,851,203 A | | 12/1998 | van Muiden |
| 5,913,848 A | | 6/1999 | Luther et al. |
| 5,927,277 A | | 7/1999 | Baudino et al. |
| 5,957,910 A | * | 9/1999 | Holden et al. ................. 604/527 |
| 6,042,578 A | | 3/2000 | Dinh et al. |
| 6,090,099 A | * | 7/2000 | Samson et al. ................ 604/527 |
| 6,093,180 A | | 7/2000 | Elsberry |
| 6,171,295 B1 | | 1/2001 | Garabedian et al. |
| 6,171,297 B1 | * | 1/2001 | Pedersen et al. .............. 604/527 |
| 6,290,692 B1 | | 9/2001 | Klima et al. |
| 6,315,757 B1 | | 11/2001 | Chee et al. |
| 6,368,301 B1 | * | 4/2002 | Hamilton et al. ............. 604/103 |
| 6,488,655 B1 | | 12/2002 | Wantink et al. |
| 6,503,353 B1 | | 1/2003 | Peterson et al. |
| 6,508,789 B1 | | 1/2003 | Sinnott et al. |
| 6,508,804 B2 | | 1/2003 | Sarge et al. |
| 6,508,805 B1 | | 1/2003 | Garabedian et al. |
| 6,648,874 B2 | * | 11/2003 | Parisi et al. ................... 604/525 |
| 6,676,643 B2 | | 1/2004 | Brushey |
| 6,821,446 B2 | | 11/2004 | Harada et al. |
| 6,827,693 B2 | | 12/2004 | White et al. |
| 6,855,124 B1 | * | 2/2005 | Gonzalez et al. .......... 604/96.01 |
| 6,863,662 B2 | | 3/2005 | Luther |
| 6,866,660 B2 | | 3/2005 | Garabedian et al. |
| 6,893,429 B2 | | 5/2005 | Petersen |
| 6,902,207 B2 | | 6/2005 | Lickliter |
| 6,945,969 B1 | | 9/2005 | Morris et al. |
| 6,991,626 B2 | | 1/2006 | Wantink et al. |
| 7,641,638 B2 | * | 1/2010 | Waxman et al. .............. 604/264 |
| 2002/0052610 A1 | | 5/2002 | Skakoon et al. |
| 2002/0095124 A1 | | 7/2002 | Palasis et al. |
| 2003/0153879 A1 | * | 8/2003 | Luther .......................... 604/272 |
| 2003/0199831 A1 | | 10/2003 | Morris et al. |
| 2003/0199852 A1 | | 10/2003 | Seward et al. |
| 2004/0044329 A1 | | 3/2004 | Trudell |
| 2004/0087933 A1 | | 5/2004 | Lee et al. |
| 2005/0043714 A1 | * | 2/2005 | Zhou ............................. 604/527 |
| 2005/0137519 A1 | | 6/2005 | Boismier |
| 2005/0182388 A1 | | 8/2005 | Garabedian et al. |
| 2005/0228361 A1 | | 10/2005 | Tremaglio et al. |
| 2006/0127158 A1 | | 6/2006 | Olson et al. |
| 2006/0129126 A1 | | 6/2006 | Kaplitt et al. |
| 2006/0135945 A1 | | 6/2006 | Bankiewicz et al. |
| 2006/0142732 A1 | * | 6/2006 | Karmarkar et al. ........... 604/508 |
| 2007/0276340 A1 | | 11/2007 | Poston et al. |
| 2009/0143764 A1 | | 6/2009 | Nelson |

FOREIGN PATENT DOCUMENTS

| | | |
|---|---|---|
| EP | 0 086 338 A1 | 8/1983 |
| EP | 0 678 302 B1 | 2/1999 |
| GB | 747453 | 4/1956 |
| JP | 2201157 | 8/1990 |
| JP | 2005323658 | 11/2005 |
| WO | WO 97/40879 | 11/1997 |
| WO | WO 02/083228 A2 | 10/2002 |
| WO | WO 03/002170 A2 | 1/2003 |
| WO | WO 03/002170 A3 | 3/2003 |
| WO | WO 03/020353 A1 | 3/2003 |
| WO | WO 02/083228 A3 | 4/2003 |
| WO | WO 03/090835 A1 | 11/2003 |
| WO | WO 2005/030316 A1 | 4/2005 |
| WO | WO 2007/024841 A2 | 3/2007 |

OTHER PUBLICATIONS

"Coatings and Buffers" datasheet [online]. Polymicro Technologies, LLC, Phoenix, Arizona, 2006 [retrieved on Feb. 20, 2007]. Retrieved from the Internet:<URL:http://www.polymicro.com/catalog/2_23.htm>; 1 pg.

"Flexible Fused Silica Capillary Tubing" datasheet [online]. Polymicro Technologies, LLC, Phoenix, Arizona, 2006 [retrieved on Feb. 20, 2007]. Retrieved from the Internet:<URL:http://www.polymicro.com/products/capillarytubing/products_capillarytubing_tsp_tsg_tsu.htm>; 2 pgs.

"Guide to Cables and Connectors" datasheet [online]. Cables Unlimited, Bohemia, New York, 2006 [retrieved on Aug. 29, 2007]. Retrieved from the Internet:<URL:http://www.connectworld.net/syscon/1stanfrm.htm>; 6 pgs.

"Introduction to Fiber Optics" datasheet [online]. Communications Specialties, Inc., Hauppauge, New York [retrieved on Aug. 29, 2007]. Retrieved from the Internet:<URL:http://www.commspecial.com/fiberguide-print.htm>; 7 pgs.

Michigan Community Blood Centers, Grand Rapids, Michigan, Memo to the Food and Drug Administration Docket Office, Aug. 16, 2002. Retrieved from the Internet:<URL:http://www.fda.gov/OHRMS/DOCKETS/dailys/02/Aug02/082702/800231db.pdf>; 3 pgs.

"MiniMed Paradigm® 515 or 715 Insulin Pump" datasheet [online]. Medtronic MiniMed, Inc., Northridge, CA, 2007 [retrieved on Aug. 31, 2007]. Retrieved from the Internet:<URL:http://www.minimed.com/products/otherpumps/515-715/>; 2 pgs.

"Optical Fiber: Definition and Much More from Answers.com" [online]. [Retrieved on Aug. 29, 2007]. Retrieved from the Internet:<URL:http://www.answers.com/topic/optical-fiber?cat=technology>; 14 pgs.

Sanftner et al., "AAV2-mediated gene delivery to monkey putamen: Evaluation of an infusion device and delivery parameters" *Experimental Neurology*, 2005; 194:476-483.

"What is Capillary" datasheet [online]. Polymicro Technologies, LLC, Phoenix, Arizona, 2006 [retrieved on Sep. 11, 2007]. Retrieved from the Internet:<URL:http://www.polymicro.com/catalog/3_1.htm>; 1 pg.

U.S. Appl. No. 11/589,694, filed Oct. 30, 2006, Sage et al.
U.S. Appl. No. 11/589,697, filed Oct. 30, 2006, Adams et al.
U.S. Appl. No. 11/799,179, filed May 1, 2007, Skakoon.
U.S. Appl. No. 11/799,319, filed May 1, 2007, Johnson et al.

"Flexible Fused Silica Capillary Tubing" datasheet [online]. Polymicro Technologies, LLC, Phoenix, AZ, page available Mar. 12, 2005 [retrieved on Mar. 12, 2009]. Retrieved from the Internet:<URL:http://web.archive.org/web/20050312103226/http://www.polymicro.com/products/capillarytubing/products_capillarytubing_tsp_tsg_tsu.htm>; 2 pgs (URL and document provided by USPTO on PTO-892 dated Mar. 25, 2009 in U.S. Appl. No. 11/799,319).

Krauze et al., "Reflux-free cannula for convection-enhanced high-speed delivery of therapeutic agents," *J. Neurosurg.*, Nov. 2005, 103:923-929.

Krauze et al., "Real-time imaging and quantification of brain delivery of liposomes," *Pharm. Res.*, Nov. 2006, 23(11):2493-2504. Published online Sep. 14, 2006.

"Thick Wall Flexible Fused Silica Capillary Tubing" datasheet [online]. Polymicro Technologies, LLC, Phoenix, AZ, page available Oct. 18, 2005 [retrieved on Mar. 12, 2009]. Retrieved from the Internet:<URL:http://web.archive.org/web/20051018182636/http://www.polymicro.com/products/capillarytubing/products_capillarytubing_tsp.htm>; 2 pgs (URL and document provided by USPTO on PTO-892 dated Mar. 25, 2009 in U.S. Appl. No. 11/799,319).

* cited by examiner

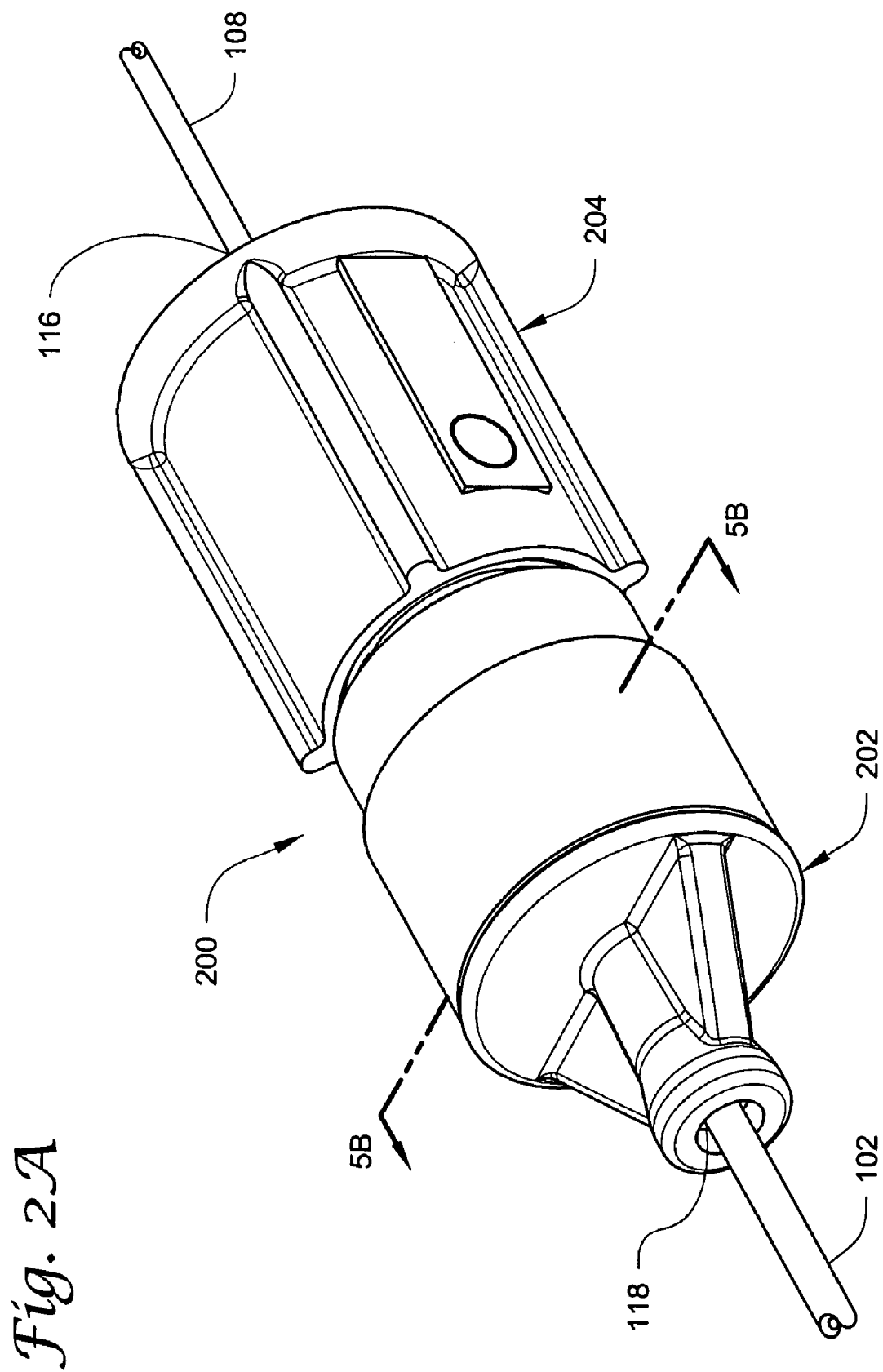

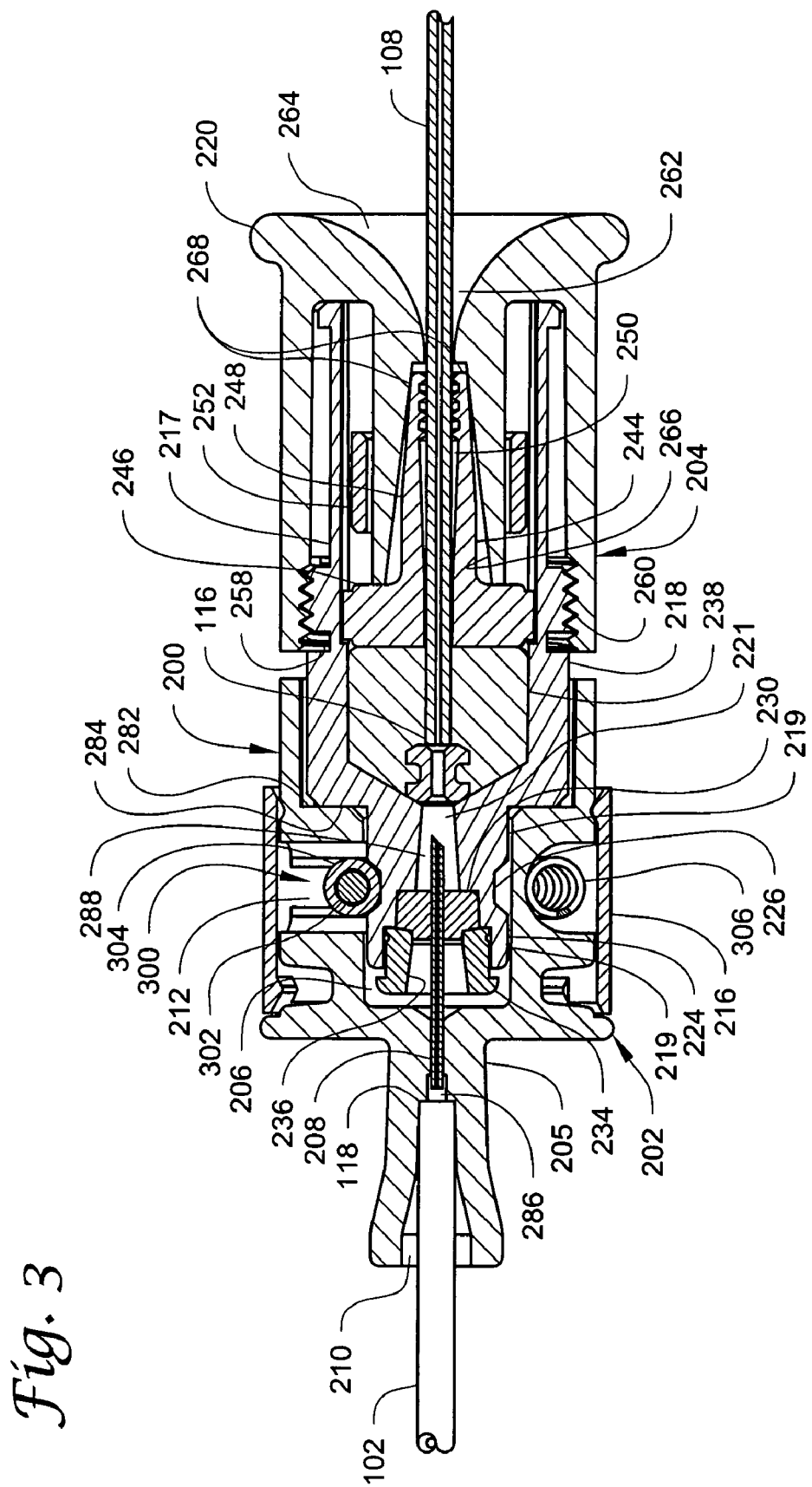

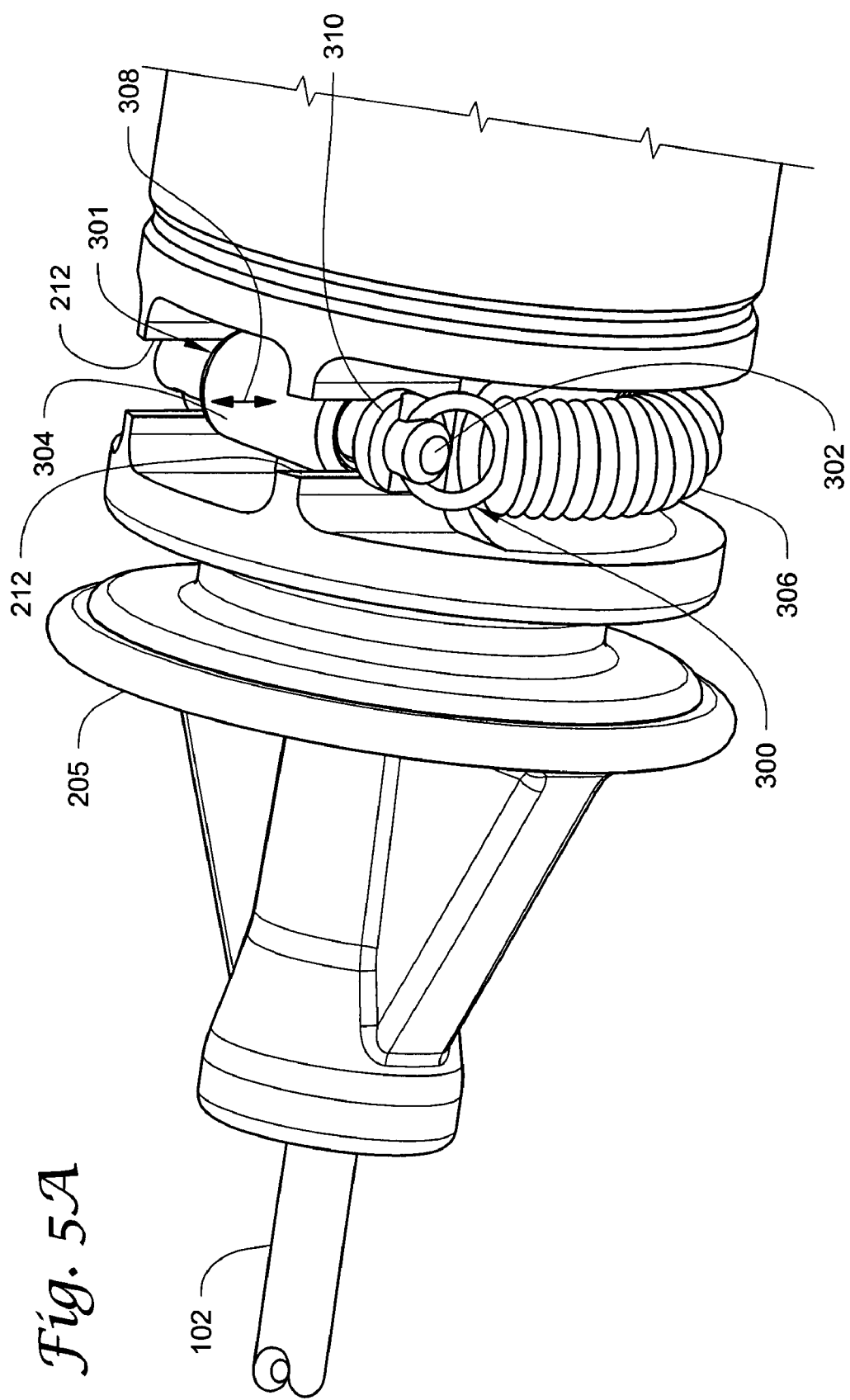

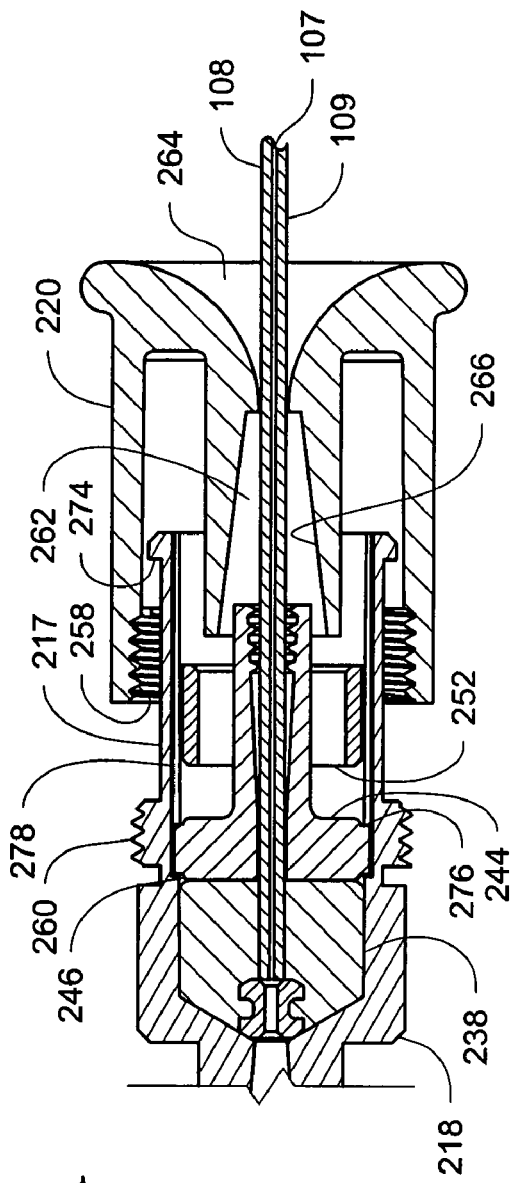
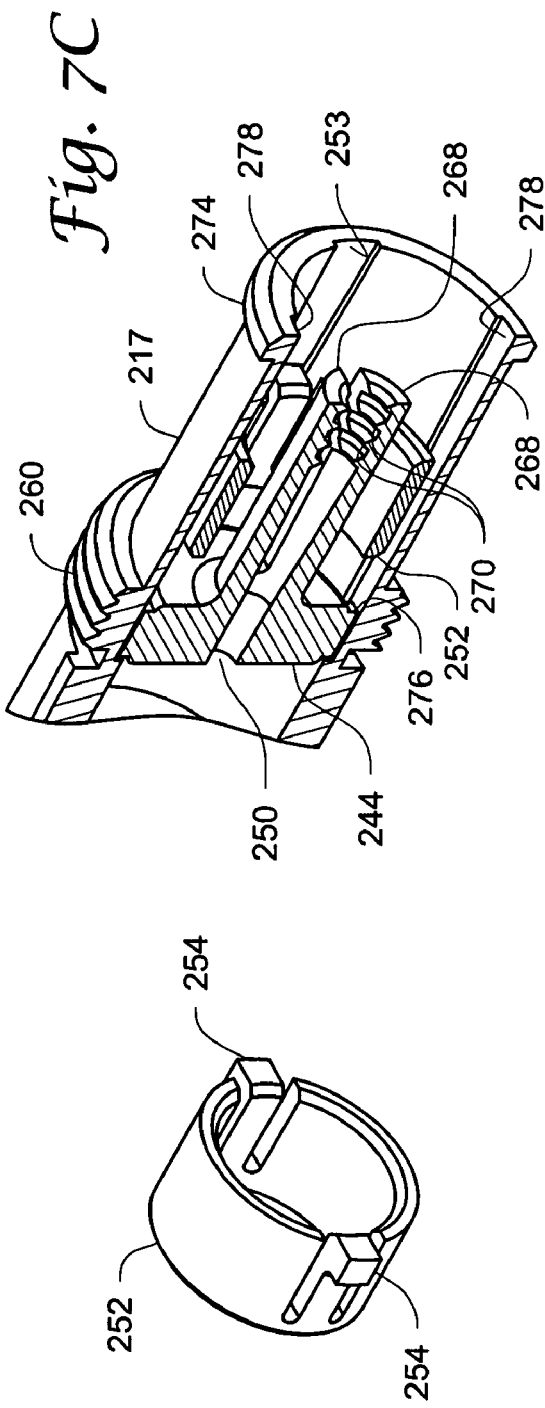
Fig. 7A
Fig. 7B
Fig. 7C

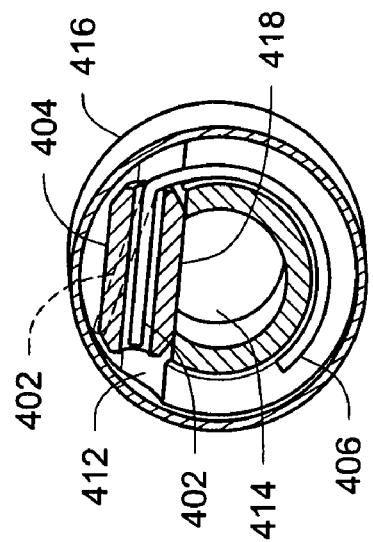
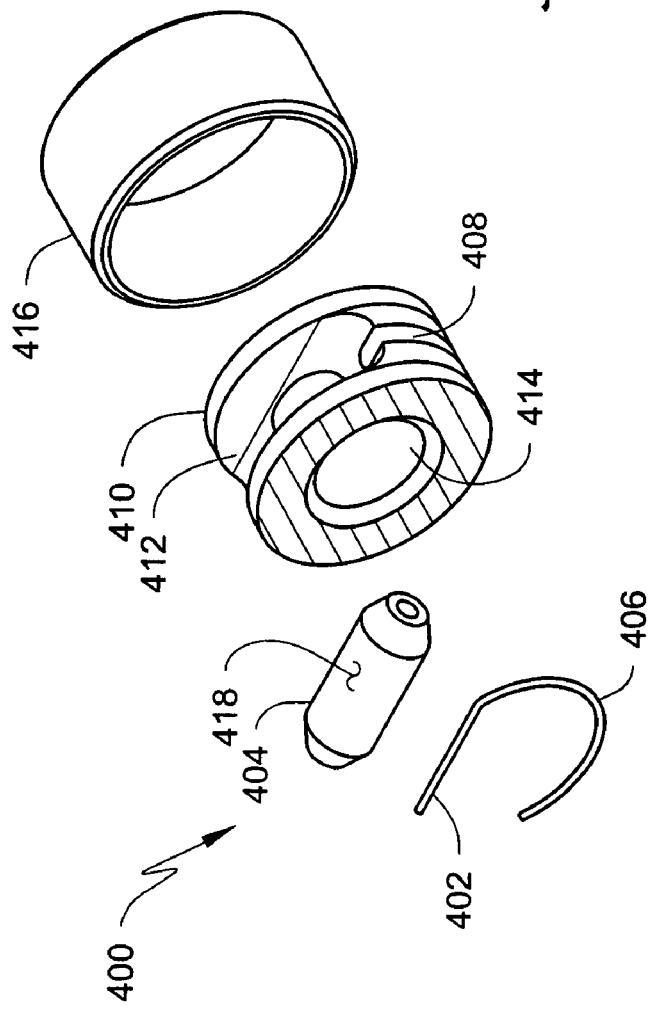

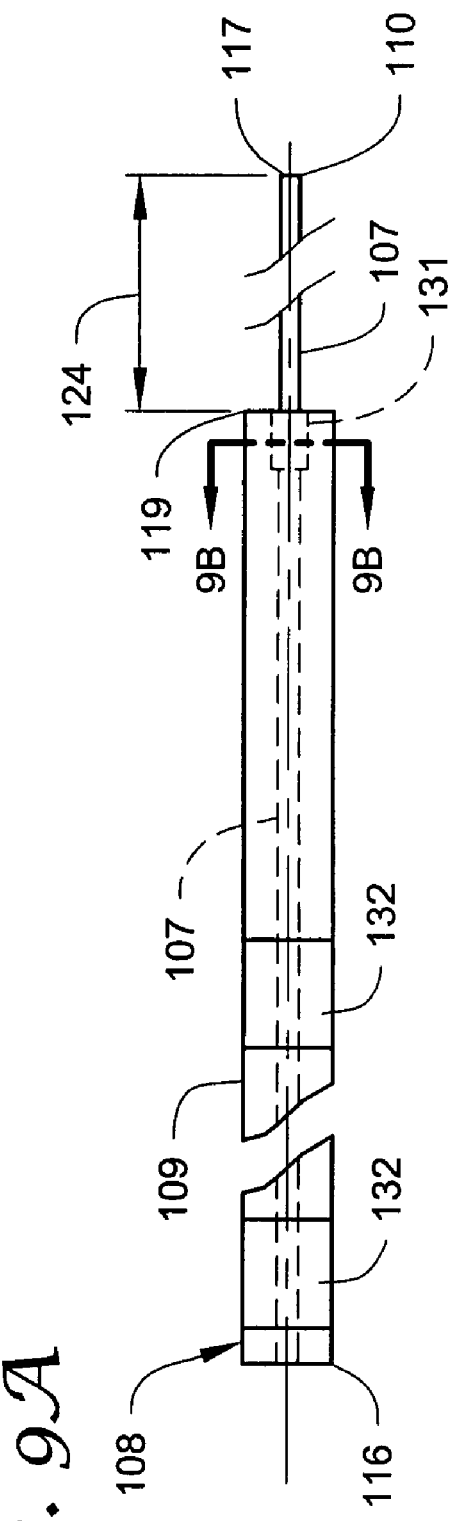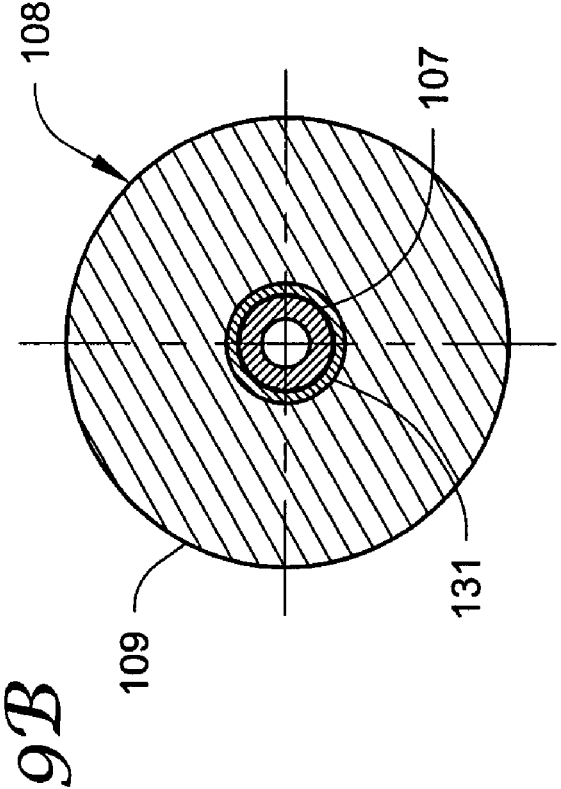
Fig. 9A
Fig. 9B

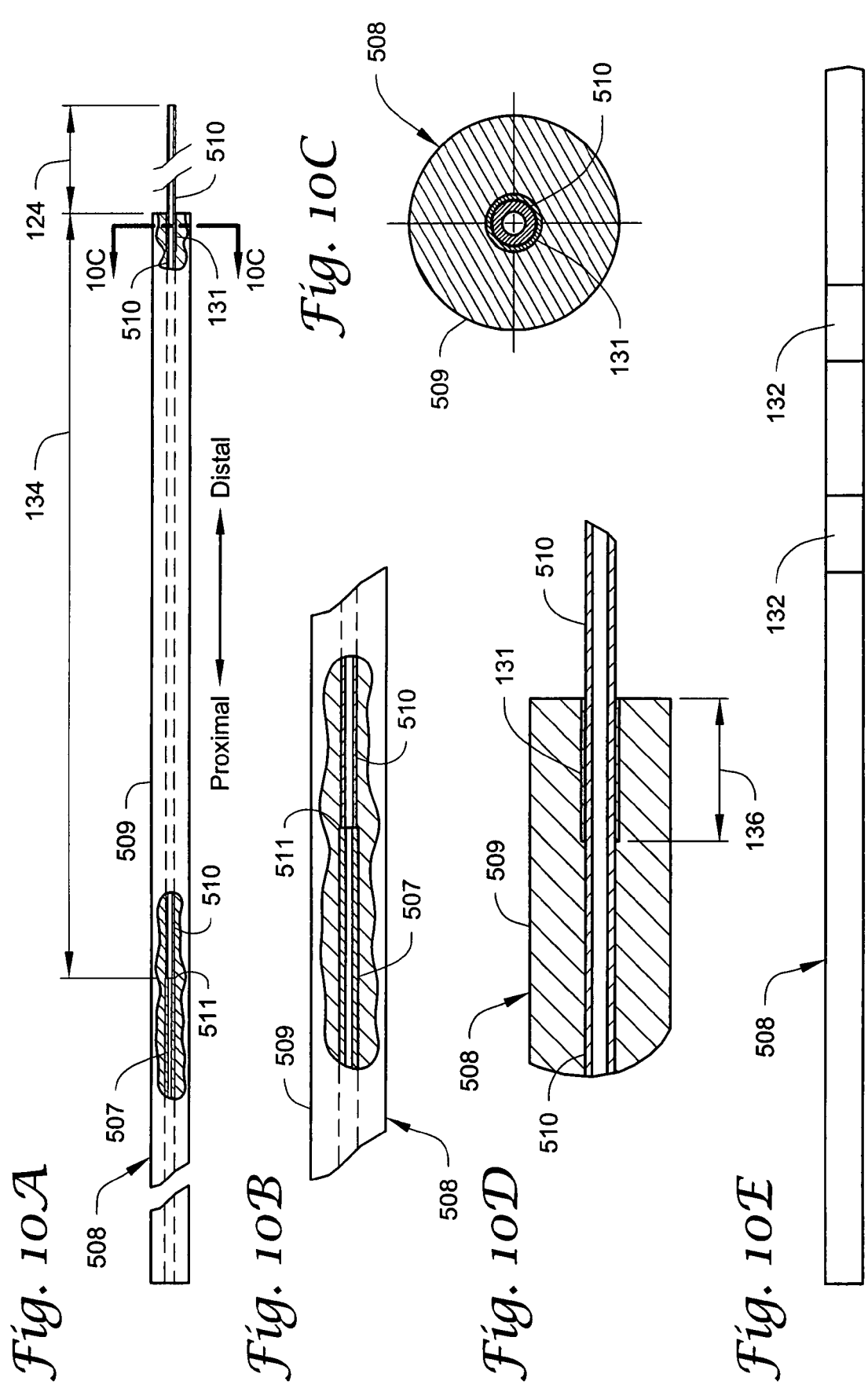

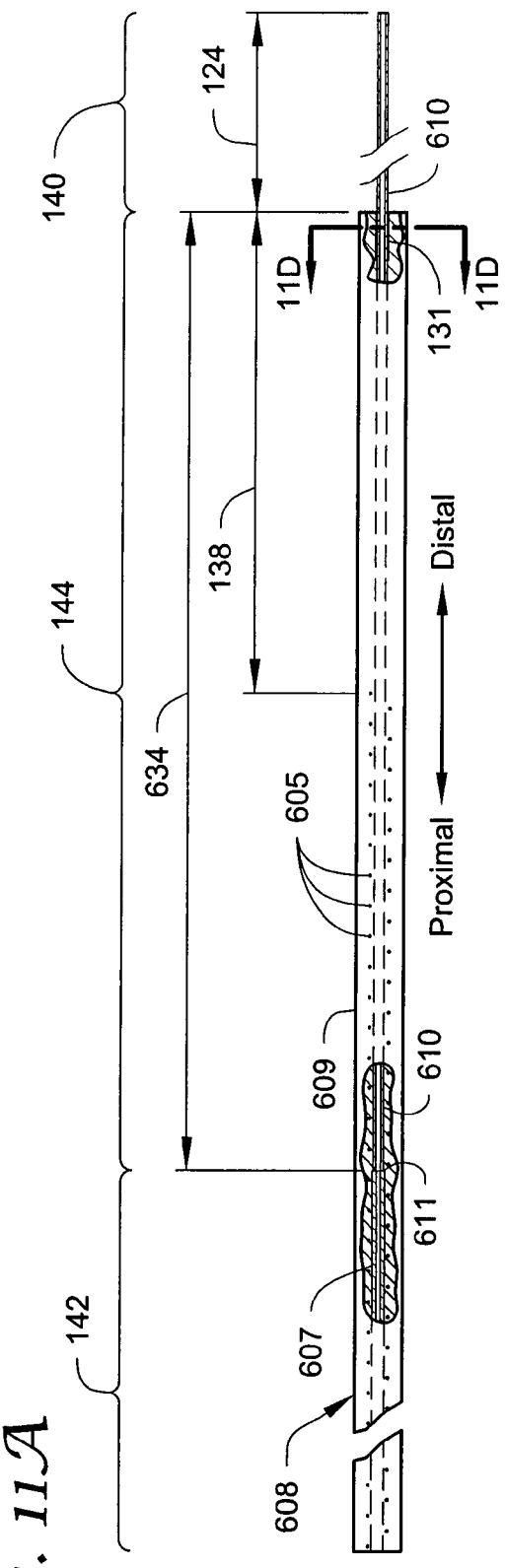
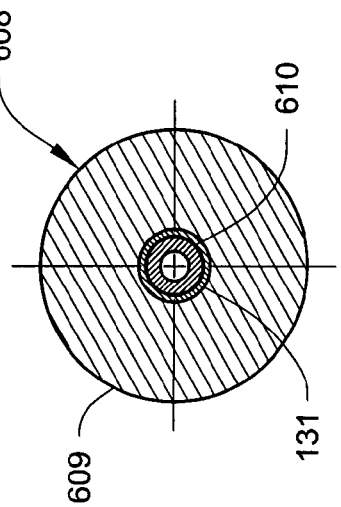
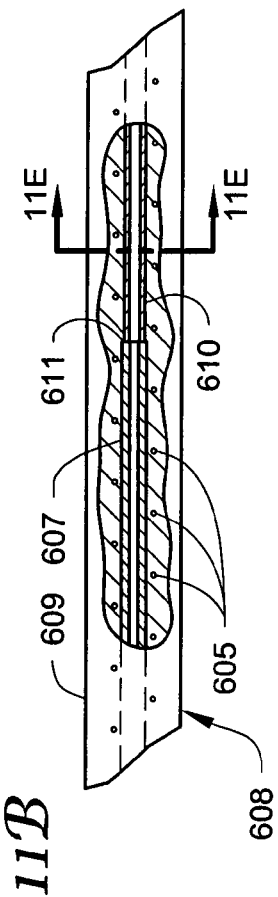

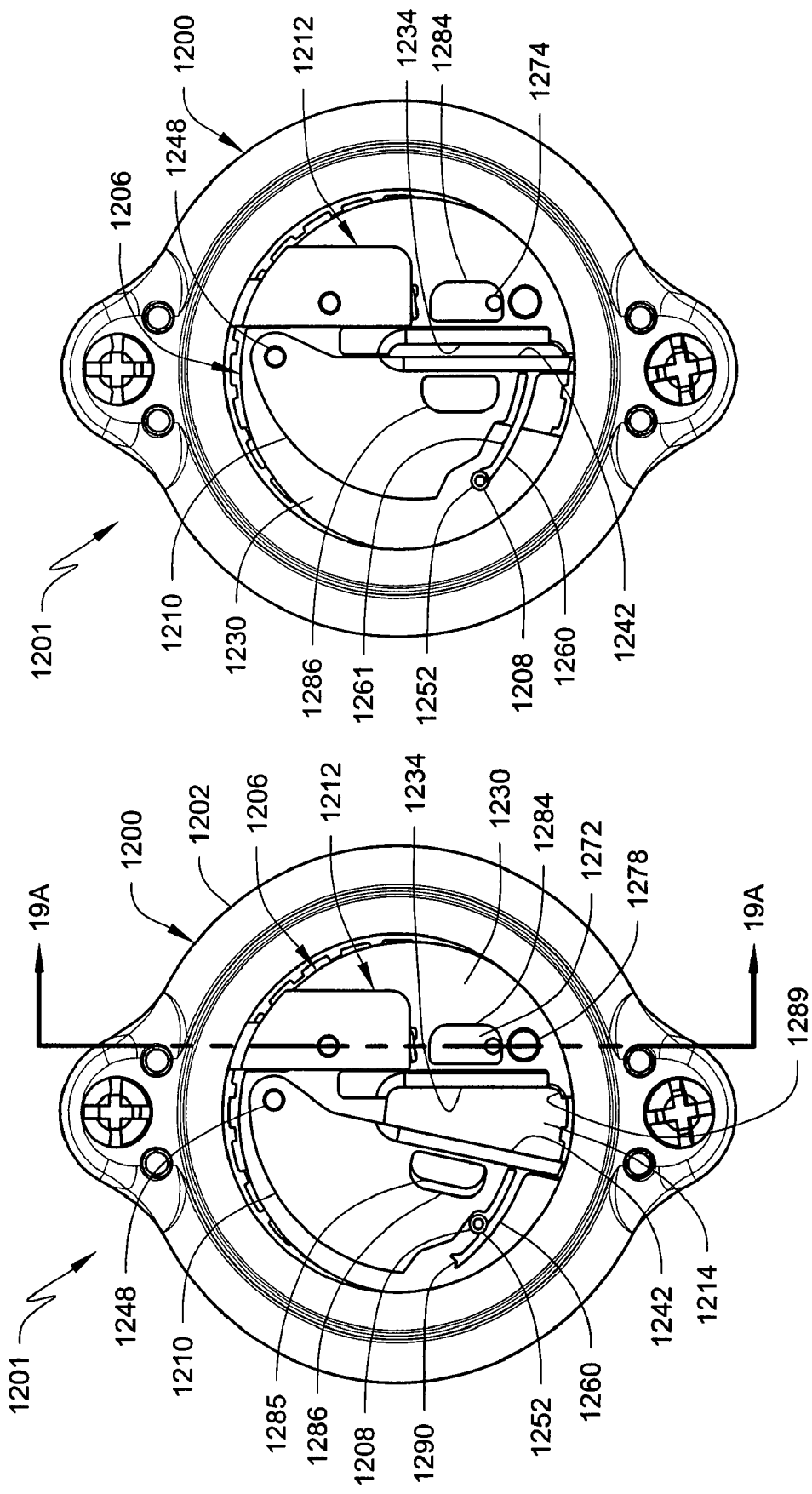

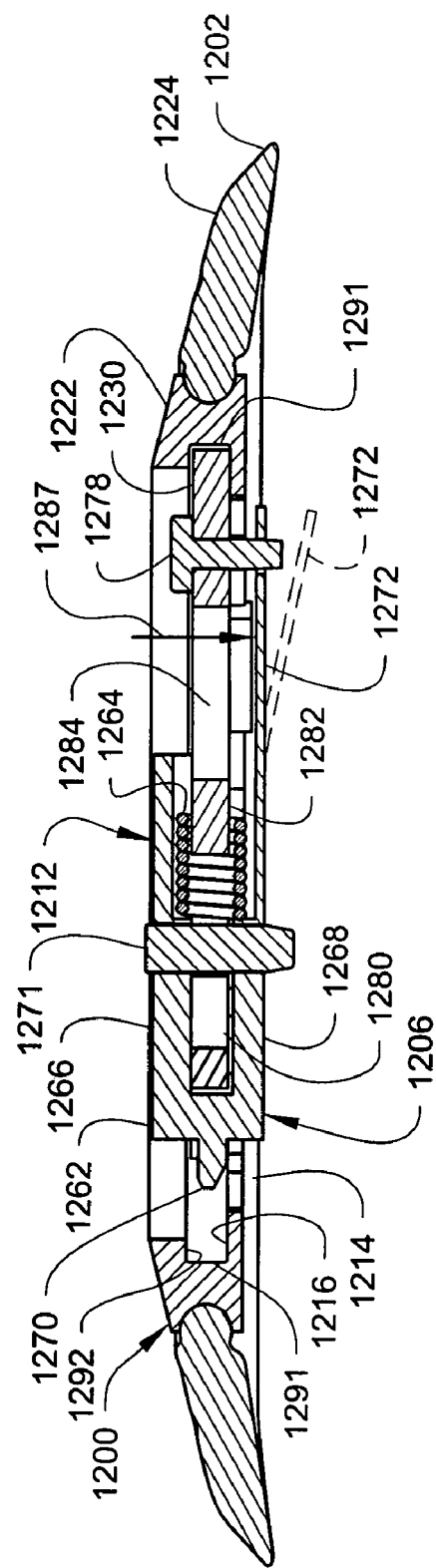
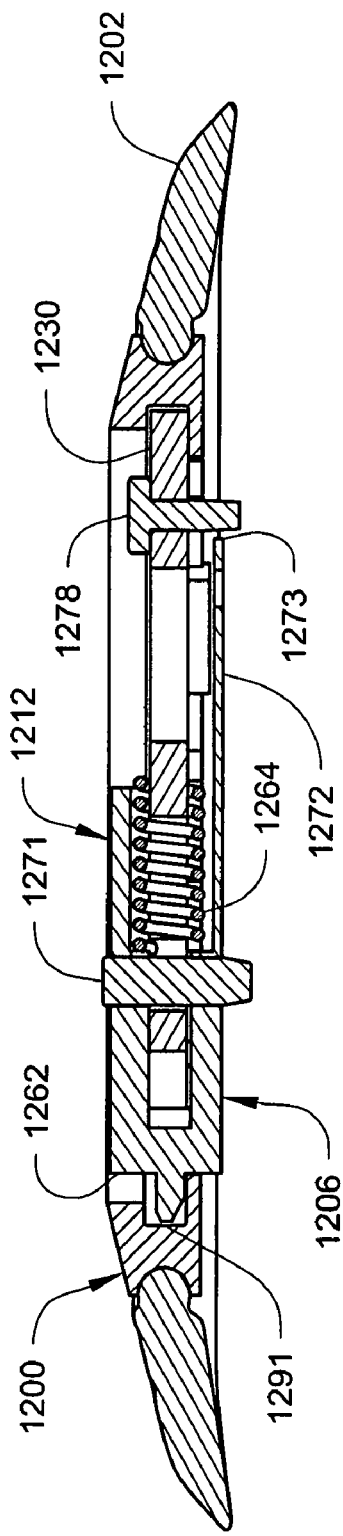
Fig. 19A
Fig. 19B

INFUSION CATHETER WITH COMPOSITE TIP

RELATED APPLICATIONS

The present application is a continuation-in-part of U.S. patent application Ser. No. 11/589,694, filed Oct. 30, 2006, now U.S. Pat. No. 7,766,394, and is also a continuation-in-part of U.S. patent application Ser. No. 11/589,697, also filed Oct. 30, 2006, both of which are incorporated herein by reference in their respective entireties.

TECHNICAL FIELD

The present invention relates generally to medical devices and, more particularly, to catheters, portal anchors, catheter connectors, and systems for delivering a therapeutic agent to a region of a body such as the brain.

BACKGROUND

Medical procedures involving the delivery or removal of fluids from the body often utilize a catheter system for fluid transport. The catheter system may include a flexible tube or catheter that operatively enters the body, and an externally located fluid reservoir. One example of a removal catheter system is a urinary catheter for use with patients that may have difficulty urinating.

Other catheter systems are capable of delivering a fluid, e.g., a therapeutic agent, to the body. For example, the use of intracerebroventricular or parenchymal catheters is known for infusing therapeutic agents to a specific location within the brain to treat a variety of disorders including, for example, chronic pain and movement disorders. In an illustrative example, an incision is made in a patient's scalp to expose the skull through which a burr hole may then be formed. The catheter may then be inserted through the burr hole and anchored in place, e.g., with a burr hole anchor. Surgeons may often use stereotactic apparatus/procedures to position catheters and other brain instruments (e.g., electrical stimulation leads). For example, U.S. Pat. No. 4,350,159 to Gouda illustrates an exemplary stereotactic instrument used to position an electrode.

As one can appreciate, once an inserted device such as a catheter is properly positioned, it is important that it be adequately immobilized to prevent movement from its intended location. Even minimal movement of the device tip may yield unsatisfactory therapeutic results. Accordingly, reliable methods and apparatus for anchoring and securing the device relative to the burr hole are needed. To secure the catheter relative to the burr hole, burr hole anchor devices, including devices similar to those described in U.S. Pat. No. 4,328,813 to Ray and U.S. Pat. No. 5,927,277 to Baudino et al., may be used.

Many of these anchor devices are used primarily to secure a catheter or lead for long term implantation. Some therapies (e.g., acute gene therapy for the treatment of Parkinson's disease, chemotherapy), however, may be delivered during a more limited period of time, e.g., a few hours to a few days or less. In the case of the latter, it may be beneficial to completely remove the delivery catheter at therapy completion. Device (e.g., catheter) removal, though, generally requires a surgical procedure to: expose the burr hole and anchor; release the catheter from the anchor; remove the catheter; and close the incision. While effective, such a removal procedure may be undesirable for various reasons, including, for example, cost and potential patient apprehension associated with the surgical removal procedure.

The portion of the catheter extending beyond the skull may be tunneled beneath the skin (e.g., to connect to an implanted reservoir or pump) or, alternatively, routed outside the body where it may connect, typically via a longer secondary tube, to an external source containing the therapeutic agent.

While fully implanted systems may be beneficial for long term treatment of certain chronic ailments, external routing may be preferable for shorter term therapies (e.g., those lasting a few days or less). Current external routing configurations may, however, present issues not necessarily present with internal systems. For example, the externalized components may benefit from various attachment and strain relief techniques to minimize movement of the implanted catheter that might result from exposure to inadvertent, external forces. Moreover, in the event of a catheter break, the externalized catheter system may require component replacement and/or additional sterilization procedures in order to reduce potential contamination. While such attachment techniques and sterilization procedures are effective, it may be beneficial if the need for such additional measures could be reduced or eliminated.

Short term therapies may further benefit from catheters that are of an advantageous size (e.g., diameter) for the particular therapy delivery profile. For example, many conventional catheters are of a diameter that is unnecessarily large for shorter term, low volume therapy delivery. However, conventional catheters having a small diameter may be subject to inadvertent occlusion as a result of anchoring or twisting of the catheter.

SUMMARY

Catheters, anchors, connectors, and systems in accordance with embodiments of the present invention may overcome these and other issues. For instance, in one embodiment, an implantable catheter is provided for delivering a therapeutic agent to a body. The catheter includes an elongate tubular core comprising a first material, the core having a distal end and a proximal end. The catheter further includes an elongate tubular tip comprising a second material, the tip also having a distal end and a proximal end. The proximal end of the tip is positioned to abut or be near the distal end of the core such that a generally continuous lumen extends from the proximal end of the core to the distal end of the tip. The catheter also includes an elastomeric jacket surrounding longitudinal portions of both the tip and the core, wherein the distal end of the tip protrudes beyond a distal end of the elastomeric jacket.

In another embodiment, an implantable catheter for delivering a therapeutic agent to a body is provided, wherein the catheter includes a distal end section, a proximal end section, and a medial section between the distal and proximal end sections. The distal end section includes a longitudinal portion having a uniform outer diameter less than an outer diameter of both the proximal end section and medial section. Moreover, the distal end section has a bending stiffness that is greater than a bending stiffness of at least the proximal end section.

In yet another embodiment, an implantable catheter for delivering a therapeutic agent to a body is provided. The catheter includes an elongate tubular tip member comprising stainless steel tubing; and an elongate tubular core member comprising polyetheretherketone (PEEK) tubing. The core member further includes a distal end positioned generally in abutting contact with a proximal end of the tubular tip member such that a continuous lumen extends from a proximal end of the tubular core member to a distal end of the tubular tip member. The catheter also includes an elastomeric jacket comprising polyurethane surrounding longitudinal sections of both the tubular tip member and the tubular core member.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 1A-1B illustrate an exemplary system, e.g., infusion system, including a connector (e.g., breakaway connector), infusion catheter, and portal anchor in accordance with one embodiment of the invention, wherein: FIG. 1A is a diagrammatic view of the system implanted in a human body; and FIG. 1B is a view of the system removed from the body;

FIGS. 2A-2B illustrate enlarged perspective views of the exemplary connector of FIGS. 1A-1B, wherein: FIG. 2A is an enlarged perspective view of the connector; and FIG. 2B is an exploded perspective view illustrating how a modified connector may be attached to a headgear apparatus;

FIG. 3 is a section view of the connector of FIG. 2A, taken through a plane containing a longitudinal axis of the connector, illustrating both a first coupler and a second coupler;

FIGS. 5A-5B illustrate an exemplary retention device, e.g., a roller assembly, for use with the connector of FIG. 2A, wherein: FIG. 5A is an enlarged perspective view of the roller assembly; and FIG. 5B is a section view taken along line 5B-5B of FIG. 2A;

FIGS. 7A-7C illustrate various aspects of the first coupler of FIG. 2A, wherein: FIG. 7A is a section view of the first coupler in a partially assembled state, the view taken through a plane containing a longitudinal axis of the first coupler; FIG. 7B is a perspective view of a stop member of the first coupler; and FIG. 7C is a partial perspective section view of a portion of the first coupler;

FIGS. 8A-8B illustrate a retention device in accordance with another embodiment of the invention, wherein: FIG. 8A is an exploded partial perspective view; and FIG. 8B is a perspective section view;

FIGS. 9A-9B illustrate a catheter in accordance with one embodiment of the invention, wherein FIG. 9A illustrates a side elevation view; and FIG. 9B illustrates a section view taken along line 9B-9B of FIG. 9A;

FIGS. 10A-10E illustrate a catheter in accordance with another embodiment of the invention, wherein FIG. 10A illustrates a breakaway side elevation view; FIG. 10B illustrates an enlarged breakaway view of a portion of the catheter; FIG. 10C illustrates a section view taken along line 10C-10C of FIG. 10A; FIG. 10D illustrates an enlarged section view of a distal end portion of the catheter; and FIG. 10E is a side elevation view;

FIGS. 11A-11E illustrate a catheter in accordance with another embodiment of the invention, wherein FIG. 11A illustrates a breakaway side elevation view; FIG. 11B illustrates an enlarged breakaway view of a first portion of the catheter; FIG. 11C illustrates an enlarged breakaway view of a second portion of the catheter; FIG. 11D is a section view taken along line 11D-11D of FIG. 11A; and FIG. 11E is section view taken along line 11E-11E of FIG. 11B;

FIG. 17 is a top plan view of the anchor assembly of FIG. 15 with the arm shown in the unlocked position, but with the latch shown in the latched position;

FIG. 18 is a top plan view of the anchor assembly of FIG. 16 with the arm shown in the locked position and the latch shown in the latched position;

FIGS. 19A-19B illustrate section views of the anchor assembly of FIG. 17, wherein: FIG. 19A is a section view taken along line 19A-19A of FIG. 17 but with the latch of the retainer shown in the unlatched position; and FIG. 19B is a section view similar to that of FIG. 19A, but with the latch of the retainer shown in the latched position;

FIGS. 21A-21D illustrate an exemplary method for using the anchor assembly of FIGS. 1A-1B, wherein: FIG. 21A illustrates attachment of the anchor base to the skull; FIG. 21B illustrates insertion of the anchor retainer into the anchor base; FIG. 21C illustrates external portions of the anchor assembly and catheter after an implantation incision is closed; and FIG. 21D illustrates unlocking and removal of the catheter at therapy completion;

FIGS. 22A-22B illustrate an anchor assembly in accordance with an alternative embodiment of the invention, wherein: FIG. 22A is a perspective view of the anchor assembly during assembly of an anchor retainer with an anchor base; and FIG. 22B illustrates the anchor assembly after assembly and with the retainer shown in a first or unlocked configuration corresponding to an arm of the retainer being in a first or unlocked position;

FIGS. 24A-24B illustrate an optional cap for use with the anchor assembly of FIGS. 22A-22B, wherein: FIG. 24A is a bottom perspective view prior to attachment of the cap; and FIG. 24B is a top perspective view after attachment of the cap; and FIGS. 25A-25D illustrate an anchor assembly in accordance with yet another embodiment of the invention, wherein: FIG. 25A is a perspective view of the anchor assembly during attachment of an anchor retainer with an anchor base; FIG. 25B illustrates immobilization of the catheter; FIG. 25C illustrates release of the catheter, e.g., at therapy completion; and FIG. 25D illustrates a bottom perspective view of the anchor retainer of FIGS. 25A-25C.

Figure 1A:
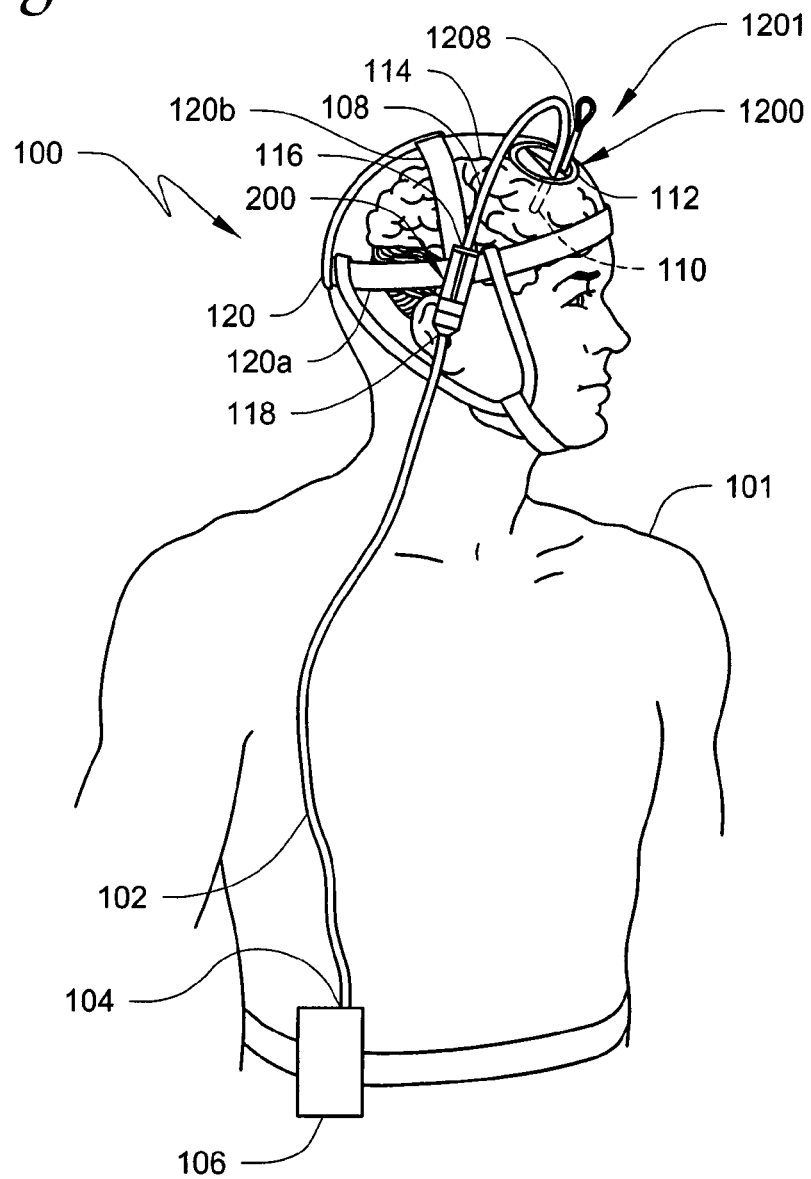

The figures are rendered primarily for clarity and, as a result, are not necessarily drawn to scale.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the invention.

Embodiments of the present invention are directed generally to fluid coupling devices, fluid conduits, anchoring devices, and to systems and methods incorporating the same. For example, embodiments of the invention may include: medical connectors for coupling a first tube (e.g., catheter) to a second tube; corresponding tubes and catheters; and body portal anchors for securing therapy delivery devices (such as tubes/catheters) relative to a body portal. Other embodiments of the invention may be directed to implantable medical systems, e.g., infusion systems (incorporating one or more of these components), for infusing a therapeutic agent into a body.

Figure 1B:
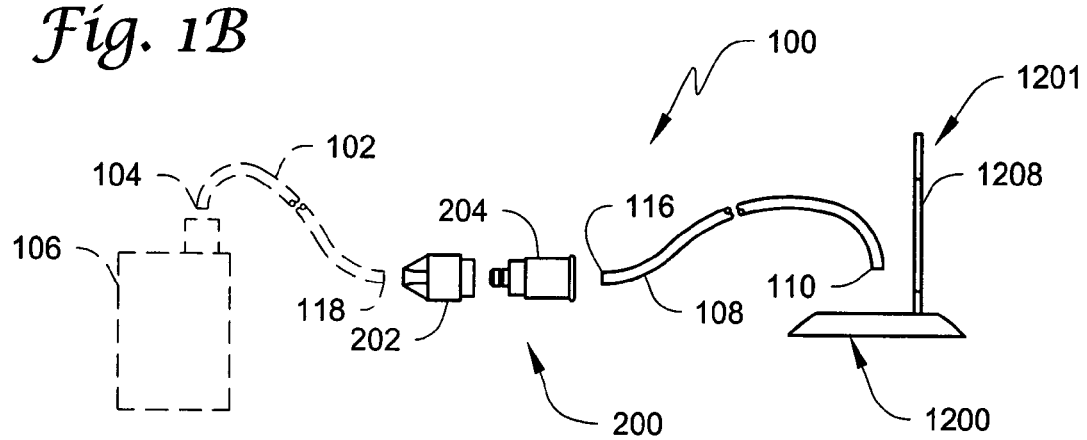

FIGS. 1A and 1B illustrate an exemplary implantable medical system (e.g., a brain infusion catheter system 100) in accordance with one embodiment of the invention. FIG. 1A illustrates the system as it may be configured during use, e.g., implantation, while FIG. 1B illustrates the system removed from the body.

The exemplary infusion system may include a first medical tube, e.g., brain catheter 108, and a second medical tube, e.g., secondary tube 102. The tube 102 may have its distal end 104 coupled to a reservoir (e.g., infusion pump 106, which may be identical or similar in construction to insulin pumps such as the Paradigm 515 or 715 pumps produced by Medtronic MiniMed of Northridge, Calif., USA) containing a volume of a therapeutic agent. Similarly, the brain catheter 108 may have its distal end 110 implanted within the body 101 (as used herein, the terms "distal" and "proximal" are taken from the reference of a connector 200 as shown in FIG. 1). In the illustrated example, the catheter 108 has its distal end 110 implanted, via a burr hole 112, at a predetermined location within a brain 114 of the patient. A burr hole anchor 1200 may be used to secure the catheter 108 relative to the burr hole 112. The anchor 1200 may form part of an anchor assembly 1201 that may also include a lock member 1208 described in more detail elsewhere herein. A proximal end 116 of the catheter 108 may extend outside the body 101 and connect to a corresponding proximal end 118 of the tube 102, e.g., via the connector 200.

While described herein in the context of a pump 106, this configuration is not limiting. For example, other embodiments may replace the pump with most any medicament delivery device, e.g., syringe, drip bag, etc., without departing from the scope of the invention.

The system 100 may, in one embodiment, be configured to deliver a therapeutic agent containing a virally mediated gene therapy as an acute treatment for Parkinson's disease. The therapeutic agent is delivered, via the tube 102 and catheter 108, from the pump 106 to the brain 114. This application is not limiting, however, as the system may be configured to deliver most any therapeutic agent (e.g., chemotherapy) to most any area of the body without departing from the scope of the invention.

It is noted that the terms "comprises" and variations thereof do not have a limiting meaning where these terms appear in the accompanying description and claims. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

With this general overview, the following description will address various embodiments of the system 100 and its components, and methods for making and using the same. While these embodiments may be described with some degree of specificity, they are nonetheless intended to be exemplary. Those of skill in the art will recognize that other embodiments are possible without departing from the scope of the invention.

It is further noted that the following description is organized by headings and subheadings for organizational purposes only. Accordingly, the particular headings/subheadings are not intended to limit in any way the embodiments described therein, i.e., alternative embodiments of a component presented under one heading or subheading of the specification may be found elsewhere (e.g., under another heading) in the specification. As a result, the specification is intended to be considered in its entirety.

Connectors

One aspect of the present invention is directed generally to fluid coupling devices and, in particular, to medical connectors such as connector 200 shown in FIGS. 1A and 1B, systems, and to methods for coupling a first tube (e.g., catheter) to a second tube or other medical device. In the illustrated embodiment, the connector is shown as part of the catheter, e.g., infusion, system 100 having the partially implanted catheter 108 and the external infusion pump 106. However, this configuration is not limiting as embodiments of the connectors, connector systems, and other aspects of the present invention may find use in other catheter applications, as well as in other medical and non-medical fluid systems.

Connectors in accordance with embodiments of the present invention may be configured to separate or de-couple once a threshold traction force is applied across the connector (e.g., applied to the two tubes 102, 108 joined by the connector). As a result, the connector provides a "breakaway" function in the event of exposure to inadvertent forces. Preferably, two couplers of the connector engage one another via a low friction (e.g., substantially frictionless) retention device. In the embodiments described and illustrated herein, the connector may also maintain a closed fluid path, in the event of connector breakaway, to protect the implanted catheter from contamination.

An enlarged view of the exemplary connector 200 is illustrated in FIG. 2A. The connector 200 may include a second connector portion or coupler 202 attached to the secondary tube 102 and a first connector portion or coupler 204 attached to the brain catheter 108 as further described below (see also FIG. 1B). In the illustrated embodiment, the first coupler 204 may be supported by an optional headgear apparatus 120 (see FIG. 1A), which may hold the connector 200, e.g., via a connection with the first coupler, during implantation. While illustrated as supported by a headgear apparatus 120 in FIG. 1A, the connector 200 could alternatively be generally unsupported, e.g., supported only by the free proximal ends 116 and 118 of the catheter 108 and tube 102, respectively, without departing from the scope of the invention.

As further illustrated in FIG. 1A, the catheter 108 may be supported at the body by the body portal anchor, e.g., burr hole anchor 1200. Exemplary burr hole anchors are described in more detail below and in related U.S. patent application Ser. No. 11/589,697, filed on Oct. 30, 2006.

Figure 2B:
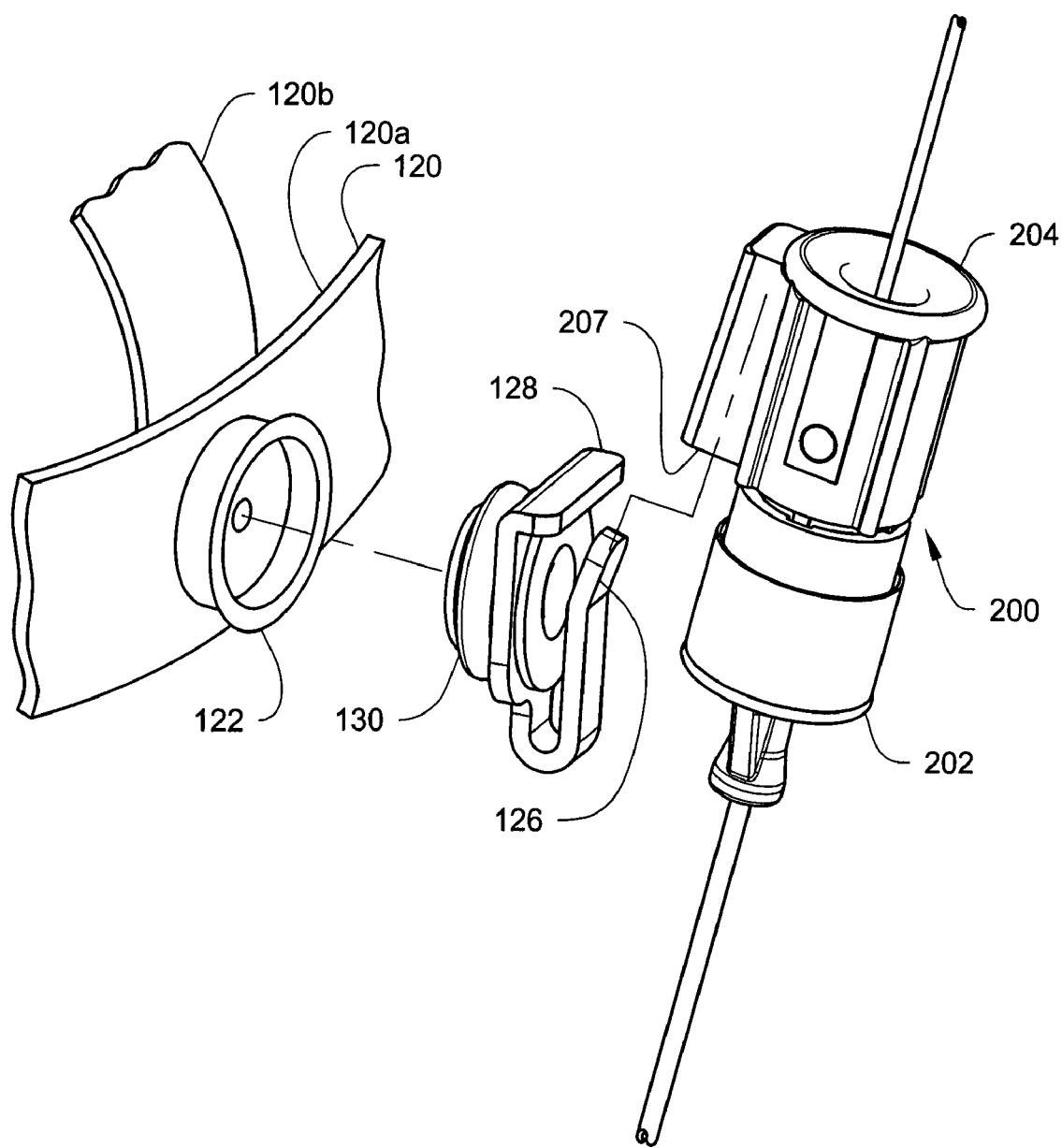

FIG. 2B illustrates one exemplary embodiment for attaching the connector 200 to the headgear apparatus 120. The headgear apparatus may be formed from a series of adjustable, fabric (e.g., nylon webbing) or elastic bands (only two bands 120a and 120b are illustrated in FIG. 2B). The bands may surround the head of the patient, as shown in FIG. 1A, sufficiently to reduce or even prevent the headgear apparatus 120 from substantial movement relative to the patient's head. On one or more sides, the headgear apparatus 120 may have attached thereto (e.g., riveted) a circular snap fit receptacle 122 that, in one embodiment, is similar or identical to the female portion of a conventional metallic garment snap button.

The first coupler 204 of the connector 200 may optionally include an integrally formed (or otherwise attached) bracket that forms a receiving slot 207 (shown only in FIG. 2B) along one side. The receiving slot 207 may be configured to receive a tab 126 of a clip 128. Once the tab 126 is fully inserted into the slot 207, the clip 128 may be generally attached to the connector 200 until the components are intentionally disassembled. The clip may also include a male member 130 that is receivable by the snap fit receptacle 122 (the male member 130 may be similar or identical in construction to a male portion of the conventional garment snap button). Once the clip is attached to the receptacle 122, the clip (and thus the connector 200) may pivot generally about an axis of the receptacle, e.g., providing some degree of stress relief to the catheter 108.

Figure 4:
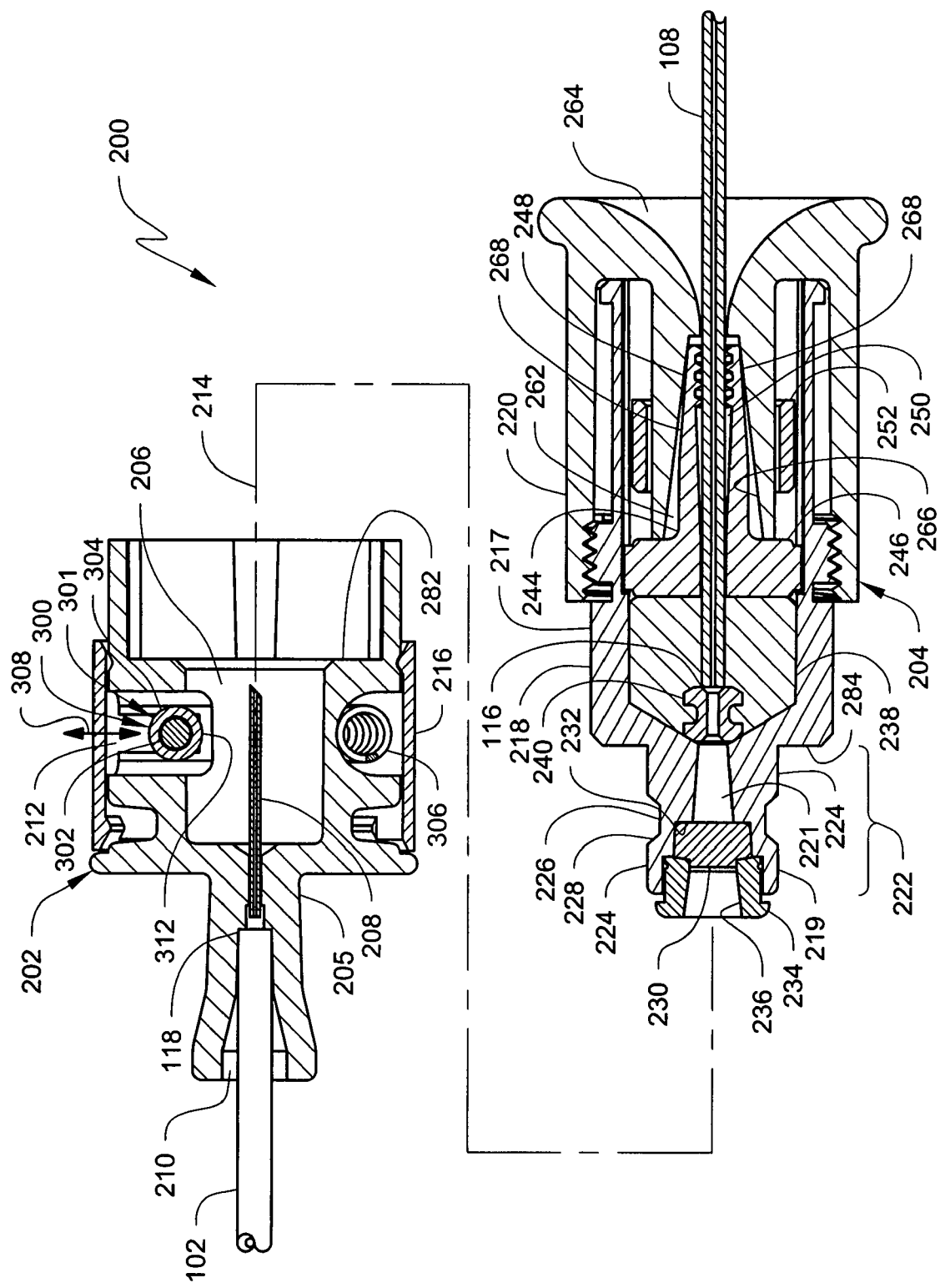
FIG. 4 illustrates the section of the connector shown in FIG. 3 with the first coupler shown separated from the second coupler.

FIG. 3 is a cross sectional view of the connector 200 of FIG. 2A (taken through a plane containing a longitudinal axis of the connector) with the couplers 202 and 204 connected. FIG. 4, on the other hand, is a similar section view with the couplers detached. Each of the couplers 202 and 204 is described separately below with reference to these figures.

The second coupler 202 may form a tubular body 205 defining a bore 206. The body 205 may be made from various materials including, for example, polyetheretherketone (PEEK), polycarbonate, and similar materials. A hollow needle 208 may be attached to the body 205 and extend into the bore 206 as illustrated. The needle 208 may define a lumen or passageway in fluid communication with the tube 102. The needle 208 may be affixed to the body 205 via any acceptable technique including, for example, by adhesive.

The body 205 also defines a smaller secondary bore 210 configured to receive the tube 102. The tube 102 may attach to the second coupler in a manner similar to the needle 208, e.g., with adhesive. When assembled as illustrated in FIGS. 3 and 4, fluid may travel from the source (e.g., pump 106 of FIGS. 1A-1B) through a lumen of the tube 102 and through the hollow needle 208.

The connector 200 may further include a retention device, e.g., biased retention device 300, which, in the illustrated embodiment, is attached to, or otherwise associated with, the second coupler 202. The retention device 300, further illustrated in FIGS. 5A and 5B (some structure removed for clarity in these views), may include a roller assembly 301 having an axle 302 and a cylindrical roller 304 rotatable about the axle. A tension member, e.g., spring 306, may also be included and attached to opposite first and second ends of the axle 302. The spring 306 may extend circumferentially about the tubular body 205 of the second coupler 202 as shown.

The roller assembly, e.g., the cylindrical roller 304, may, in a first configuration, be positioned offset from (and preferably transverse to), an axis 214 of the first and second couplers. The axle 302 may be configured to move (e.g., translate) within slots 212 formed in the body 205 such that the axle and roller 304 are movable primarily in a radial direction 308 (see FIGS. 4, 5A, and 5B) from the axis 214 (see FIG. 4) of the couplers. The spring 306, which may be a conventional (e.g., stainless steel) extension spring, may provide a radially-biased force to the axle 302 that tends to pull the roller assembly 301 (e.g., the axle 302 and roller 304), towards the axis 214. The other components of the roller assembly, e.g., the roller 304 and the axle 302 may also be made from stainless steel or other materials as described below.

The roller assembly 301 may further include a washer or flange 310. The flange 310, which may be integrally formed with the axle 302, assists with guiding the roller assembly 301 within the slots 212 as shown in FIGS. 5A and 5B.

Figure 5B:
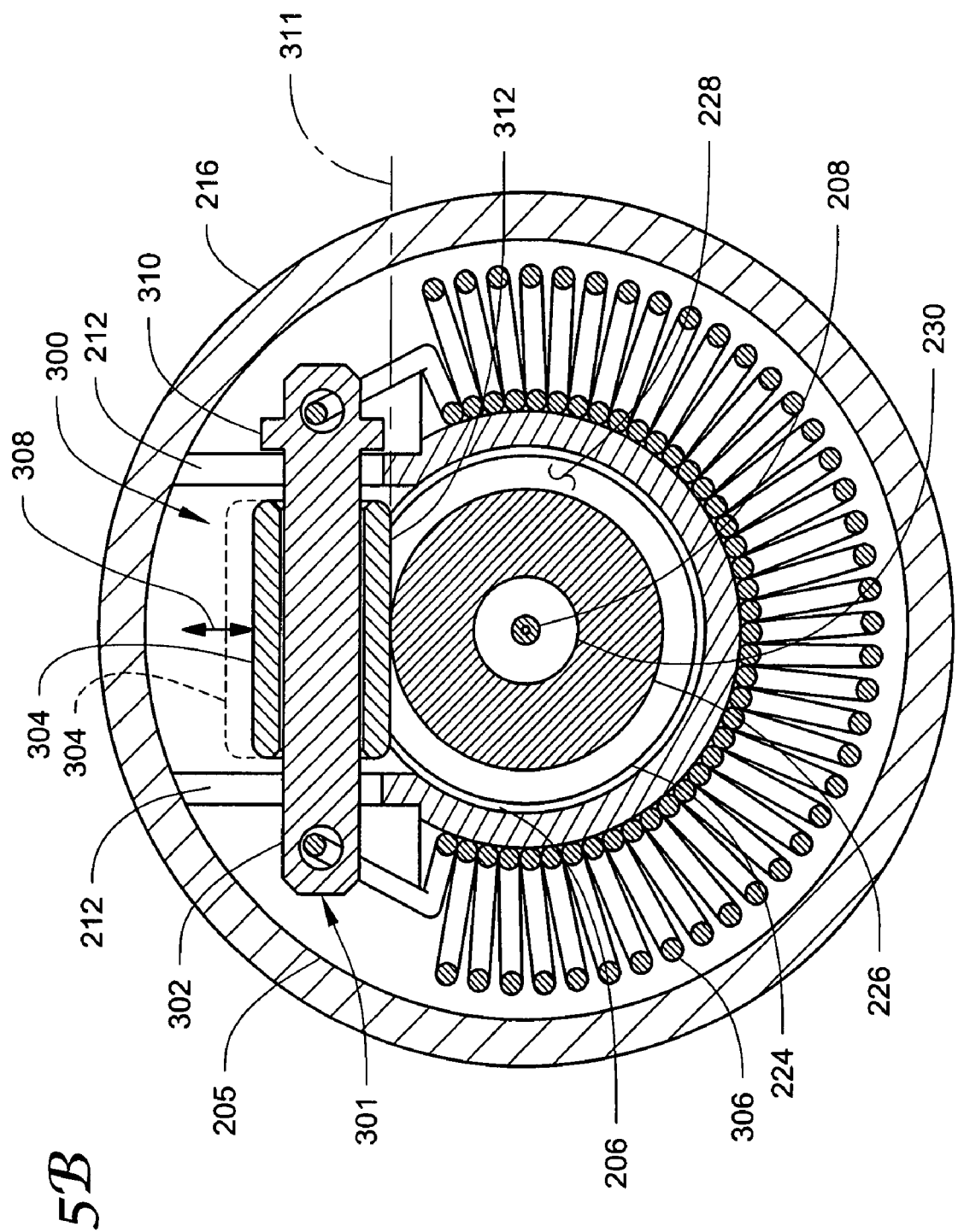

As illustrated in FIG. 5B, the roller assembly 301 of the retention device may also include a contact surface 312 (e.g., the outer surface of the roller 304). The contact surface 312 may, in the illustrated embodiment, form a secant 311 extending through the bore 206 of the tubular body 205 when the roller assembly is in the first configuration shown in solid lines in FIG. 5B (e.g., corresponding to a grooved surface 226 of the first coupler 204 (see FIG. 4) being aligned with the roller 304). As further described below, the roller assembly 301, e.g., the roller 304 and contact surface 312, may move to a second configuration (shown in broken lines in FIG. 5B), wherein the contact surface 312 is located at or outside of the bore 206. Thus, as further described below, the roller assembly 301 may be configured to selectively interlock the second coupler 202 with the first coupler 204; and release the first coupler from the second coupler when a predetermined traction force is applied between the first and second couplers.

The second coupler 202 may further include an optional sleeve 216 that covers at least a portion of the outer surface of the body 205. The sleeve 216 may reduce the potential for patient/clinician contact with portions of the retention device 300, and may further prevent foreign objects from interfering with its operation. Exemplary materials for the sleeve include polyurethane and polypropylene. The sleeve 216 may include a lip (e.g., a discontinuous lip as shown in FIGS. 3 and 4) or other locating feature that permits it to snap or bias into place relative to the body 205.

The first coupler 204 is illustrated in detail in FIGS. 3, 4, 6, and 7A-7C. The first coupler may, in the illustrated embodiment, be formed by an attachment member 218 and a housing 220, both of which may be constructed from materials similar to the body 205 of the second coupler 202.

The attachment member 218 may include an engagement portion 219 receivable within the bore 206 of the second coupler 202. The attachment member 218 may also include a body portion 217 that is threadably engagable with the housing 220. In the illustrated embodiment, the attachment member 218 is, when inserted into the bore 206, coaxial with the second coupler 202.

The engagement portion 219 may include an outer surface 222 having a generally cylindrical cross section. The roller 304 of the roller assembly 301 may be configured to engage the outer surface 222 of the engagement portion 219 in rolling contact as the engagement portion moves, e.g., translates, within the bore 206 of the second coupler 202. The outer surface 222 may be formed by both an engagement surface 224 defined by a first diameter, and the grooved surface 226 (or "groove") defined by a second diameter that is less than the first diameter (see, e.g., FIG. 4). The grooved surface 226 is positioned along the engagement surface 224 so as to receive the roller assembly 301 of the retention device (e.g., the roller 304) when the first coupler 204 is fully engaged with the second coupler 202 as shown in FIG. 3. The phrases "fully engaged," "fully connected," "fully inserted," and the like are used herein to indicate that the noted components are engaged to a point where further engagement is either not possible or not necessary to the proper functioning of the connector.

The outer surface 222 may further include a ramped surface 228 extending between the grooved surface 226 to the engagement surface 224. The ramped surface 228 may act as a camming surface to permit rolling contact of the roller 304 back and forth between the engagement surface 224 and the grooved surface 226.

The attachment member 218 may form a tubular wall that defines a passageway 221 extending through the attachment member. The passageway 221 may surround or otherwise contain a needle-penetrable septum 230 in the vicinity of the engagement portion 219. The septum 230 may be made of most any material that permits selective penetration by the needle 208 and self-sealing upon needle withdrawal. While other materials are possible, the septum 230 is, in one embodiment, made of silicone.

The septum 230 may be secured within the passageway 221 in most any fashion. For example, in the illustrated embodiment, the passageway 221 may form a step surface 232 (e.g., proximate the engagement portion 219) against which the septum 230 may be located. A retaining member 234 may then be secured (e.g., via adhesive or the like) within the passageway 221 to secure the septum 230 in place. The retaining member 234 may, in one embodiment, have a tapered interior surface 236 that assists in guiding the needle 208 into the septum 230 as the first coupler 204 is connected to the second coupler 202.

The attachment member 218 may be attached to the housing 220 before use as further described below. While the particular attachment technique may vary without departing from the scope of the invention, the body portion 217 of the attachment member may, in the illustrated embodiment, include a threaded portion (e.g., male thread 260) operable to engage a corresponding threaded portion (e.g., female thread 258) of the housing 220 as shown in FIGS. 3, 4, 6, and 7A.

As evident in the figures, the body portion 217 may be of larger diameter that the engagement portion 219 to accommodate various components of the first coupler 204. For example, the body portion 217 may be sized to receive a seal 238 within the passageway 221. The seal 238 preferably includes a lumen that extends completely through the seal. The lumen of the seal may be configured to receive the proximal end 116 of the catheter 108 and form a substantially leak-free seal therewith. In one embodiment, the seal 238 may include a generally compliant body (e.g., made from silicone or similar material) configured to surround the end 116 of the catheter 108, and an optional rigid tubular member 240 positioned within the lumen, e.g., proximate one end of the compliant body. The rigid tubular member 240 may serve various purposes including, for example, preventing occlusion of the lumen of the seal 238 as the seal is compressed. Moreover, the member 240 may provide an abutting surface against which the proximal end 116 of the catheter 108 may seat during assembly of the first coupler 204.

The tubular member 240 may be made from most any material that can hold its shape as the seal 238 is compressed. Exemplary materials include polysulfone and polycarbonate. The tubular member 240 may be attached to the body of the seal (e.g., adhesive, interference fit), or it may be held in place merely by contact between the inner surface of the passageway 221 and a step surface formed in the seal body.

Figure 6:
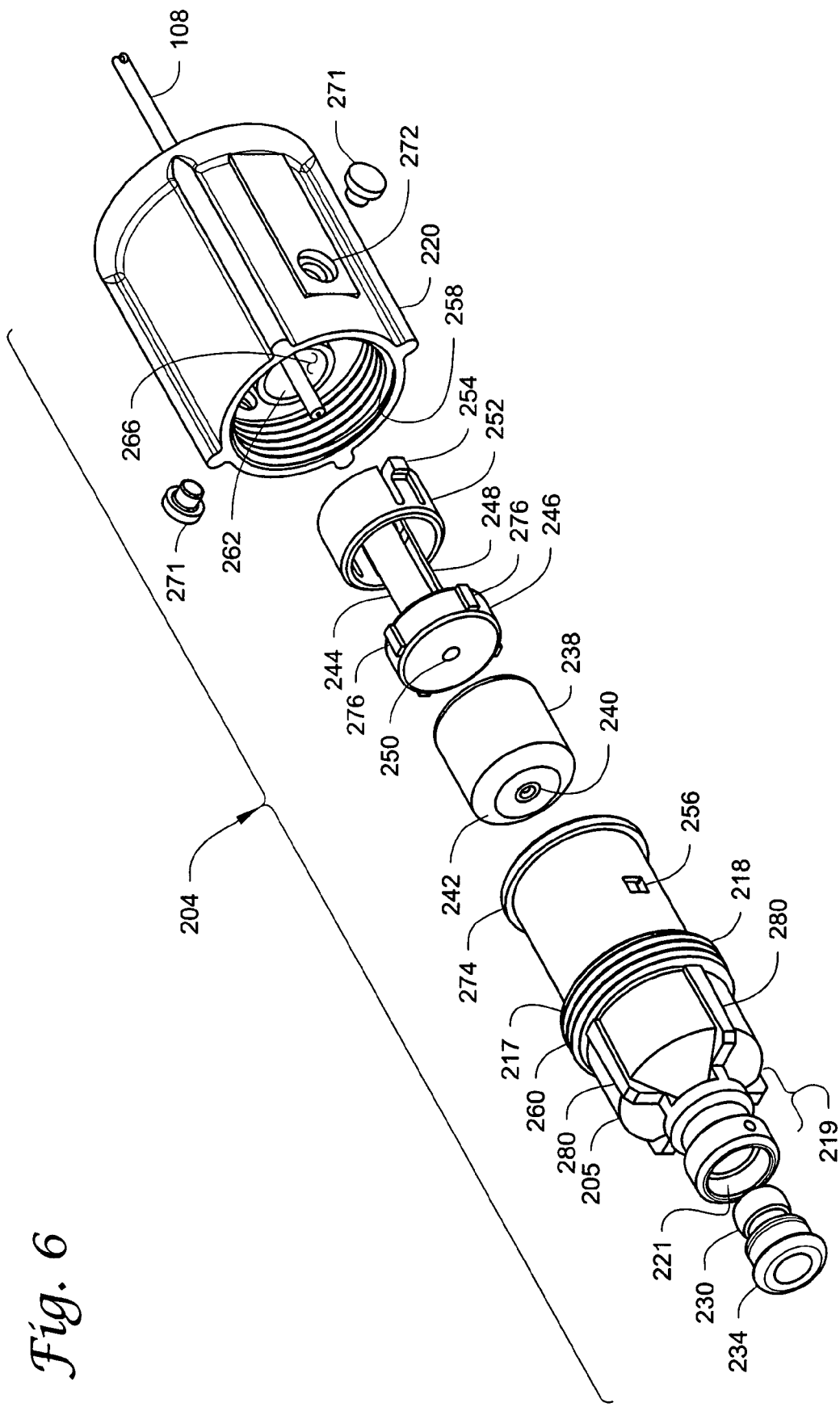
FIG. 6 is an exploded perspective view of the first coupler of the connector of FIG. 2A.

FIG. 6 provides an exploded view of the first coupler 204. As shown in this view, the seal 238 may include a tapered surface 242 to seat against a corresponding tapered surface within the passageway 221 of the attachment member 218 as shown in FIGS. 3 and 4. The first coupler 204 may also include a collet 244 located within the passageway 221 of the attachment member 218. The collet 244 is configured to, in conjunction with the housing 220, compress the seal 238 and clamp or otherwise immobilize the catheter 108. The collet 244 may include a piston 246 that abuts the seal 238, and a split rod 248 operable to receive the catheter 108 therein. The collet 244 may further include a collet passageway 250, extending through the collet (e.g., through the piston 246 and split rod 248), through which the catheter 108 may pass as shown in FIGS. 3 and 4. The collet 244 may be made from a material similar to that of the body 205.

As further described below, the collet 244 may translate within the attachment member 218. To limit the range of travel of the collet, a stop or stop member 252 may be provided. FIG. 6 illustrates that the stop member 252 may include ears 254 (only one shown) configured to engage openings 256 (only one shown) in the body portion 217 of the attachment member 218. Once the ears 254 are engaged with the openings 256, the stop member 252 generally limits travel and prevents removal of the collet 244 from the attachment member 218 (unless the stop member is first removed).

As with the other components of the first coupler 204, the housing 220 may define a passageway 262 extending completely through the component to permit passage of the catheter 108. At the outermost end of the housing 220, e.g., where the catheter exits, the passageway 262 may flare to form a bell-mouth opening 264. The large radius of the bell-mouth opening 264 may reduce strain on the catheter 108 during the implantation period.

The portion of the passageway 262 opposite the bell-mouth opening 264 may form a frusto-conical surface 266 diverging towards the piston 246 of the collet 244 as shown in FIGS. 3 and 4. The frusto-conical surface 266 is configured to contact two or more movable (e.g., deflectable) legs 268 of the split rod 248 of the collet as the housing 220 is threaded onto the attachment member 218. As the surface 266 contacts the legs 268, the legs may be directed inwardly towards the catheter 108. The legs 268 may mechanically (e.g., frictionally or via a biting or clamping action) engage the catheter 108 when the housing 220 is fully engaged with the attachment member 218 as described below. In the illustrated embodiment, the legs 268 may include protrusions 270 (see FIG. 7C) to assist with engagement of the catheter 108.

The frusto-conical surface 266 of the housing may also terminate at an abutting surface configured to contact and push against the piston 246 of the collet 244. As a result, when the housing 220 is fully engaged with, e.g., threaded onto, the attachment member 218, the collet 244 may both compress the seal 238 against an inner surface of the attachment member, and mechanically engage the catheter 108.

FIGS. 6 and 7A-7C illustrate assembly of the first coupler 204. As shown in these views, the septum 230 and retaining member 234 may be secured within the passageway 221 of the attachment member 218 as discussed above. The seal 238, collet 244, and stop member 252 may then be placed into the attachment member 218 and the stop member positioned such that the ears 254 engage the openings 256 as described above. To assist with aligning the stop member 252 with the openings 256, grooves 253 may be provided along the inside surface of the attachment member 218 as shown in FIG. 7C.

Once the seal 238 and collet 244 are positioned, the housing 220 may be placed over the attachment member 218 as shown in FIG. 7A. When the housing 220 is sufficiently engaged with the attachment member 218, optional tabs 271 may be inserted and secured within openings 272 (only one opening shown in FIG. 6). The tabs 271 may protrude past the interior surface of the housing 220 such that, when the housing is unthreaded and withdrawn from the attachment member 218, the tabs engage a raised lip 274 of the attachment member to prevent inadvertent component separation. The tabs 271 may secure to the housing 220 via most any acceptable method including, for example, adhesive or press fit.

As illustrated in the figures, see, e.g., FIG. 7C, the collet 244 may include clocking features (e.g., one or more keys 276 located on the outer surface of the piston 246) that engage the attachment member 218 (engage either or both of the keyways 253 and keyways 278 formed on the inner surface) and prevent relative rotation. The external surface of the attachment member 218 may also include one or more keys 280 (see FIG. 6) that engage corresponding keyways (visible in FIG. 4) on an inner surface of the second coupler 202 to prevent relative rotation of the couplers 202 and 204 during use.

At this point, the catheter 108 may be inserted into the first coupler 204, via the bell-mouth opening 264, until it bottoms out in the seal 238 (e.g., contacts the tubular member 240) as shown in FIG. 7A. The catheter 108 may include markings, e.g., laser markings (further described below), that assist the clinician in determining if the catheter is fully inserted. The housing 220 may then be moved until the female thread 258 engages the male thread 260 of the attachment member 218. Subsequent threading of the housing 220 onto the attachment member 218 results in compression of the seal 238, thereby sealing the fluid path between the first coupler 204 and the catheter 108.

Moreover, relative movement between the housing and attachment member results in engagement of the frusto-conical surface 266 with the legs 268 of the collet 244, which may eventually apply a mechanical force (e.g., a gripping or clamping force) to the catheter 108. The first coupler 204 (e.g., the collet 244) is preferably configured to ensure that the gripping force on the catheter is greater than the intended breakaway force of the connector 200. As a result, when a traction force is applied to the tube 102 and the catheter 108, the couplers 202 and 204 separate before the catheter 108 dislodges from the first coupler.

Preferably, the legs 268 of the collet 244 are configured to engage and grip the catheter 108 only after the seal 238 has been compressed. As a result, axial catheter movement resulting from seal compression may be accommodated before the collet immobilizes the catheter 108.

The catheter 108 may be configured such that it can be satisfactorily immobilized by the collet 244 without occlusion of the fluid passageway. For example, in one embodiment, the catheter could be made from an elastomeric material (pure or blended) such as a polymer, silicone, or the like. Exemplary embodiments of the catheter 108 are described in more detail below.

The tube 102, may, on the other hand, be constructed from conventional medical tubing such as polyurethane, silicone, or co-extrusions such as silicone/nylon or silicone/polyurethane. Alternatively, the tube 102 could be made from plasticized polyvinyl chloride (e.g., flexible PVC). In one embodiment, the tube 102 may have an inner diameter of about 0.07 millimeters (mm) to about 0.08 mm (e.g., about 0.076 mm) and an outer diameter of about 1.4 mm to about 1.5 mm (e.g., about 1.47 mm). While exemplary embodiments of the catheter and tube are so described herein, variations in material, construction, and size of the catheter 108 and tube 102 are certainly possible without departing from the scope of the invention.

Once the housing 220 is completely threaded onto the attachment member 218, the first coupler 204 is generally configured as shown in FIG. 4. The second coupler 202 may then be positioned proximate the first coupler 204 such that the bore 206 is generally aligned with the engagement portion 219. The engagement portion may then be slid into the bore 206 such that the roller 304 contacts the outer surface 222 of the engagement portion. This contact results in the roller assembly 301, e.g., the roller 304, being displaced outwardly (upwardly in FIG. 4) against the biasing force of the spring 306. The roller 304 may then roll along the engagement surface 224 until it reaches the ramped surface 228, at which point the roller may roll down the ramped surface and engage (contact) the grooved surface 226.

The biasing force of the spring 306 tends to keep the roller assembly 301 engaged with the grooved surface 226 during operation. To prevent backlash in the connector 200, the second coupler 202 and the first coupler 204 may include corresponding abutting surfaces 282 and 284, respectively (see FIG. 4), that contact one another once the couplers are fully connected as shown in FIG. 3.

While not wishing to be bound to any particular embodiment, the roller assembly may utilize an axle 302 having a diameter of about 0.050 inches (in) and the roller 304 (which may be made from acetal resin, PEEK, nylon, or the like) may have an outer diameter of about 0.09 in. In this embodiment, the grooved surface 226 may be recessed about 0.021 in below the engagement surface 224, and the ramped surface 228 may form an angle of about 50 degrees from the engagement surface.

As the second coupler 202 is attached to the first coupler 204, the needle 208 associated with the second coupler may pierce the septum 230 associated with the first coupler 204, thereby providing a fluid path from the second tube 102 to the first tube (e.g., the catheter 108). As a result, therapeutic agent contained in the infusion pump 106 (see FIGS. 1A-1B) may be delivered to the body through the tube 102 and catheter 108 in accordance with any desired infusion profile.

The retention device 300 is configured to release the first coupler 204 from the second coupler 202 once a predetermined traction force (the "breakaway force") is applied between the couplers, e.g., between the tube 102 and the catheter 108. In the illustrated embodiment, various features affect the breakaway force including, for example, the depth of the grooved surface 226, the angle of the ramped surface 228, the diameter of the roller 304, the friction of the roller about the axle 302, and the spring force of the spring 306. While not wishing to be bound to any particular range of parameters, embodiments of the present invention may provide a connector 200 having a breakaway force of about 1 pound force (lbf) to about 10 lbf and, preferably about 1 lbf to about 5 lbf, and more preferably, about 1.5 lbf to about 3 lbf.

When the predetermined traction force is reached, the roller 304 may move radially outward as it rolls from the grooved surface 226, along the ramped surface 228, to the engagement surface 224. The roller 304 may continue to roll along the engagement surface 224 until the couplers separate.

While described and illustrated herein utilizing the retention device 300, other retention mechanisms are possible without departing from the scope of the invention. For example, FIGS. 8A and 8B illustrate an alternate retention device 400. In this embodiment, the device includes a roller assembly having an axle 402 and a roller 404 rotatable about the axle. The axle 402 may be formed as part of a spring clip, e.g., C-shaped clip 406. The clip 406 may be configured to fit within a circumferential groove 408 formed in the body 410 of a second coupler. The roller 404 may be similarly contained within a slot 412 formed in the body. The body 410, while only partially illustrated in FIGS. 8A and 8B, is understood to be substantially similar to the body 205 of the coupler 202 described above (e.g., it includes a bore 414 to receive the attachment member 218 substantially as described above). A sleeve 416 similar to the sleeve 216 already described herein may also be included.

As with the retention device 300, the roller assembly, e.g., roller 404, may include a contact surface 418 formed by the outer surface of the roller. The contact surface 418 may form a secant through the bore 414 of the tubular body 410 when the roller is in a first position as shown in FIG. 8B. When the attachment member is inserted into the bore 414, the roller 404 may move to a second position (see broken line representation of axle 402) wherein the contact surface is located outside of the bore. Movement of the roller 404 may be accommodated via deflection of the clip 406 as may occur during insertion and removal of the first coupler 204 from the bore 414.

As with the device 300, the device 400 may engage the outer surface 222 of the attachment member 218 (see FIG. 4) in rolling contact. Moreover, the roller 402 may be biased in a generally radial direction to maintain rolling contact with the attachment member 218 of the first coupler during insertion/removal.

Connectors in accordance with embodiments of the present invention provide tubing/catheter couplers that breakaway or separate from one another when a predetermined traction force is applied to the couplers and/or to their associated tubes/catheters. Moreover, the retention device that interconnects the two couplers may minimize frictional engagement therebetween by providing rolling contact engagement. As a result, the breakaway force required to separate the couplers is substantially repeatable, avoiding the variability commonly associated with friction-based retention interfaces. Connectors in accordance with embodiments of the present invention further provide an upstream coupler (e.g., a coupler attached to an implanted catheter) that minimizes exposure to contamination even when the couplers of the connector separate. Accordingly, replacement or sterilization of the upstream catheter and/or coupler may be unnecessary in the event inadvertent separation of the connector occurs.

Connectors in accordance with embodiments of the present invention further provide a fluid flow path with minimal dead volume (the static volume that is filled before fluid is transferred through the connector). Reduced dead volume is advantageous as it may decrease the volume of wasted therapeutic agent. In the illustrated embodiment of FIG. 3, the connector (e.g., the region 286 between the second tube 102 and the needle 208, and the region 288 between the septum 230 and the seal 238) is designed to provide a low dead volume. For instance, connectors in accordance with embodiments of the present invention may have a dead volume of less than 20 microliters, and preferably less than 10 microliters, e.g., nominally about 7 microliters.

Catheters

As described above, the first tube or catheter 108 may be implanted and used to deliver the therapeutic agent to the body. Accordingly, the catheter 108 may be configured such that it can be satisfactorily immobilized by the collet 244 without occlusion of the fluid passageway. For example, as stated above, the catheter could be made from an elastomeric material (pure or blended) such as a polymer, silicone, or the like.

While some exemplary catheters may be constructed as generally uniform tubes, catheters in accordance with other embodiments of the invention may be configured to include an elongate tubular core or core member 107 (see, e.g., FIG. 7A) made from longitudinally flexible tubing that is resistant to compression and collapse, e.g., glass (e.g., silica or quartz) tubing, PEEK tubing, or stainless steel tubing. FIGS. 9A-9B illustrate an exemplary catheter having such a construction.

The core 107 may include a proximal end positioned at or near the proximal end 116 of the catheter 108, and a distal end positioned at or near the distal end 110 of the catheter as shown in FIG. 9A. The core 107 may also include a tubular body forming a lumen 117 spanning between the proximal and distal ends of the core. In the illustrated embodiment, the tubular core 107 may have an inner (e.g., lumen 117) diameter of about 80 micrometers to about 120 micrometers (e.g., about 100 micrometers) and an outer diameter of about 200 micrometers (e.g., about 193 micrometers), yielding a radial or wall thickness of about 50 micrometers or less. An exemplary core 107 may be a flexible synthetic fused silica capillary having an optional thin protective polymer (e.g., polyimide) coating (forming an intermediate layer between the core and an outer covering or jacket 109) such as the TSP line of products sold by Polymicro Technologies, LLC, of Phoenix, Ariz., USA.

The flexible outer covering or jacket 109 may be formed over the tubular core 107, e.g., it may surround the tubular core and be secured or otherwise fixed relative to the core's outer surface. While the flexible outer covering or jacket is described in the illustrated embodiments as an elastomeric jacket 109, this construction is not limiting as other outer covering embodiments are certainly possible without departing from the scope of the invention.

In one embodiment, the jacket 109 may have an outer diameter that is about 3 or more times larger, and preferably about 4 or more times larger (e.g., about 4 to about 6 times larger), than the outer diameter of the tubular core 107. For example, the outer diameter of the jacket 109 may be about 0.8 mm to about 1.2 mm (e.g., about 1 mm).

The jacket 109 may be formed of an elastomeric material having a radial compliance that is greater than a radial compliance of the tubular core 107. In one embodiment, the elastomeric jacket 109 is made from a material selected from the group consisting of polyurethane and silicone. As a result of using a relatively compliant material, the flexible outer covering or jacket may permit high mechanical clamping/indentation forces to be applied to the catheter 108 (e.g., by the connector 200 or, as described below, by the anchor 1200) to immobilize it, while the more radially rigid tubular core 107 prevents catheter occlusion under such high forces. While not limited to any particular hardness, the jacket 109 may, in one embodiment, have a hardness of about 50 to about 60 Shore D, e.g., about 55 Shore D (at the completion of manufacture).

As illustrated in FIG. 9A, the tubular core 107 may, in some embodiments, protrude longitudinally beyond the jacket or covering 109 at one or both ends of the catheter (e.g., beyond a distal end 119 of the jacket as shown) by a distance 124 of, e.g., about 10 mm or more. Stated alternatively, the jacket 109 may terminate a distance of about 10 mm short of the distal end of the core 107.

FIG. 9B illustrates a section view of the catheter 108 taken along line 9B-9B of FIG. 9A. As illustrated in this view, the catheter may optionally include one or more locator markings. For instance, a marker band, e.g., a fluoroscopic or radiopaque marker band 131, may be located at or near the distal end 119 of the outer covering (e.g., jacket 109). The band 131 may include platinum, iridium, or a similar material that may permit detection of the band with fluoroscopic or x-ray imaging. Such a configuration may be beneficial, for example, during implantation of the catheter into the body.

The catheter 108 may further optionally include other locator markings, e.g., longitudinal markings 132 (only two shown on catheter 108 in FIG. 9A). The longitudinal markings 132 may be evenly spaced and include some colorant (e.g., titanium dioxide) to permit visual indication of catheter implant depth. The markings 132 may also be used to determine proper placement of the proximal end 116 of the catheter within the connector 200.

FIGS. 10A-10E illustrate a catheter, e.g., a catheter 508, in accordance with an alternative embodiment of the invention. The catheter 508 may be similar in some respects, and be used in place of, the catheter 108.

Like the catheter 108, the catheter 508 may include a radially rigid yet longitudinally flexible tubular core or core member 507 (of a first material, e.g., PEEK tubing) having a distal end and a proximal end. A flexible outer covering or jacket 509 may surround the core (see, e.g., FIGS. 10A and 10D). However, instead of a single tubular core member extending along the catheter, the catheter 508 may incorporate a separate tubular tip or tip member 510, e.g., a composite tip member made of a second material different than a material of the core member 507. The tip member 510, like the core 507, may also have proximal and distal ends as shown in FIG. 10A.

The tip 510 may be configured as a relatively rigid (both radially and longitudinally) member. For instance, in one embodiment, the tip 510 may be formed from fused silica glass tubing. In another embodiment, the tip 510 may be made from steel, e.g., type 304 stainless steel hypodermic tubing. The proximal end of the tip 510 may be positioned to abut the distal end of the core 507 (e.g., be positioned in abutting contact at location 511 as illustrated in FIGS. 10A and 10B) such that a generally continuous lumen extends or is established from the proximal end of the core 507 to the distal end of the tip 510. While described herein as abutting one another, in practice the two members 507 and 510 may have a small gap therebetween, e.g., the adjacent ends of the tip and core may be positioned to be near, rather than abut, one another. Nonetheless, the jacket 509 may effectively seal the interface and provide a generally continuous lumen as described.

While not wishing to be bound to any particular construction, the materials and geometry of the tip 510 and core 507 may be selected to produce a bending stiffness ratio (ratio of the bending stiffness of the tip to bending stiffness of the core) of about 24:1.

The jacket 509 may surround or encase longitudinal sections or portions of both the tip 510 and the core 507 as further described below. As with the catheter 108, the distal end of the tip 510 may protrude a preset distance beyond a distal end of the jacket as shown in FIG. 10A. The tip 510 may also extend into the jacket 509 a distance that is sufficient to ensure retention of the tip. For example, in one embodiment, the catheter length (including the protruding length 124 of the tip 510) is about 400 mm (about 16 inches), while the tip extends into the jacket a distance 134 of about 20 mm, (about 0.8 inches).

FIG. 10C illustrates a cross section of the catheter 508 taken along line 10C-10C of FIG. 10A, while FIG. 10D illustrates a section view of the distal end of the jacket 509. These views clearly illustrate the marker band 131 (as described above) formed, at least in one embodiment, as a ring located around the tip 510 and surrounded by the jacket 509. In one embodiment, the marker band may extend a short distance 136, e.g., about 1 mm, from the end of the jacket. As with the catheter 108, the catheter 508, e.g., jacket 509, may also include the longitudinal length markings 132 (only two shown in FIG. 10E). The markings 132 and band 131 may be visible from any radial position, e.g., they may extend 360 degrees around the catheter.

In still yet other embodiments, strengthening members, e.g., braided members helically-wound about a longitudinal length or portion of the catheter, and/or straight longitudinal members, may be provided. For example, strengthening members may be sandwiched between the core and the flexible outer covering or jacket (e.g., such that they are surrounded by the jacket), or alternatively embedded within the jacket. Exemplary strengthening members may include polyester (e.g., polyethylene terephthalate (PET)), synthetic polymers such as Kevlar brand fiber (sold by E. I. du Pont de Nemours of Wilmington, Del., USA), and liquid crystal polymers. In other embodiments, steel may be used to form the strengthening members. Such strengthening members may be incorporated into any of the catheter embodiments (e.g., 108, 508, and 608, the latter of which is described below) described herein.

An exemplary catheter 608 incorporating such strengthening members is shown in FIGS. 11A-11E. The catheter 608 may be similar in most respects to the catheter 508. For instance, it may include a core or core member 607 (e.g., PEEK core) and a flexible outer covering or jacket (e.g., polyurethane jacket) 609 optionally having locator markings such as marker band 131 and longitudinal markings (not shown) as already described herein. As a result, a section taken through line 11D-11D (see FIG. 11D) is similar in most respects to the corresponding section taken through line 10C-10C of FIG. 10A (see, e.g., FIG. 10C).

A tip 610 substantially similar to the tip 510 already described above may also be included. The jacket 609 may encase at least sections of both the core 607 and the tip 610 as further described below. Once again, as shown in FIG. 11B, the tip 610 may abut the core 607 at a location 611 (e.g., offset a distance 634 from the distal end of the jacket) such that a continuous lumen is formed through the catheter. The tip 610 may further extend from the distal end of the jacket by a distance 124 as already discussed above.

Figure 11C:
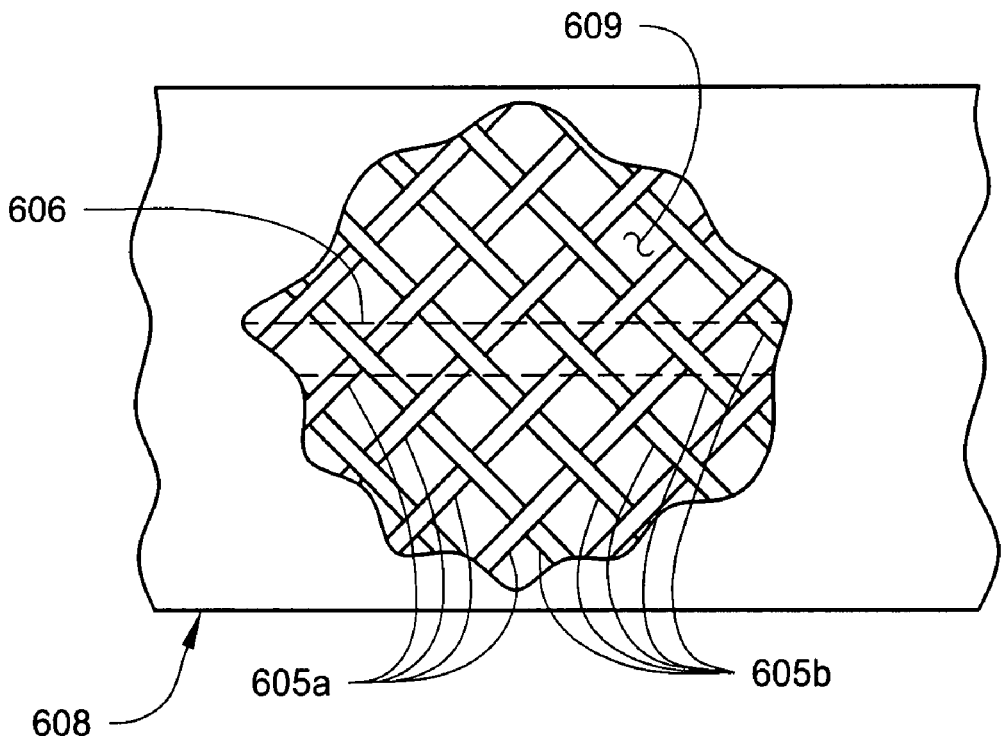

Unlike the catheter 508, however, the catheter 608 may further include one or more strengthening members 605 extending along at least a portion of a length of the catheter. In the illustrated embodiment, the strengthening members 605 may form a tubular braid located coaxially about portions of one or both of the core 607 and the tip 610 (note: the members 605 are shown diagrammatically in the figures). Stated another way, the individual members 605 may include a plurality of first braided members 605a helically wound about a longitudinal portion of the catheter 608 (e.g., about at least portions of the core and/or the tip 510) in a first or clockwise direction, and a plurality of second braided members 605b helically wound about the longitudinal portion in a second, opposite or counterclockwise direction (as shown in FIG. 11C) such that individual members interweave with one another. Other embodiments may include, alternatively or in addition, one or more longitudinal strengthening members 606 extending along portions of one or both of the core and the tip as also shown in FIG. 11C.

Figure 11E:
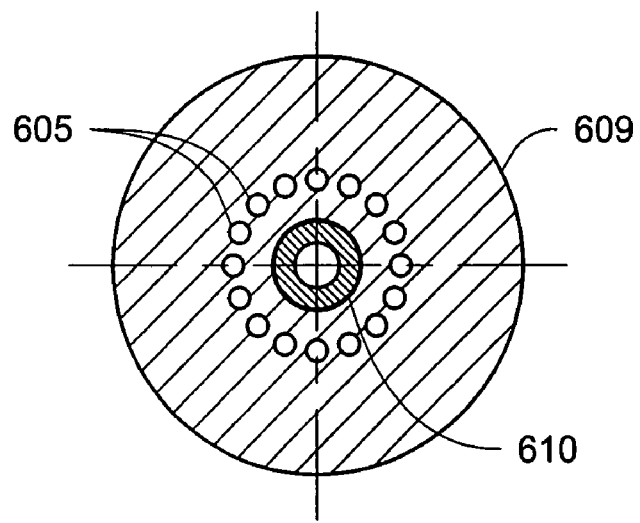

In one embodiment, the strengthening members 605 (e.g., the members 605a and 605b) include sixteen separate, 0.05 mm (0.002 inch) diameter PET fibers that are partially embedded within the jacket 609 as shown in FIGS. 11C and 11E, the latter of which is a section view taken along line 11E-11E of FIG. 11B. These strengthening members 605 may extend along at least a portion of the catheter 608. For example, in the embodiment illustrated in FIG. 11A, the members 605 may terminate a distance 138 short of the distal end of the jacket 609. The strengthening members 605 may also extend towards the proximal end of the catheter at least beyond the location 611 (e.g., so that they surround the distal end of the core 607 and the proximal end of the tip 610 as shown) to increase strain relief to the catheter in the vicinity of the location 611. In the illustrated embodiment, the strengthening members 605 may extend to the proximal end of the catheter 608.

While not wishing to be bound to any particular embodiment, the exemplary catheter 608 may again be about 400 mm (16 inches) long (including the protruding tip 610). The distance 138 (the termination offset of the strengthening members 605 from the distal end of the jacket 609) may be about 10 mm (0.4 inches), while the distance 634 at which the core member 607 abuts the tip member, may be about 20 mm (0.8 inches). The preset distance 124 may again be about 10 mm (0.4 inches), which may thus be equal to about ⅓ of the total length of the tip member 610. The small diameter, protruding distal tip of the core may assist in, for example, penetrating tissue during implantation.

The catheter embodiments illustrated in FIGS. 10A-10E and 11A-11E may provide a catheter having: a distal end section 140 defined by the protruding (e.g., stainless steel or glass) tip member 610; a proximal end section 142 defined by the portion of the catheter incorporating the core member 607; and a medial section 144 between the distal and proximal end sections (see, e.g., FIG. 11A). The jacket 609 may extend along and surround both the medial section 144 and the proximal section 142. The distal end section 140 may thus have a longitudinal portion with a uniform outer diameter less than an outer diameter of one or both the proximal end section 142 and the medial section 144. As a result of the different material of the core 607 and tip 610, the distal end section 140 may also have a bending stiffness that is greater than a bending stiffness of the proximal end section 142.

The outer covering or jacket 109 may be applied to the respective tubular core 107 in any known fashion (the following description may also apply to the jackets 509 and 609 and their respective cores 507 and 607). For example, it may be applied over the core 107 through a secondary extrusion process. Alternatively, the outer covering or jacket 109 may form a tube which slides over the tubular core 107 with clearance. In the case of the latter, two or more abutting tubing segments may be employed to produce the jacket 109. These multiple segments may also be beneficial in providing the proper spacing for the longitudinal markings 132. A shrink-wrap tube may then be placed over the assembled tubes and the entire assembly heated. Any optional strengthening members (e.g., woven fibers 605) may also be placed over the tubular core 107 or the outer covering 109 before the heat shrink tube is applied. Subsequent heating of the assembly may cause the outer covering 109 to melt and the shrink-wrap tube to constrict. Thus, the shrink-wrap tube may force the melted outer covering (and optional strengthening members) inwardly towards the tubular core 107 and bond to the same. The shrink-wrap tube may then be removed to produce the catheter 108.

Anchors

Embodiments of the instant invention may also be directed to anchor devices and assemblies and to corresponding systems and methods for securing a therapy delivery device relative to a surface, e.g., a surface of a body. For example, exemplary anchor assemblies and devices described herein may be configured to secure a therapy delivery device (such as a stimulation lead or infusion catheter 108) that is partially implanted through a skin-covered body portal. Moreover, these anchor assemblies may be manipulated from a location outside of the skin (e.g., outside of the patient's body) to release the therapy delivery device, e.g., at therapy completion. Once released, the device may be withdrawn from the body, e.g., by application of an external force or other action. As a result, the therapy delivery device may be removed from the patient without a separate surgical procedure.

While the term "skin" is used herein to identify an exemplary covering of the body portal, this term is not to be read in a limiting sense. That is, embodiments of the present invention are equally applicable to portals covered by most any material, including grafts, medical dressings, and other synthetic and biologic coverings, as well as to uncovered portals.

In the described embodiments, an anchor portion of the anchor assembly 1201 is configured as the burr hole anchor 1200 (see FIG. 1A). The anchor may be part of the system 100 for infusing a therapeutic agent into the patient's brain via the brain catheter 108 passing through the burr hole 112 formed in the skull. The anchor 1200, which may be subdermally located, may be used to secure the catheter relative to the burr hole. The anchor assembly 1201 may include the anchor 1200 as well as the lock member 1208 to release the catheter 108 from the anchor, e.g., at therapy completion.

While described herein in the context of burr hole anchors and corresponding infusion systems, anchor assemblies and systems in accordance with embodiments of the present invention may find use in most any medical (or non-medical) application that involves access through a portal formed in a surface.

FIGS. 1A and 1B illustrate the exemplary implantable medical system, e.g., brain infusion catheter system 100. Once again, the exemplary infusion system 100 may include the first medical tube, e.g., the brain catheter 108, partially implanted within the body 101. The second medical tube 102 may also be provided having its distal end 104 coupled to an external reservoir (e.g., infusion pump 106) containing a volume of the therapeutic agent. In the illustrated example, the brain catheter 108 has an indwelling portion, e.g., the distal end 110, implanted through a body portal (e.g., burr hole 112) and located at a predetermined location within the brain 114 of the patient. An external portion (e.g., the proximal end 116) of the brain catheter 108 may be routable through skin covering the skull 113 (see FIG. 12) and extend outside the body 101 where it connects to the corresponding proximal end 118 of the tube 102, e.g., via the connector 200.

The breakaway connector 200, as described above, may include the first coupler or connector portion 204 coupled to the brain catheter 108 and the second coupler or connector portion 202 coupled to the tube 102 as shown in FIG. 1B. Once again, the first coupler 204 may be operable to separate from the second coupler 202 when a traction force applied between the tube 102 and the brain catheter 108 reaches a predetermined threshold value. That is, the connector 120 may be configured to separate once a predetermined traction force is applied across the connector, e.g., between the two tubes 102 and 108 joined by the connector. The connector 200 may utilize either frictional or non-frictional (e.g., magnetic)

interfaces to achieve the breakaway function. As discussed above, the breakaway function may be beneficial to reduce inadvertent catheter dislodgement as the result of snagging of the tube 102 or other system 100 components on surrounding objects.

As already described herein, the connector 200 may be supported, e.g., pivotally supported, by the optional headgear apparatus 120 (see FIGS. 1A and 2B) formed from a series of adjustable, fabric (e.g., nylon webbing) or elastic bands. The headgear apparatus 120 may hold the connector, e.g., via a connection with the first coupler 204, during the implantation. While illustrated as supported by the headgear apparatus 120 in FIG. 1A, the connector 200 could alternatively be generally unsupported, e.g., supported only by the free proximal ends 116 and 118 of the catheter 108 and tube 102, respectively, without departing from the scope of the invention. The exemplary breakaway connector 200 is described elsewhere herein and in related U.S. patent application Ser. No. 11/589,694, filed on Oct. 30, 2006). While the exemplary connector 200 is described herein, other embodiments that utilize connector configurations providing an alternate breakaway configuration are certainly possible. For example, connectors using a snap-fit lock (e.g., similar to that disclosed by Lickliter in U.S. Pat. No. 6,902,207) or those incorporating a magnetic lock (e.g., similar to that disclosed by Cator in U.S. Pat. No. 3,181,895) could be used.

The system 100 illustrated in FIGS. 1A and 1B may further include a portal anchor device, e.g., the burr hole anchor 1200. The anchor 1200 may attach to the body, e.g., to the skull 113, in or near the burr hole 112. The anchor 1200 may be used to selectively immobilize the catheter 108 relative to the burr hole 112. In the illustrated embodiment, all, or substantially all, of the anchor 1200 is positioned subdermally (e.g., below the skin). The anchor 1200 forms part of the anchor assembly 1201 that further includes the lock member 1208 capable of selectively releasing the brain catheter 108 from the anchor. The lock member (further described below) may be releasable, or otherwise actuatable, from a location outside of the skin.

While the embodiments described and illustrated herein are directed to catheter implantation and anchoring, this is not limiting as most any other therapy delivery device (e.g., stimulation lead) may be used with the anchor embodiments described herein without departing from the scope of the invention.

Figure 12:
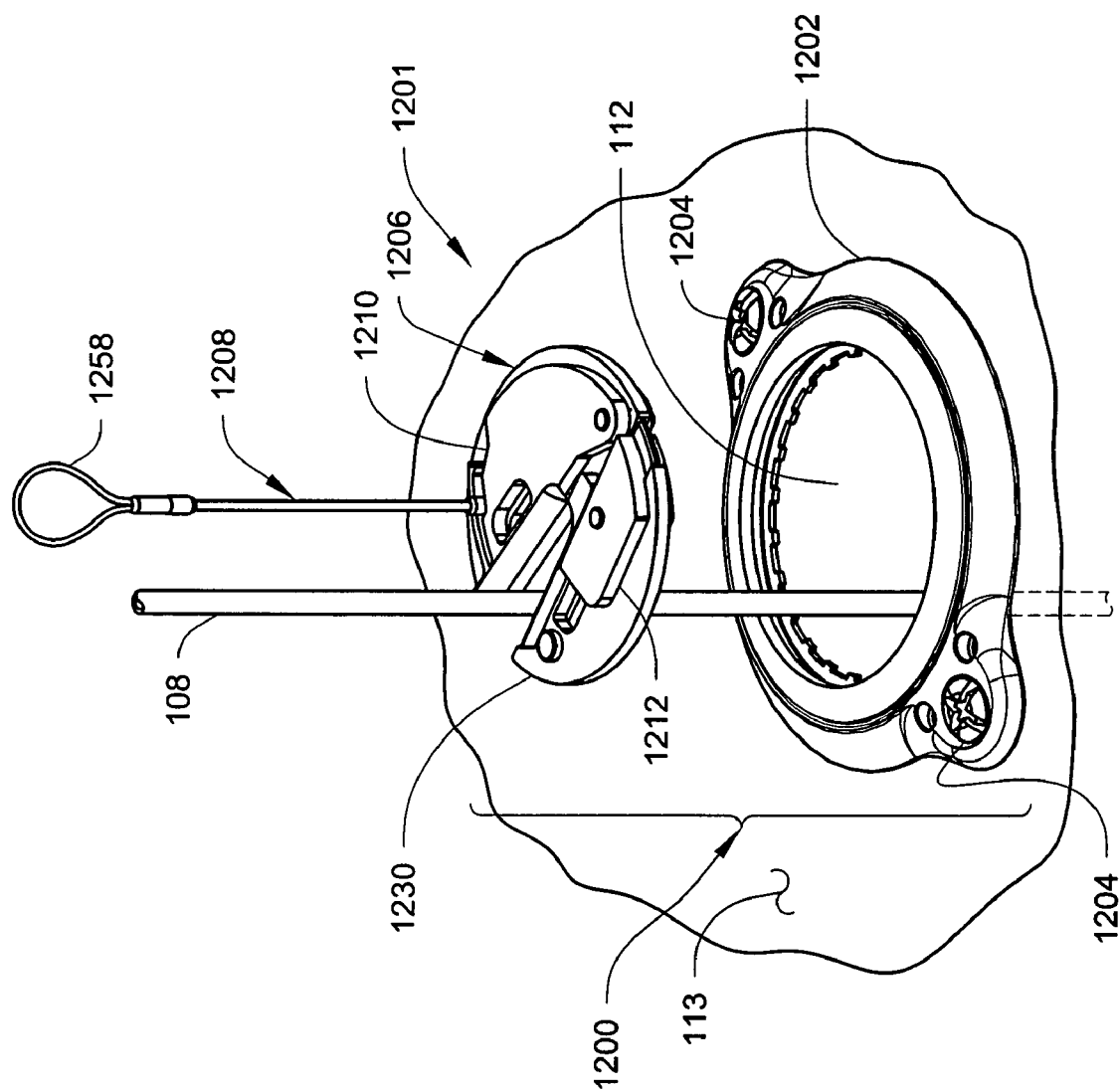
FIG. 12 is a perspective view of the exemplary anchor assembly, e.g., burr hole anchor, of FIGS. 1A-1B with a base of the anchor shown attached to the body, e.g., skull, and a retainer of the anchor shown before attachment to the base.

FIG. 12 is a perspective view of the portal, e.g., burr hole, site and illustrates an anchor system in accordance with one embodiment of the invention. The burr hole 112 may be formed through the skull 113 in a known manner prior to catheter 108 implantation. In the illustrative embodiment, the anchor 1200 includes a base 1202 that at least partially surrounds the portal (burr hole 112) and is attachable to tissue surrounding the portal, e.g., to the skull 113, with fasteners, e.g., bone screws 1204, or the like. The anchor 1200 may further include a retainer 1206 (shown exploded from the base in FIG. 12) that is attachable or otherwise securable to the base 1202 and is capable of selectively gripping or otherwise immobilizing the catheter 108. In some embodiments, the base 1202 may be optional. That is, the retainer 1206 could be positionable in or near the burr hole portal beneath the skin, where it may be secured to the skull in another manner, e.g., friction. The retainer 1206 may include a movable arm 1210 and a latch or latching device 1212, each of which is described in more detail below. The components of the retainer 1206 (e.g., body portion 1230 and arm 1210) may be constructed of most any biocompatible material, but are, in one embodiment, made from titanium.

Figure 13:
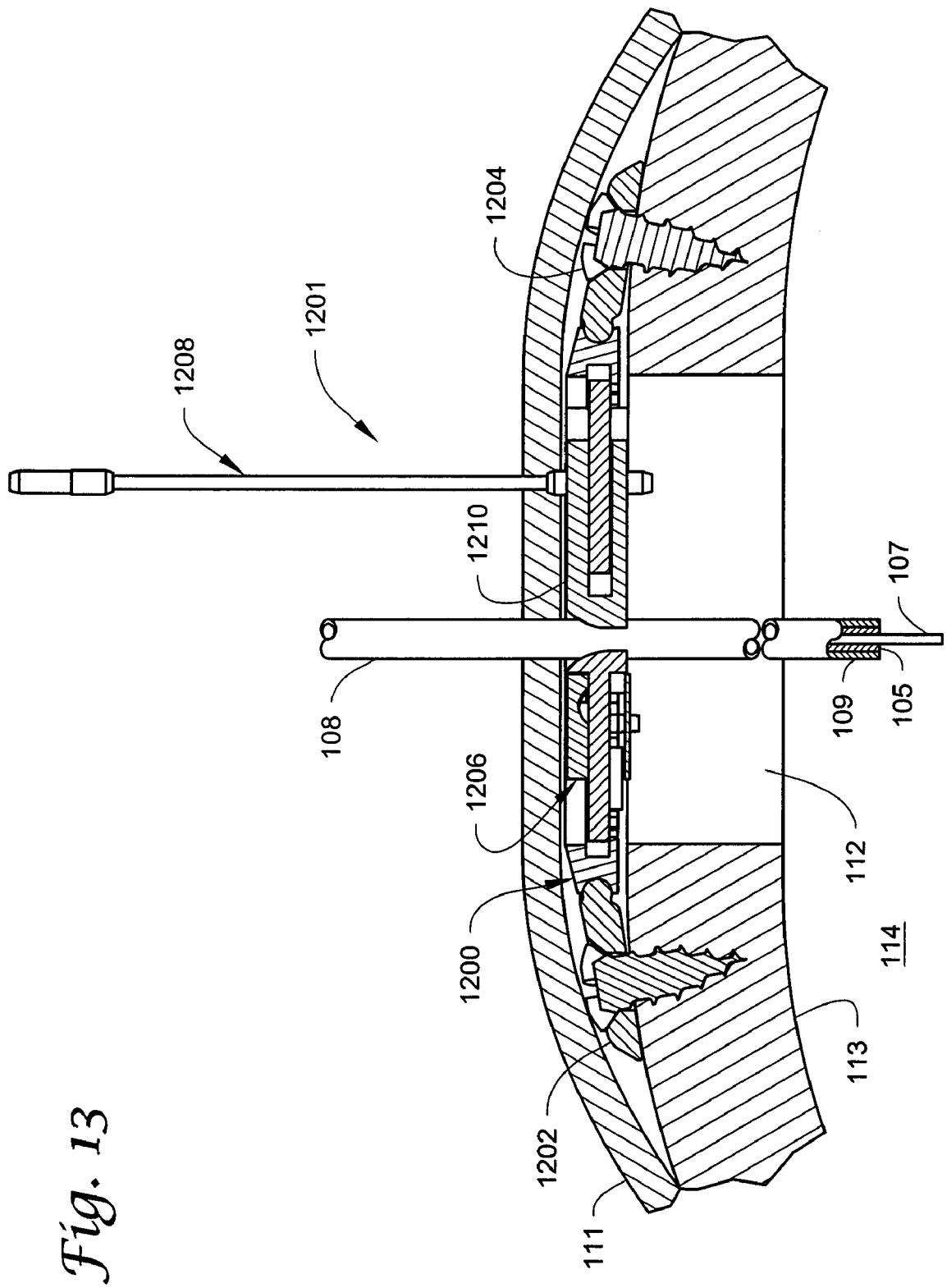
FIG. 13 is a cross section of the anchor assembly of FIGS. 1A-1B as it may be implanted within the body.

FIG. 13 illustrates a cross sectional view of the anchor assembly 1201 and catheter 108 after implantation. As evident in this view, the anchor 1200, e.g., the base 1202 and retainer 1206, are operable to be subdermally located (i.e., beneath the skin 111). As FIG. 13 further illustrates, the arm 1210 may move from a first or unlocked position shown in FIG. 12 (corresponding to the retainer being in a first or unlocked configuration), to a second or locked position shown in FIG. 13 (corresponding to the retainer being in a second or locked configuration). In the second position, opposing retaining surfaces 1234 and 1242 (see FIG. 14) may mechanically engage the catheter 108 and hold it in place relative to the burr hole 112. The lock member 1208 may be configured to hold or secure the arm 1210 in the second position. The catheter 108 and the lock member 1208 may, at the completion of implantation surgery, extend outwardly through the skin 111 covering the skull 113 and the now-implanted anchor 1200.

Figure 14:
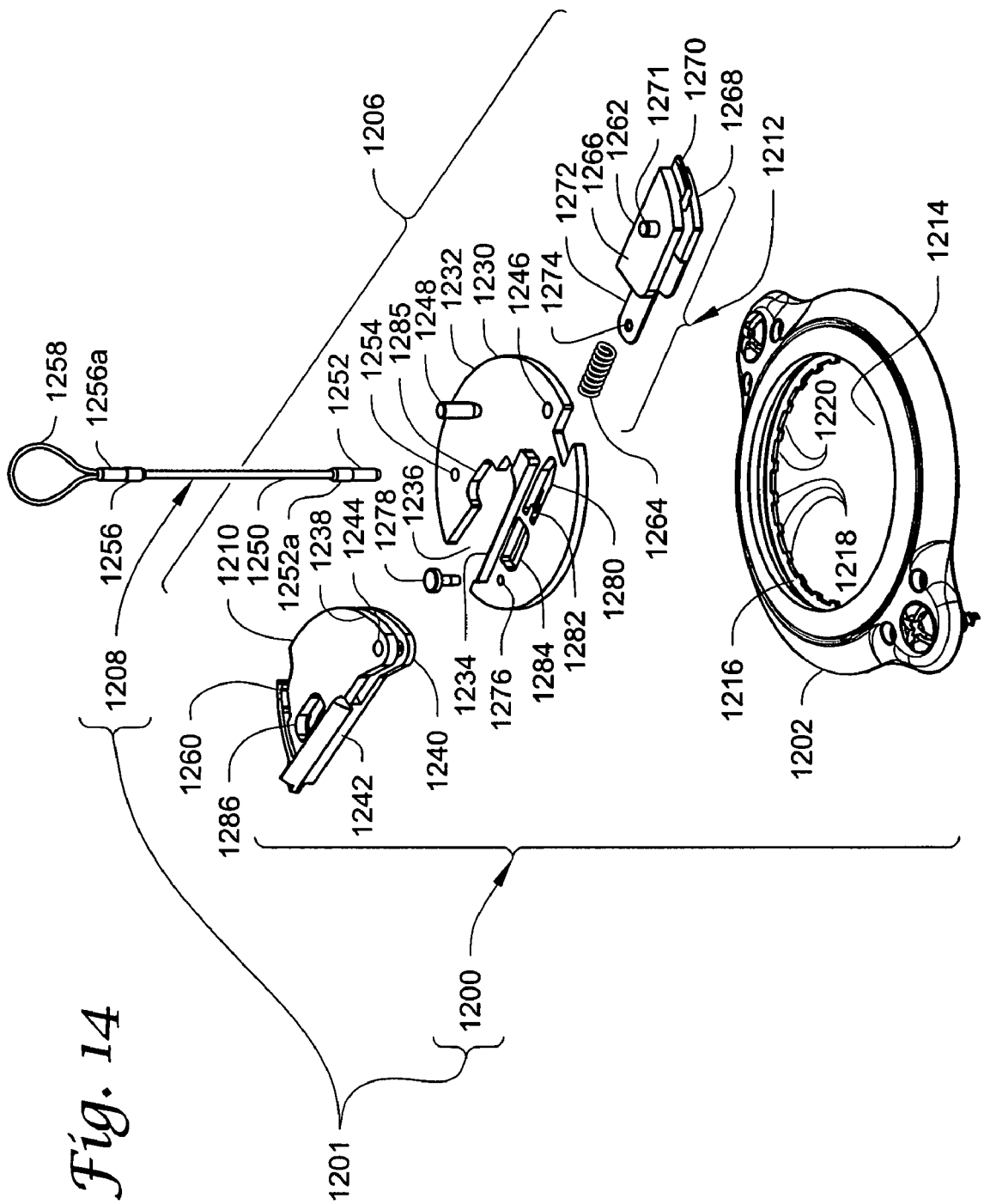
FIG. 14 is an exploded perspective view of the anchor assembly of FIGS. 1A-1B.

FIG. 14 is a perspective view of the base 1202 with the retainer 1206 exploded to illustrate an exemplary construction. In this embodiment, the retainer 1206 includes the planar, disk-shaped body or body portion 1230 that defines a mounting plane. The base 1202 may form a peripheral portion of the anchor 1200 that defines a central opening 1214. An inner surface of this peripheral portion may form a ledge 1216 to receive and support a peripheral edge 1232 of the body portion 1230 when the retainer is attached to the base in or near the central opening.

The ledge 1216 may, in one embodiment, be formed by a plurality of teeth 1218 protruding from the inner surface of the peripheral portion into the central opening 1214. A recess 1220 may be defined between adjacent pairs of the plurality of teeth 1218.

The body portion 1230 may further include a first retaining surface 1234 defined by an edge of a cutout or pie-shaped opening 1236 extending through the peripheral edge 1232. The first retaining surface 1234 may span from an interior of the body portion 1230 to a location at or near the peripheral edge 1232. As further explained below, the first retaining surface 1234 may be configured to mechanically engage the catheter 108 (not shown in FIG. 14) during use.

The arm 1210 may be movably, e.g., pivotally, attached to the body portion 1230. For example, the arm 1210 may include a second retaining surface 1242 that joins first and second plate members 1238, 1240. The plate members 1238, 1240 may form a clevis extending over both sides of the body portion 1230 when the arm 1210 is assembled with the body portion.

Figure 15:
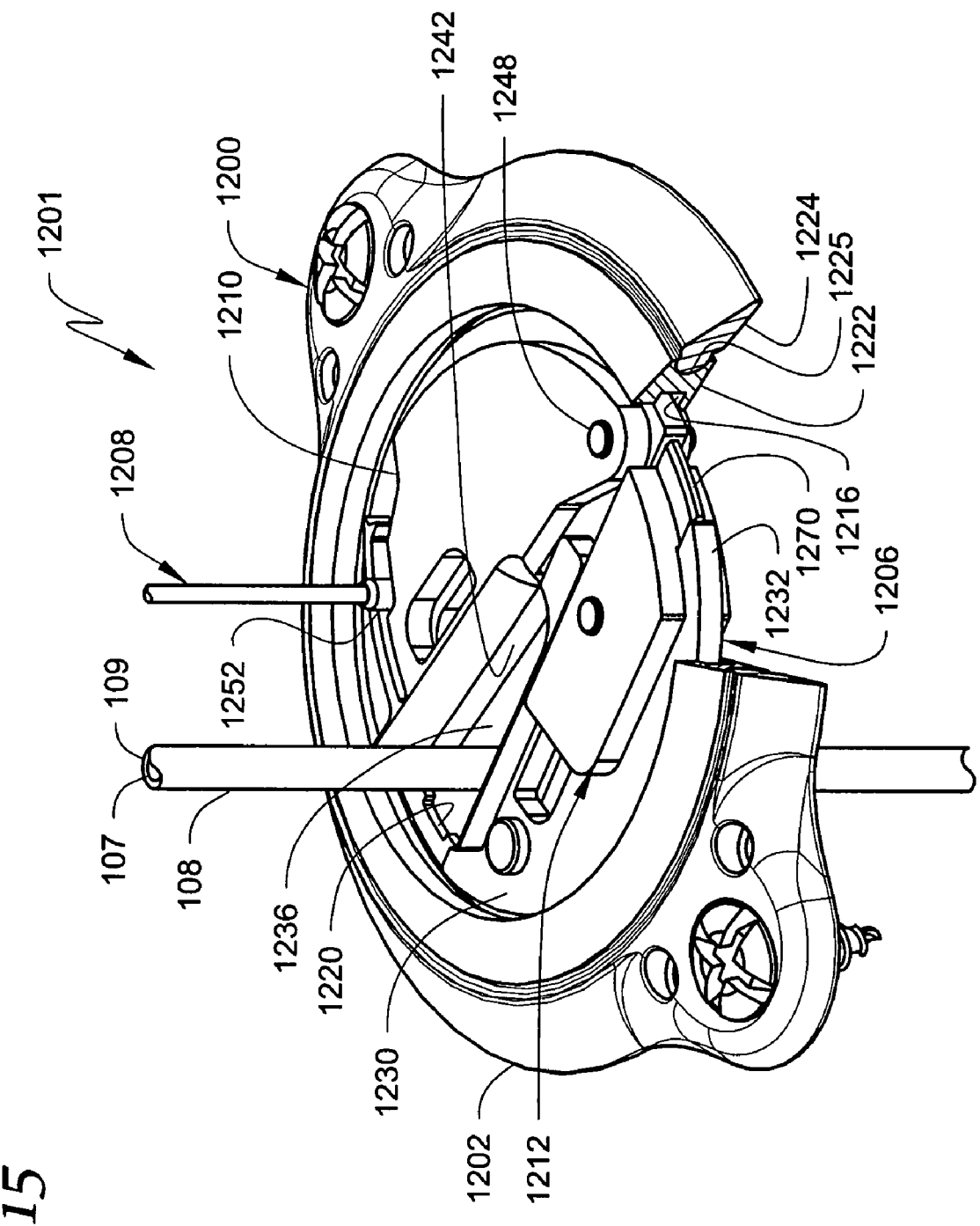
FIG. 15 is a partial cut-away view of the anchor of FIGS. 1A-1B, wherein the retainer is shown in a first or unlocked configuration corresponding to an arm of the retainer being in a first or unlocked position, and further wherein a latch of the retainer is shown in a first or unlatched position.

The two plate members 1238, 1240 may include openings 1244 that align with an opening 1246 in the body portion 1230 such that a pin 1248 may be inserted through the openings (the pin 1248 may engage either the arm 1210 or the body portion 1230 with interference) as shown in FIG. 15. The arm 1210 may thus pivot about an axis of the pin 1248. The second retaining surface 1242, e.g., the arm 1210, is therefore movable, relative to the first retaining surface, between the first position configured to receive the catheter 108 (see, e.g., FIG. 15), and the second position configured to mechanically engage the catheter (e.g., via friction or via a biting or clamping action) against the first retaining surface 1234 (see, e.g., FIG. 16). Thus, the catheter 108 may be immobilized or otherwise locked relative to the anchor 1200 via a pivoting motion applied to the arm 1210.

In embodiments wherein the catheter 108 is engaged via a biting action or a high frictional force, the catheter may be constructed of a compliant material that can withstand the contact forces of the first and second retaining surfaces as already described herein (see description of catheters 108, 508, and 608).

When the arm 1210 is in the first position, the second retaining surface 1242 may be oblique to the first retaining surface 1234, e.g., a line contained within the second retaining surface may intersect a line contained within the first retaining surface at an acute angle. This configuration provides for a larger opening in which to initially insert and position the catheter as shown in FIG. 15. However, when the arm is in the second locked position (see, e.g., FIG. 16), the first and second retaining surfaces are generally parallel to one another to permit generally equivalent contact force on the catheter regardless of the catheter's position along the retaining surfaces.

In addition to the anchor 1200, the anchor assembly 1201 may further include the lock member 1208. The lock member 1208 may be formed by an elongate member or cord 1250 that is removably coupled to the anchor, e.g., to the body portion 1230 of the retainer 1206. In one embodiment, the lock member 1208, e.g., the cord 1250, protrudes away from the body portion 1230 generally orthogonally from the mounting plane defined by the body portion. The cord 1250, in the illustrated embodiment, is configured to protrude through an opening or incision in the skin 111 as shown in FIG. 13. In one embodiment, the elongate cord 1250 is made from stainless steel stranded cable, e.g., 1×7, 1/64 inch diameter.

The exemplary lock member 1208 may also include a first end 1252 and a second end 1256. The first end 1252 may be attachable to the body portion 1230, e.g., detachably inserted into or otherwise received within an opening 1254 formed in the body portion (see, e.g., FIG. 14). The opening 1254 may position the lock member 1208, e.g., the first end 1252, such that it may interact with the arm 1210 as further described below. In the illustrated embodiment, the lock member 1208 is securely retained in the body portion 1230 during the implantation period and up until the lock member 1208 is intentionally removed. Such secure retention may be achieved in any number or ways, some of which are described in more detail below.

The first and second ends 1252 and 1256 of the lock member 1208 may be formed by sleeves 1252a and 1256a, respectively, which are attached, e.g., crimped or adhered, to the cord 1250. By utilizing the sleeve 1252a at the first end 1252, the tolerance of the first end 1252 relative to the opening 1254 may be closely controlled without concern for the size, material, or structure of the cord 1250. In one embodiment, the sleeves 1252a and 1256a are made of stainless steel.

The second end 1256, e.g., the sleeve 1256a, of the lock member 1208 may be used to provide a gripping surface to assist in lock member removal. In one embodiment, the sleeve 1256a may be used to secure an optional grasping loop 1258 as shown in FIGS. 12 and 14. The loop 1258 may be sized to permit insertion of a finger to assist the clinician with lock member removal.

The lock member 1208 is movable from an engaged state in which the lock member is coupled to the retainer 1206 to hold the arm 1210 in the second position (see, e.g., FIGS. 13 and 16), to a disengaged state in which the lock member releases the arm from the second position. The lock member 1208 is preferably movable from the engaged state to the disengaged state via manipulation of the lock member from outside the skin, e.g., via application of a traction force to the second end 1256 of the lock member to remove the latter from the retainer 1206.

Figure 16:
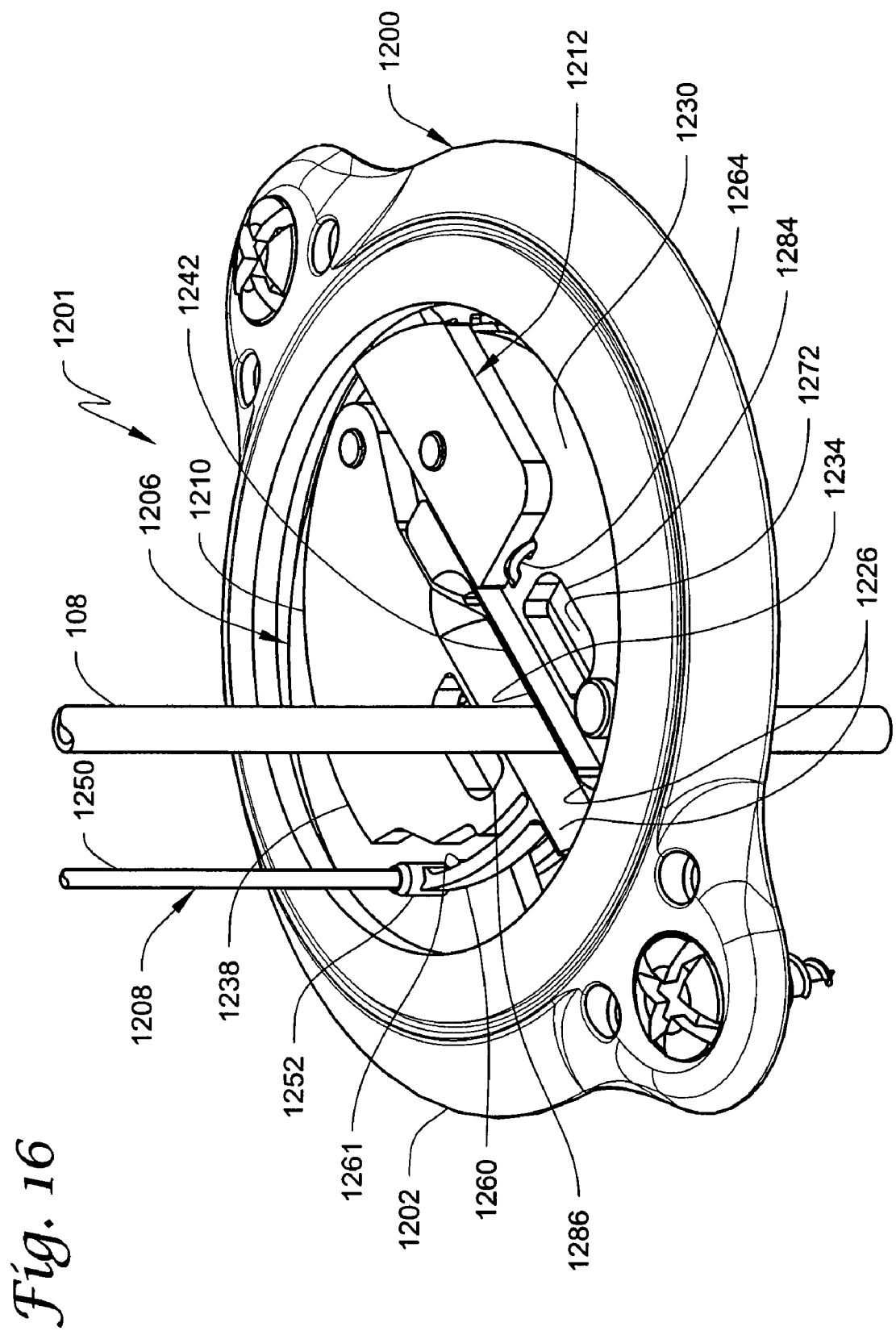
FIG. 16 is a perspective view of the anchor assembly of FIGS. 1A-1B with the retainer shown in a second or locked configuration corresponding to the arm being in a second or locked position, and the latch of the retainer shown in a second or latched position.

The lock member 1208 is configured to secure or lock the arm 1210, e.g., the second retaining surface 1242, in the second or locked position, as shown in FIG. 16, by engaging a locking portion 1260 of the arm as further described below. While not visible in FIG. 16, the arm may include a locking portion 1260 on both the first plate member 1238 and the second plate member 1240 (see FIG. 20).

The lock member 1208 may be retained within the body portion 1230 via a variety of methods. For example, in one embodiment, the first end 1252 may be sized such that it is received into the opening with an interference or press fit, wherein the interference provides a suitable retention force. In another embodiment, the opening 1254 may form a slot that receives the first end 1252. Such a slot may provide advantages including added flexibility of the body portion 1230 during insertion/removal of the lock member 1208. As a result, tolerance control between the first end 1252 and the body portion 1230 could potentially be relaxed.

In yet another embodiment, a cantilever spring may be provided that is integral or otherwise associated with the opening 1254. The spring and opening may both provide a suitable retention force between the lock member 1208 and the body portion 1230 without necessitating the elevated tolerance accuracy typically associated for press fits. In still yet another embodiment, the first end 1252 of the locking member 1208 may be sized to freely slip into the opening 1254. The locking portion 1260 of each arm 1210 could then mechanically interfere with the first end 1252 to provide a frictional retention force. In one embodiment, this retention force may be about 0.1 pounds force (lbf) to about 1.1 (lbf). However, this range is exemplary only and embodiments that release upon the application of most any force are certainly possible without departing from the scope of the invention. In this embodiment, each locking portion 1260 may basically form a cantilevered spring that allows insertion, despite the mechanical interference, of the first end 1252 of the lock member 1208 into the body portion 1230. In still other embodiments, a detent bump 1261 (see FIG. 16) may be provided that creates a detent action to releasably hold the arm 1210 in the unlocked position. Due to the spring-like action of each locking portion 1260, a suitable detent holding force may be created.

The retainer 1206 may further include the latch 1212 as shown in FIG. 14 (also shown in section in FIGS. 19A and 19B). The latch 1212 may be used to secure the retainer 1206 relative to the base 1202. While shown in FIG. 14 as a separate component attached to the body portion 1230, the latch 1212 could, in other embodiments, be formed as an integral part of the retainer, e.g., deflectable snap fit tabs as further described below.

The latch 1212 may include a latch plunger 1262 that is biased outwardly by a biasing member, e.g., spring 1264. The latch plunger 1262 may be formed by first and second plate members 1266 and 1268 that are joined at a nose 1270. A pin, e.g., retaining pin 1271 may also extend between the plate members 1266 and 1268. The latch plunger 1262 may thus form a clevis that extends over both sides of the body portion 1230 when assembled.

The latch 1212, e.g., latch plunger 1262, is preferably movable from a first or unlatched position that is at or within the peripheral edge 1232 of the body portion 1230 (see, e.g., FIG. 15), to a second or latched position extending beyond the peripheral edge of the body portion (see, e.g., FIG. 16). The latch plunger 1262 is preferably biased towards the latched position by the biasing member (e.g., by the spring 1264).

A stop, such as tab 1272, may be provided on one of the plate members, e.g., the lower plate member 1268. The tab 1272 may be used to hold the latch plunger 1262 in the unlatched position. For example, the tab 1272 may include an opening 1274 that aligns with an opening 1276 in the body portion 1230 when the latch 1212 (e.g., the latch plunger 1262) is in the first unlatched position. A pin 1278, which may be fixed (e.g., via interference or adhesive) within the opening 1276, may then engage the opening 1274 (preferably with clearance) to hold the latch plunger 1262 in place.

The body portion 1230 may further include an opening, e.g., slot 1280, that receives and retains the spring 1264. A finger 1282 may extend into the slot 1280 to assist with spring retention. The retaining pin 1271, which may be installed when the latch plunger 1262 is in the first or unlatched position, may also extend through the slot 1280. As a result, the pin 1271 may limit the outward movement of the biased latch plunger 1262 and prevent component separation.

The body portion 1230 may define other features, e.g., slots 1284 and 1285, that assist in assembly and/or manipulation of the retainer as further described below. The arm 1210 may also include a slot 1286 that, in conjunction with the slots 1284 and 1285, assists in movement of the arm.

FIG. 15 illustrates a perspective view of the anchor 1200 with a portion of the base 1202 cut-away to show the ledge 1216 in more detail. In this view, the arm 1210 is shown in the first or unlocked position and the latch 1212 is shown in the first or unlatched position. As illustrated in this view, the base 1202 may be of two-part construction. A first or inner portion 1222 may form the ledge 1216 and its associated structure (e.g., the teeth 1218) to support the retainer 1206. A second or outer portion 1224 may include features (e.g., fastener attachment points) that assist in attaching the base 1202 to tissue (bone surface) surrounding the burr hole 112. The first portion 1222 may be relatively rigid (as compared to the second portion 1224) to ensure that the catheter 108 is adequately immobilized. The second portion 1224 is preferably more compliant than the first portion 1222. The compliance of the second portion 1224 allows the anchor 1202 to generally conform to the local shape of the skull 113 (see FIG. 12). In one embodiment, the first or inner portion 1222 of the base 1202 is made from titanium, while the second or outer portion 1224 is made from an implantable thermoplastic such as amorphous polyamide.

The second portion 1224 may be pivotally coupled to the first portion 1222 of the base 1202 via a ball and socket arrangement as shown in the cut-away portion of FIG. 15. For example, the inner surface of the second portion 1224 may include an inner circumferential lip 1225 that is convex in cross section as shown in FIG. 15. This lip 1225 may fit within an outer circumferential recess of the first portion 1222 that is concave in cross section as shown in FIG. 15. While the base 1202 is illustrated as having a two part construction, such a configuration is not limiting. For example, other embodiments of the base 1202 may utilize a single piece construction without departing from the scope of the invention. Such a single piece construction could include integral flexing elements, or flexures, to create a rigid portion and a conforming portion of the base 1202.

Other variations of the base 1202 are also possible. For example, while not illustrated herein, the base 1202 could be formed with a radial slot extending entirely through the ring that forms the base (e.g., yielding a C-shaped base). Such a construction may allow side loading of the base 1202 over the catheter 108 after the catheter is positioned but before the stereotactic positioning apparatus is removed.

FIG. 16 illustrates the anchor 1200 of the anchor assembly 1201 with the latch 1212 in the latched position and with the arm 1210 in the locked position. In the locked position, the arm 1210, e.g., the second retaining surface 1242, mechanically engages the catheter 108 by clamping or pinching the catheter against the first retaining surface 1234. To reduce stress on the catheter 108, curved transition surfaces 1226 associated with either or both the first and second retaining surfaces 1234 and 1242 may be provided. As further shown in this view, the locking portion(s) 1260 of the arm 1210 may be configured to contact the lock member 1208 (when the arm is in the locked position) such that the arm is immobilized relative to the body portion 1230 of the anchor 1200.

To further illustrate the movement of the arm 1210, FIGS. 17 and 18 provide top views of the anchor assembly 1201. FIG. 17 illustrates the anchor assembly with the arm in the unlocked position and the latch in the latched position, while FIG. 18 illustrated the anchor with the arm in the locked position and the latch in the latched position (the catheter 108 is removed from these views for clarity). As illustrated in FIG. 17, the locking portion 1260 may form a resilient finger that may deflect to rest against the lock member 1208, e.g., against the first end 1252, when the arm is in the first or unlocked position. During the implantation procedure, the arm may be moved (e.g., pivoted about the pin 1248) to the locked position of FIG. 18 once the catheter 108 is located at the desired position within the central opening 1214. The arm 1210 may be moved to the locked position by, for example, inserting an instrument such as forceps into the slots 1284, 1285, and 1286 and drawing the second retaining surface 1242 of the arm towards the first retaining surface 1234. A stop member, e.g., a protrusion 1289 formed on the body portion 1230, may be provided to limit the movement of the arm 1210 towards the first retaining surface, thus providing protection against catheter over-compression.

Figure 20:
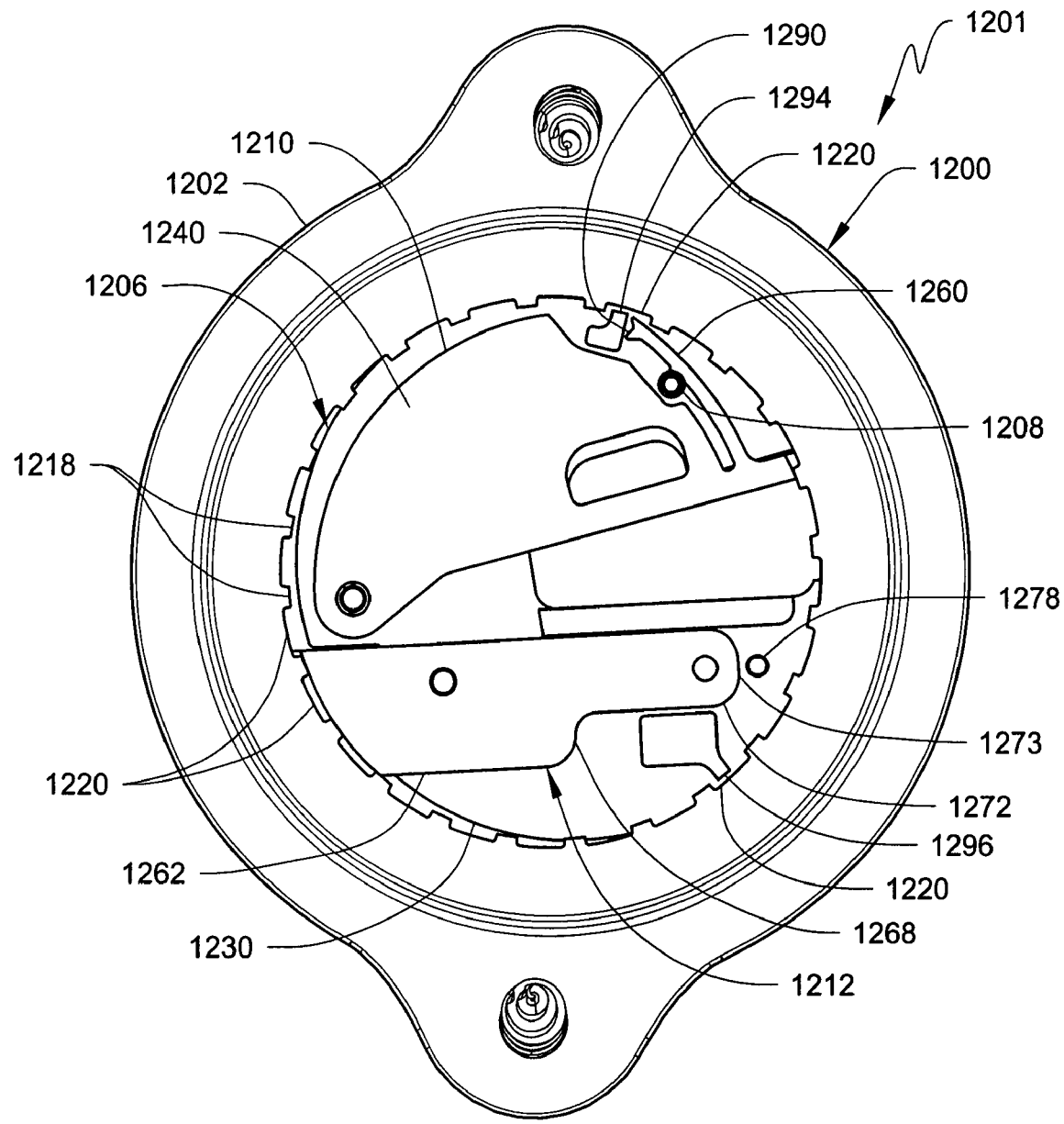
FIG. 20 is a bottom plan view of the anchor assembly of FIG. 17 with the latch shown in the latched position and the arm shown in the unlocked position.

When the arm reaches the locked position shown in FIG. 18, the locking portion(s) 1260 of the arm 1210 may slide past the first end 1252 of the lock member 1208. When the locking portion 1260 clears the first end 1252, it may return to an undeflected state. In this undeflected state, each locking portion 1260 of the arm 1210 is aligned with the first end 1252 of the lock member 1208 such that a lock surface 1290 (see FIG. 17) abuts the first end of the lock member as shown in FIG. 18. In the illustrated embodiment, the lock surface 1290 could be concave in shape to seat against the cylindrical shape of the first end 1252 of the lock member 1208 when the arm is in the second position. Alternatively, the lock surface 1290 may be formed by one or more linear surfaces tangent to the first end 1252 as best illustrated in FIGS. 17 and 20. When the lock surface 1290 is engaged with the lock member 1208, the arm 1210, e.g., the second retaining surface 1242, may be held in the locked position shown in FIG. 18.

As mentioned above, the lock member 1208 may be retained in the body portion 1230 with an interference fit. However, in some instances, e.g., when the arm 1210 is in the locked position as it is during infusion, it may be beneficial to increase the lock member retention force. Accordingly, some embodiments of the catheter 108, as already described herein, may be constructed with a lumen that is relatively rigid in (e.g., resistant to) radial compression. Such a catheter construction may increase the force applied to the first end 1252 of the lock member 1208 by the locking portion 1260, and thus increase frictional retention of the first end within the opening 1254 of the body portion 1230. In one embodiment, the retention force, e.g., the force required to remove the first end 1252 from the body portion 1230, may be about 0.1 lbf to about 3 lbf, e.g., about 0.5 lbf to about 2 lbf.

Prior to moving the arm 1210 to the locked position as described above, the retainer 1206 may first be latched or secured to the base 1202 using the latch 1212. Preferably, the retainer 1206 is secured to the base with the latch 1212 before locking of the arm 1210 to prevent undesirable transverse catheter movement during retainer latching.

FIG. 19A is a section view of the anchor 1200 taken along line 19A-19A of FIG. 17 illustrating the latch 1212 in accordance with one embodiment of the invention. However, unlike FIG. 17, FIG. 19A shows the latch in the first or unlatched position, while FIG. 19B shows generally the same view as FIG. 19A, but with the latch in the second or latched position (e.g., a true section view of FIG. 17).

As illustrated in FIG. 19A and described above, the retainer 1206 may be located within the central opening 1214 of the base 1202 where it may be positioned to rest upon the ledge 1216. Once the retainer 1206 is rotationally positioned, relative to the base 1202, to the desired orientation, the latch 1212 may be released to secure the retainer in place. In the illustrated embodiment, the latch 1212 may be released by releasing the tab 1272 from the pin 1278. Release of the tab 1272 may be accomplished by inserting a surgical instrument, e.g., forceps, through the slot 1284 and applying a slight downward force to the tab as represented by arrow 1287 in FIG. 19A. Alternatively, a specialized tool (not shown) may be used. This tool may provide a properly-sized actuator point, as well as an inherent limit stop, both of which may assist in the release of the tab 1272. The force may deflect the tab 1272, as illustrated by the broken line representation in FIG. 19A, sufficiently for the tab to release from the pin 1278. Once the tab 1272 is released, the spring 1264 forces the latch plunger 1262 away from the body 1206 of the retainer 1206. That is, the spring pushes the plate members 1266, 1268 and the nose 1270 outwardly towards the base 1202.

As the latch plunger 1262, e.g., the nose 1270, extends towards the inner portion 1222 of the base 1202, the spring 1264 also forces the body portion 1230 against the opposite side of the base as shown in FIG. 19B. When the latch 1212 is fully released or engaged (as shown in FIG. 19B), the nose 1270 and the body portion 1230 are pressed against opposing inner surfaces of the base 1202.

As illustrated in FIGS. 19A and 19B, the base 1202 may define a groove 1291 bounded by the ledge 1216 and by an upper surface 1292. The ledge and the upper surface substantially restrain the retainer 1206 against movement normal to the mounting plane of the body (i.e., along an axis of the central opening). Similarly, the biasing force of the spring 1264 may substantially restrain the retainer 1206 against radial movement relative to the base 1202. Alternatively (or in addition), a portion of the retainer (e.g., the pin 1278) may form a stop that limits movement of the latch plunger 1262 away from the latched position. This is accomplished, in one embodiment, by an end 1273 of the tab 1272. The end 1273 may abut the pin 1278 when movement of the latch plunger 1262 away from the latched position occurs, thus assisting with maintaining the latch in the latched position. As a result, the retainer 1206 may be secured within the central opening of the base 1202 via the latch 1212.

FIG. 20 illustrates a bottom plan view of the anchor after the latch 1212 is moved to the second or latched position of FIG. 19B and before the arm is moved to the locked position. As illustrated in this view, the latch plunger 1262 of the latch 1212 may force the retainer 1206 to a location slightly off-center from the base 1202 such that the retainer and base are no longer concentric. As the retainer 1206 is shifted transversely to the base, lock members, e.g., tabs 1294 and 1296, attached to the body portion 1230 may each engage one of the recesses 1220 of the base as shown. Engagement of the tabs 1294, 1296 with the recesses may reduce or eliminate excessive rotation of the retainer 1206 relative to the base.

Embodiments of the present invention may further include methods for delivering therapy via a partially implanted device extending through a covered portal such as the skin-covered burr hole 112. For example, an exemplary method may include securing the device (e.g., catheter 108) relative to the burr hole 112 with the subdermal anchor 1200. Securing the device 108 relative to the burr hole 112 may be accomplished by clamping the device between opposing retaining surfaces 1234, 1242 of the anchor 1200 during implantation as described above. The anchor 1200 may be attached to bone (e.g., to the skull) surrounding the burr hole, wherein the device 108 protrudes outwardly through the skin 111. The method may further include releasing the device 108 from the anchor 1200 by manipulation of the anchor from outside the skin 111. In one embodiment, releasing the device 108 includes applying a release (e.g., traction) force to the lock member 1208 protruding outwardly through the skin and removing the lock member from the anchor 1200. By then applying a force (e.g., traction force) to a portion of the device 108 that protrudes outside the skin, the device may be removed entirely from the patient.

In other embodiments, methods for removing a partially implanted device (such as the catheter 108) extending through the skin-covered burr hole are provided. For example, in one embodiment, the method may include applying a release (e.g., traction) force to a lock member (e.g., lock member 1208) extending through the skin 111, wherein the lock member is coupled to the subdermal anchor 1200 that is used to immobilize the device relative to the burr hole 112. The lock member may be detached from the anchor 1200 and withdrawn through the skin. By then applying a force (e.g., traction force) to a portion of the device 108 protruding outside the skin, the device may be removed entirely from the patient through the skin.

Figure 21A:
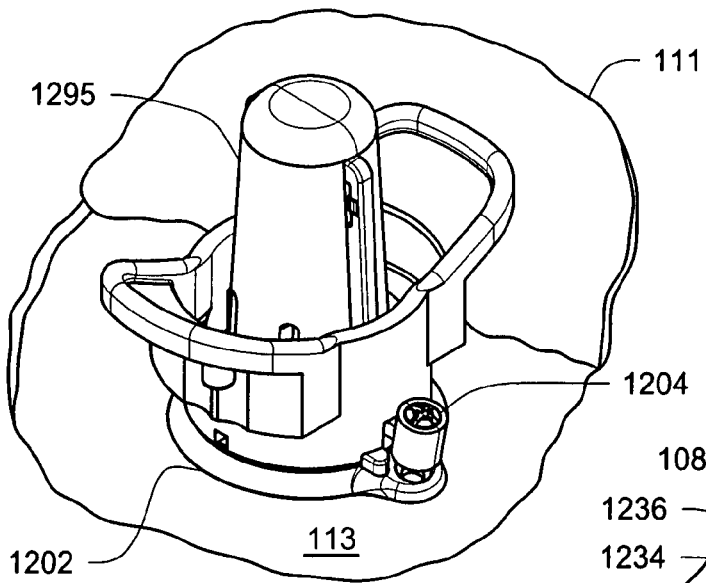

FIGS. 21A-21D illustrate an exemplary method of using the anchor assembly 1201 to secure and release the catheter 108 from within the burr hole. After peeling the skin 111 back to expose the skull 113 as shown in FIG. 21A, the burr hole 112 may be formed at a predetermined location in accordance with conventional practices. The base 1202 of the anchor 1200 may then be attached to the skull 113. To assist with attachment of the base, an attachment tool 1295 may be provided. The attachment tool may interlock with the base 1202 and align the latter with the burr hole 112. Once aligned, the attachment tool 1295 may also support and align the bone screws 1204 that are used to secure the base 1202 to the skull 113.

Once the base is attached to the skull and the tool 1295 is removed, the catheter 108 may be inserted through the burr hole 112 until the tip is located at the desired location within the brain. Catheter insertion and positioning may be accomplished with stereotactic instrumentation (not shown).

Figure 21B:
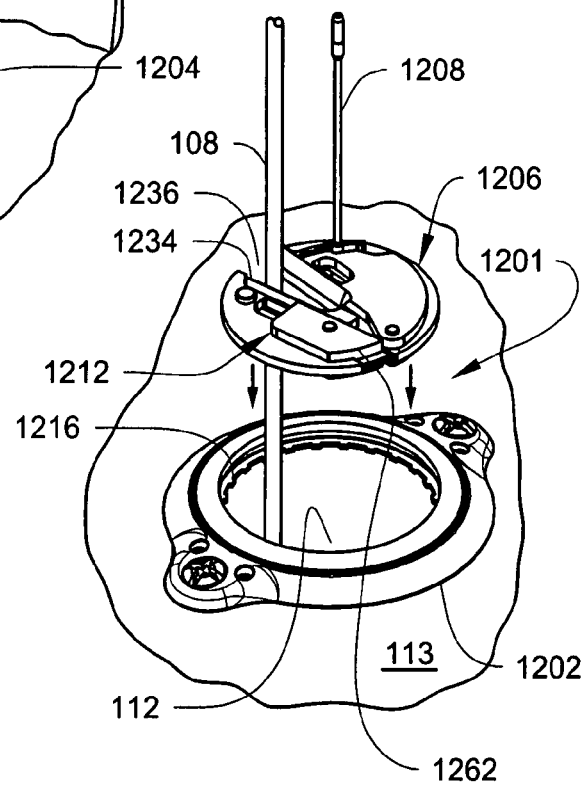

While the catheter 108 is supported with the stereotactic instrumentation, the retainer 1206 (assembled as shown in FIGS. 12 and 21B with the arm in the first or unlocked position and the latch 1212 in the first or unlatched position) may be side-loaded around the catheter 108 as shown in FIG. 21B such that the catheter enters the retainer via the opening 1236. The retainer 1206 (with the lock member 1208 attached) may then be set into the base 1202 where it may seat upon the ledge 1216 as already described herein.

Because the catheter 108 position within the burr hole 112 may vary depending on the targeting procedure utilized, the retainer 1206 is preferably operable to be rotated about its center axis. That is, the retainer 1206 may be rotated within the base 1202 until the first retaining surface 1234, at some location along its length, approaches or contacts the catheter 108. At this point, the latch 1212 may be activated to release the latch plunger 1262. As described above, the latch 1212 may be activated by inserting forceps or the like (not shown) into the slot 1284 (see, e.g., FIG. 17) to disengage the tab 1272 from the pin 1278 (see, e.g., FIG. 19A). Once released, the latch 1212 may secure the retainer within the base 1202.

With the retainer 1206 secured, the arm 1210 may be moved from the first unlocked position (see, e.g., FIG. 17) to the second locked position (see, e.g., FIG. 18). As described above, movement of the arm between the first and second positions may be accomplished by grasping the openings 1284 and 1286 with forceps and applying a closing force.

Figure 21C:
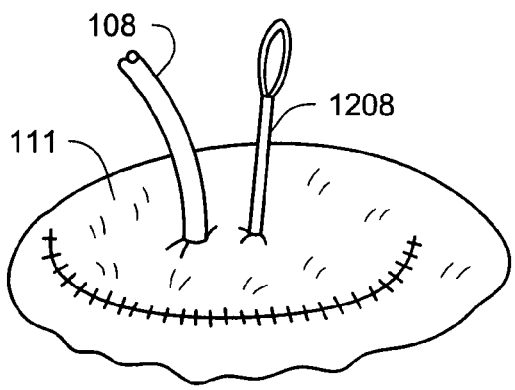

Once the catheter 108 is secured, the stereotactic instrumentation may be removed. After placing the skin flap 111 over the anchor, the incision may then be closed as shown in FIG. 21C. Two openings or punctures may be formed in the skin flap to permit the passing of the catheter 108 and the lock member 1208 through the skin. For example, one possible technique may involve piercing the skin from the outside with a needle or the like (e.g., Touhy needle), after which the catheter 108 (or lock member 1208) may be fed through the needle. The needle may then be withdrawn, leaving the catheter 108 (or lock member 1208) extending through the skin opening. The catheter 108 may then be connected to the infusion pump 106, e.g., via the connector 200 and second tube 102 as illustrated in FIG. 1A. Infusion of the therapeutic substance in accordance with a desired therapy delivery profile may then commence.

While not illustrated, other components may be utilized to reduce bending stress on the catheter 108 during implantation. For example, an elastomer (e.g., silicone rubber) strain relief plate or disk (not shown) may be attached to the surface of the skin (e.g., with adhesive or dressing). The strain relief plate may include an opening and/or a shaped guide slot through which the catheter 108 may pass. The opening/slot preferably holds the catheter as it is draped around the scalp and may reduce bending stress on the catheter in the event that the catheter is inadvertently pulled at an angle. The plate member may also include an opening for the lock member 1208 to pass. In other embodiments, the entire burr hole site may be dressed or bandaged. The bandage may include taping of the catheter to the body of the patient so as to provide the desired strain relief.

Figure 21D:
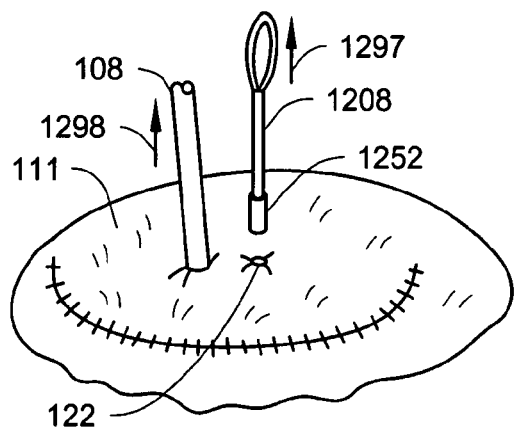

At, before, or after completion of therapy delivery, the lock member 1208 may be removed or detached from the anchor (e.g., removed from the opening 1254 in the body portion 1230) and withdrawn through the skin flap 111 by, for example, application of a release (e.g., traction) force from outside the body 101 as represented by arrow 1297 in FIG. 21D. Removal of the lock member 1208 permits the arm 1210 to release its mechanical engagement force on the catheter 108. Accordingly, the catheter may be subsequently removed from the patient by the application of a force applied to the catheter as represented by arrow 1298. Depending on the size of the lock member 1208 and the catheter 108, the skin punctures 122 remaining after device removal may require suturing. However, in other embodiments, the size of the both components is sufficiently small such that no sutures are required.

While described above in terms of passing the catheter 108 and lock member 1208 through separate openings or punctures, other embodiments are also possible. For example, the catheter 108 and/or lock member 1208 may extend through the skin at the original skin flap incision. Alternatively, the catheter and lock member could be routed through a single opening or puncture. In still another embodiment, the catheter 108 could be tunneled beneath the skin to a remote location.

Figure 22A:
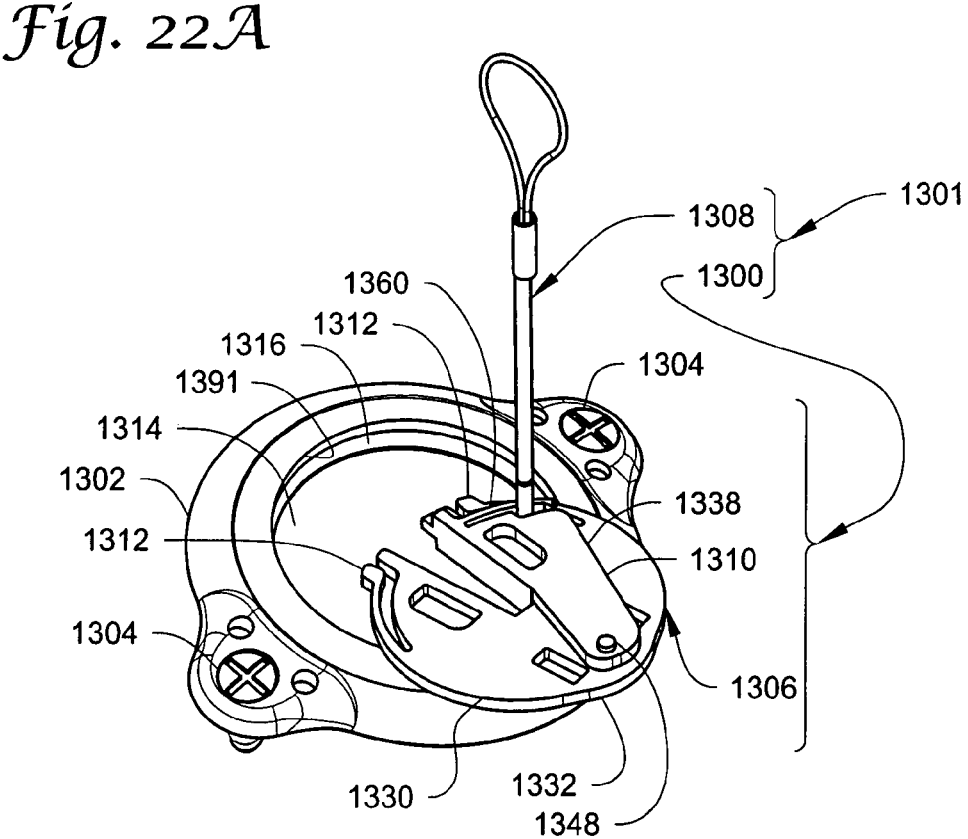
Figure 22B:
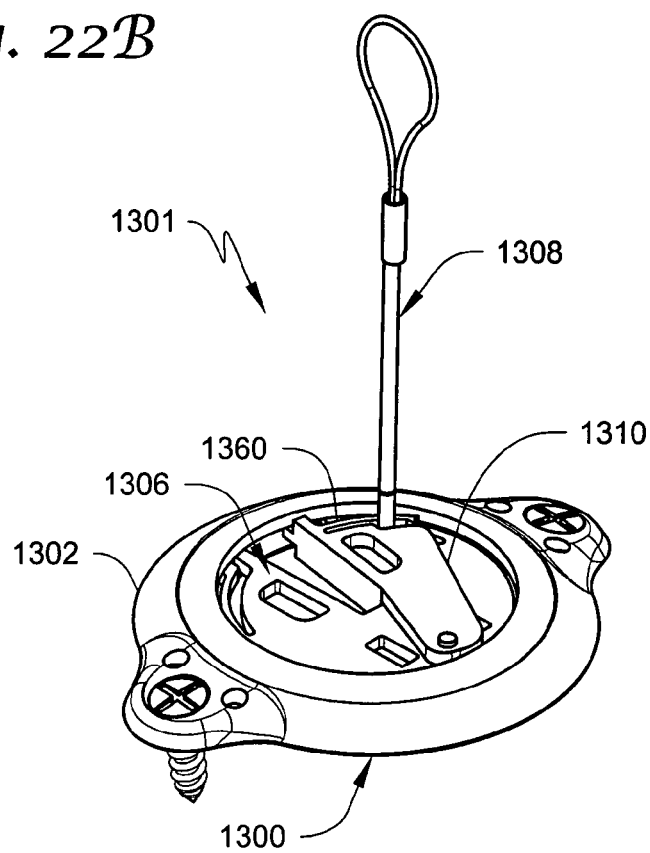

FIGS. 22A-22B illustrate an anchor assembly 1301 in accordance with another embodiment of the invention. The anchor assembly 1301 may include an anchor 1300 that is similar to the anchor 1200 described above. For example, it may include a base 1302 attachable to the skull with fasteners 1304, and a retainer 1306 having a movable, e.g., pivoting, arm 1310. The arm 1310 may include first and second plate members 1338, 1340 (the lower plate 1340 is illustrated in FIG. 24A) and locking portions 1360 (see FIG. 23) that are similar in most respects to the respective components of the anchor 1200 described above. The arm 1310 may include an integral pin 1348 formed upon an extension of the lower plate 1340 that engages a corresponding opening in a body or body portion 1330 of the retainer 1306 to permit pivotal motion. The arm 1310 is illustrated in a first or unlocked position in FIGS. 22A-22B. As with the anchor assembly 1201, the anchor assembly 1301 may further include a lock member 1308 similar in most respects to the lock member 1208 already described herein.

The base 1302 may also be similar in most respects to the base 1202. For example, it may define a central opening 1314 to receive the retainer 1306. An inner edge of base 1302 may have a circumferential groove 1391 formed therein. The groove 1391 may be similar in many respects to the groove 1291 described above. For example, it may define a ledge 1316 upon which the retainer may seat. However, unlike the groove 1291, the groove 1391 may not require teeth (e.g., teeth 1218) as the retainer 1306 utilizes a latch of a different configuration.

The latch may, in the illustrated embodiment, be formed by flexible tabs 1312 located on a peripheral edge 1332 of the body portion 1330 of the retainer 1306. The tabs 1312 may deflect to permit retainer insertion into the groove 1391, whereafter the tabs may return to their undeflected positions. As a result, the retainer 1306 may be biased against the opposite side of the base 1302 as shown in FIG. 22B. Accordingly, like the latch 1212, the tabs 112 are capable of biasing the retainer 1306 into the groove 1391 to generally secure the retainer relative to the base 1302. The spring force of the tabs 1312 is preferably sufficient to ensure little or no notable rotation between the retainer 1306 and the base 1302.

Figure 23:
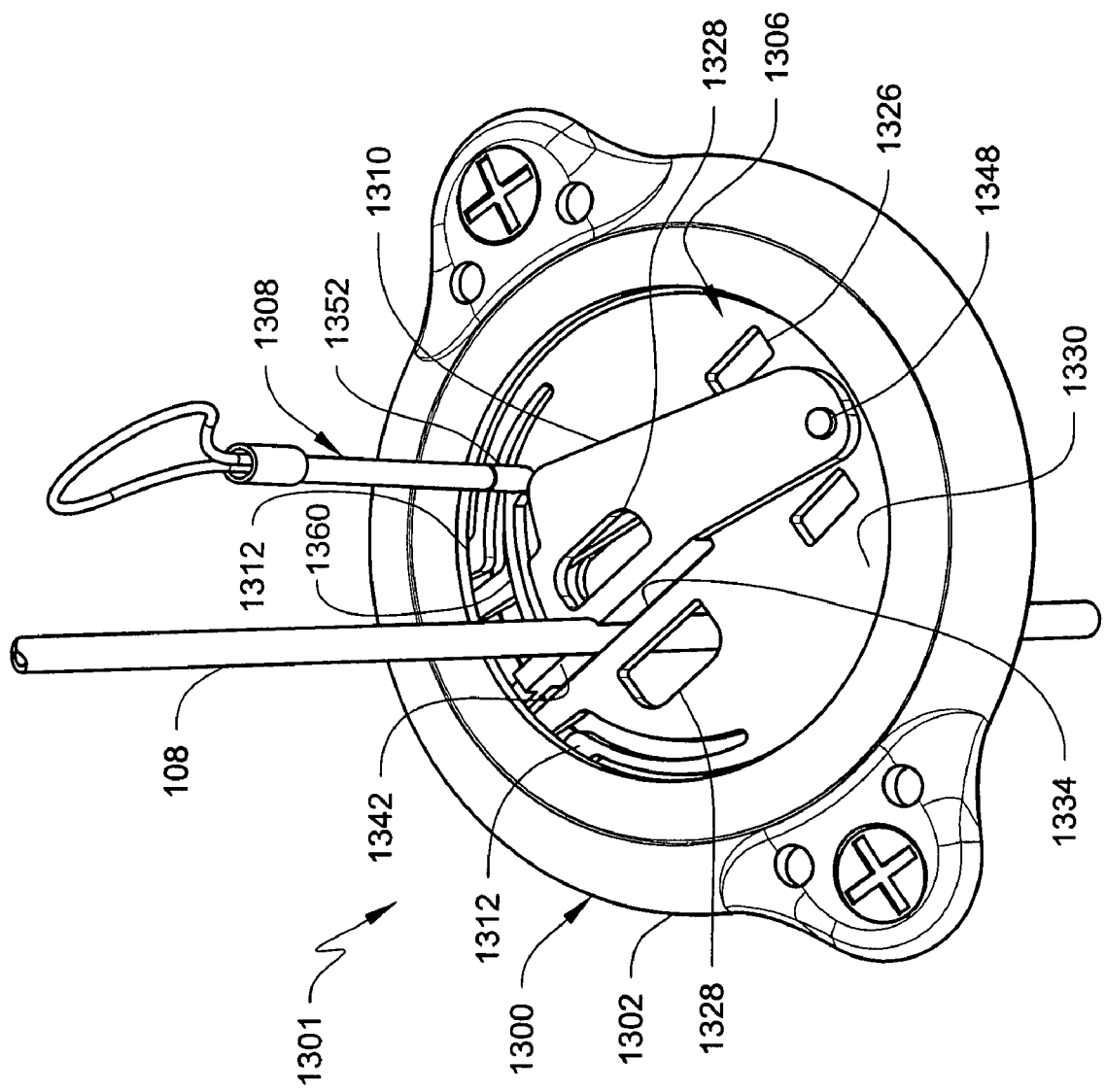
FIG. 23 is a perspective view of the anchor assembly of FIGS. 22A-22B with the retainer shown in a second or locked configuration corresponding to the arm being in a second or locked position.
Figure 24A:
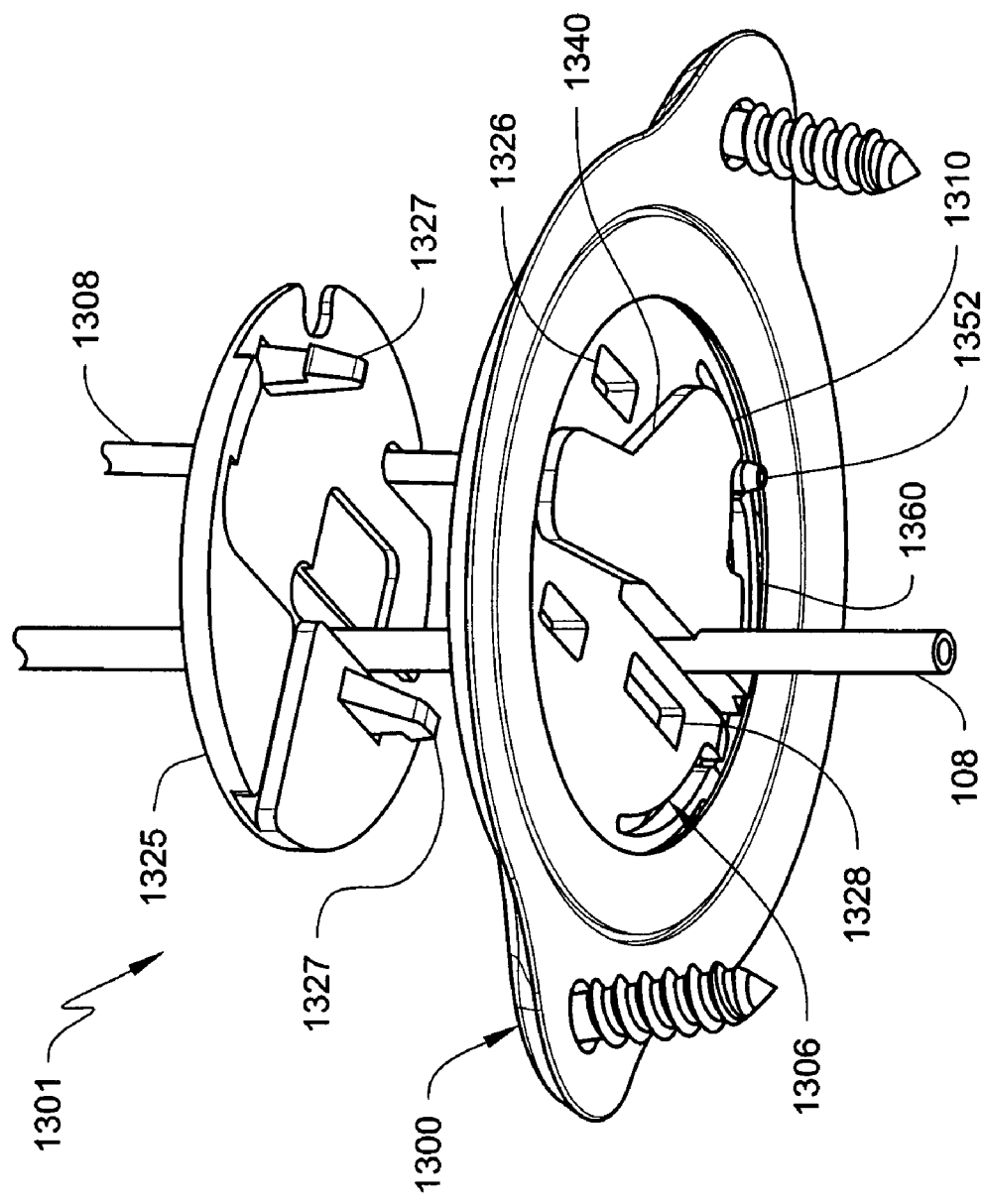

FIG. 23 is an enlarged perspective view of the anchor 1300 with the arm 1310 shown after pivotal movement to a second or locked position to secure the catheter 108. As with the retainer 1206, the body portion 1330 of the retainer 1306 may form a first retaining surface 1334 while the arm 1310 forms a second retaining surface 1342. When the arm 1310 is in the first position illustrated in FIG. 22B, the second retaining surface 1342 may be oblique to the first retaining surface 1334 as already described above with respect to the first and second retaining surfaces 1234 and 1242. However, when the arm 1310 is in the second position as shown in FIG. 23, the first and second retaining surfaces 1334 and 1342 may be generally parallel to mechanically secure the catheter 108 at most any location along a length of the slot formed by the two retaining surfaces.

As clearly shown in FIG. 23, the lock portions 1360 are substantially similar to the lock portions 1260 already described above. As a result, a surface of each lock portion 1360 may abut the lock member 1308, e.g., abut a sleeve provided at a first end 1352 of the lock member, when the arm 1310 is in the second position.

The retainer 1306 may further include openings 1326 to, for example, assist with placing the retainer within the base 1302. The body portion 1330 and arm 1310 may also include openings or slots 1328 to assist with movement of the arm to the second position via forceps or the like.

Figure 24B:
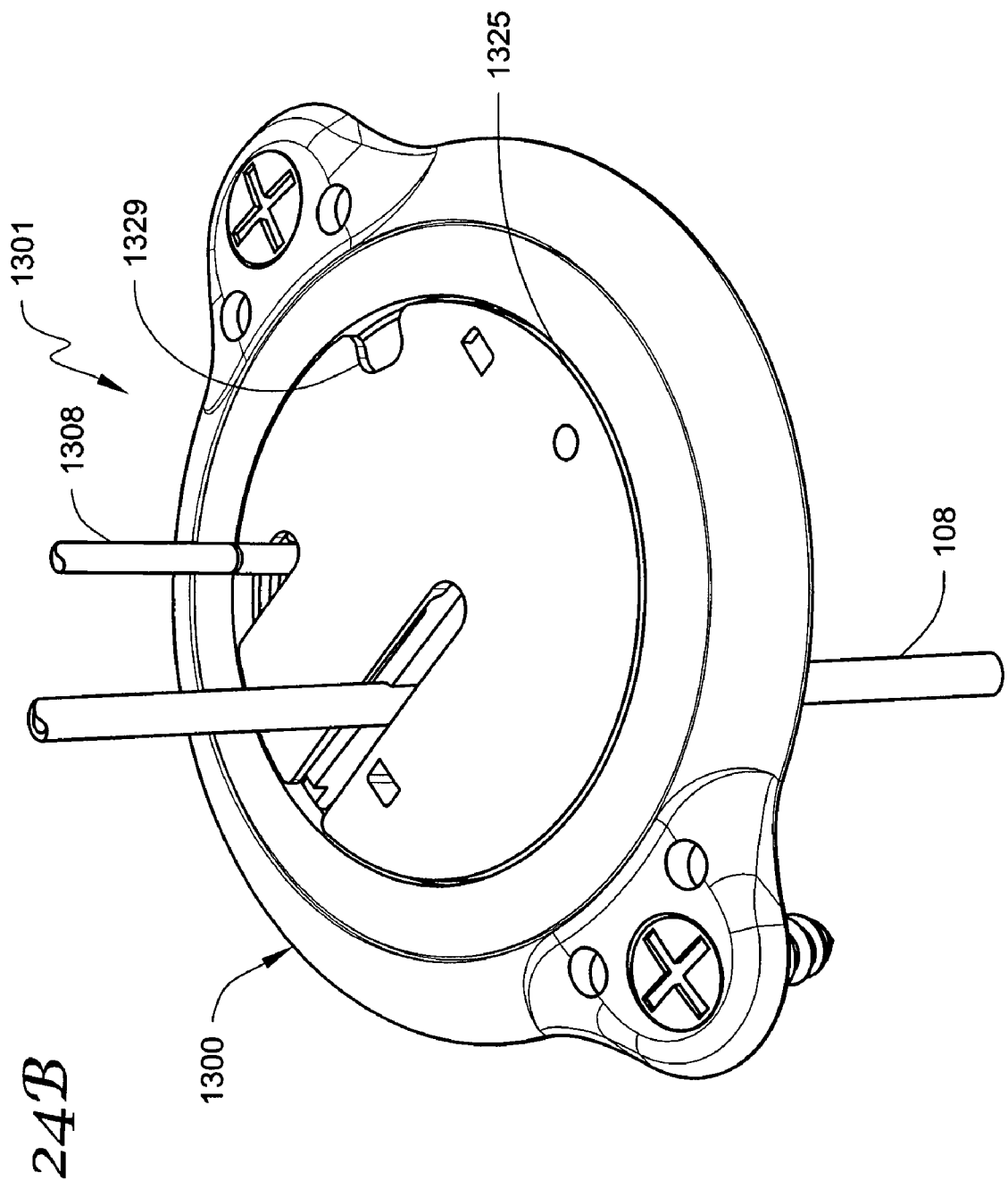

FIG. 24A is a bottom perspective view of the anchor 1300 showing an optional cover 1325 that may be placed over the retainer 1306 after the arm 1310 is moved to the second or locked position. The cover 1325 may provide a smooth outer surface (as shown in FIG. 24B) to, for example, reduce stress on local tissue (e.g., skin) and limit tissue growth into the anchor 1300. The cover 1325 may include tabs 1327 configured to securely engage one or more of the openings 1326 or slots 1328 in the body portion 1330.

FIG. 24B illustrates a top perspective view of the anchor 1300 with the cover 1325 installed. As shown, the cover may include a slot to permit side loading of the cover over the catheter 108 after catheter immobilization. A corresponding slot may be provided to accommodate the lock member 1308. To assist with removal of the cover 1325, a cutout 1329 may be provided.

FIGS. 25A-25D illustrate an anchor assembly 1401 in accordance with still yet another embodiment of the invention. The anchor assembly 1401 is similar to the anchor assemblies 1201 and 1301 described above. For example, it includes an anchor 1400 having a base 1402 attachable to the skull with fasteners 1404, and a retainer 1406 having a body or body portion 1430 and a movable, e.g., pivoting, arm 1410. Like the arm 1310, the arm 1410 may include an integral pin 1448 that engages a corresponding opening in a body portion 1430 of the retainer 1406. The arm may include a first plate member 1438 and a second plate member 1440 (see FIG. 25D) that are similar in most respects to the respective components of the anchor 1300 described above. The arm 1410 is illustrated in a first or unlocked position in FIG. 25A. The anchor assembly 1401 may also include a lock member 1408 similar to the lock members 1208 and 1308 already described herein.

The base 1402 may also be similar in most respects to the bases 1202 and 1302. For example, it may define a central opening 1414 to receive the retainer 1406. An inner edge of the base 1402 may further have a circumferential groove 1491 formed therein. The groove 1491 may be similar in many respects to the groove 1391 described above. For example, it may define a ledge 1416 upon which the retainer 1406 may seat.

The retainer 1406 may include a latch formed by flexible tabs 1412 on a peripheral edge of the body 1430 of the retainer. The tabs 1412 are substantially identical to the tabs 1312 already described above. Accordingly, like the latch 1212, the tabs 1412 are capable of biasing the retainer 1406 into the groove 1491 to generally secure the retainer to the base.

While the retainer 1406 may be secured to the base 1402 in a manner substantially identical to the retainer 1306 and base 1302 already described herein, movement of the arm 1410 from the first position (FIG. 25A) to a second or locked position (FIG. 25B) may be achieved as described below.

Figure 25A:
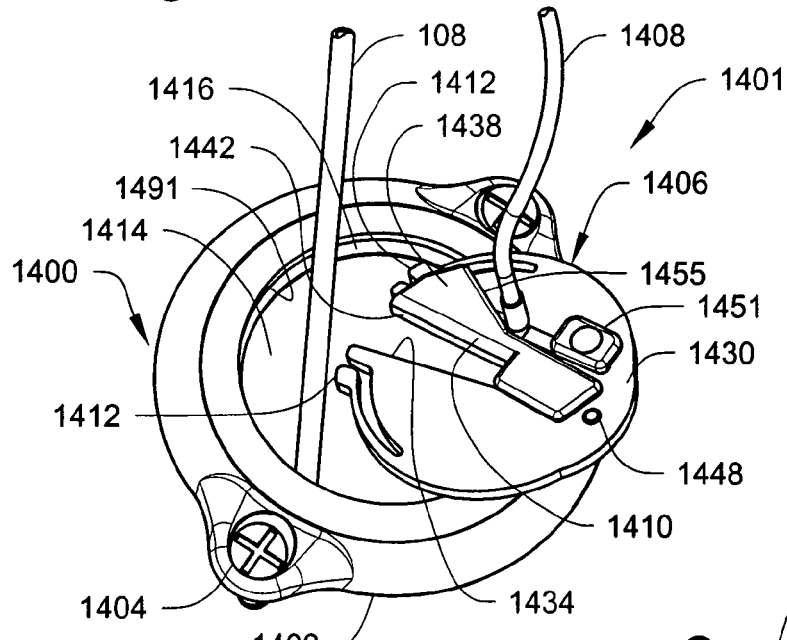

The retainer 1406 may incorporate a lock portion configured as a tab member 1451 slidable within a slot 1453 formed in the body 1430 of the retainer. When the tab member 1451 and the lock member 1408 are retracted within the slot 1453 as shown in FIG. 25A, the arm 1410 is moved to the first or unlocked position. However, once the catheter 108 is located between first and second retaining surfaces 1434 and 1442, the arm 1410 may be moved from the first position (in which the second retaining surface is oblique to the first retaining surface as already described above with respect to the surfaces 1234 and 1242) to the second or locked position illustrated in FIG. 25B. In the second position, the first and second retaining Surfaces 1434 and 1442 are generally parallel to one another to secure the catheter 108 at most any location along the slot formed by the retaining surfaces.

Figure 25B:
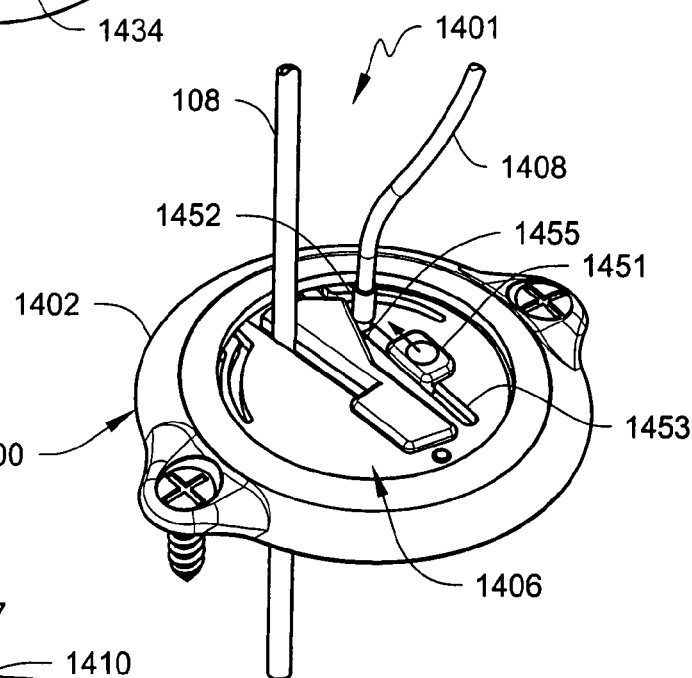
Figure 25C:
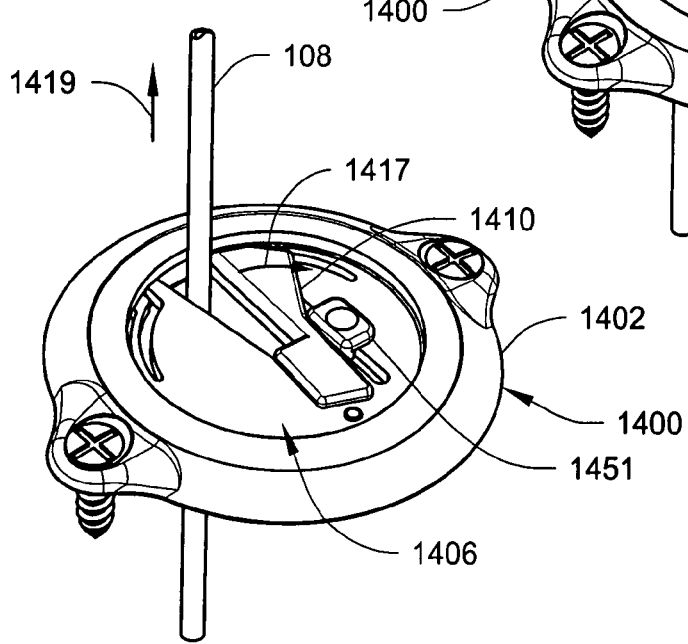
Figure 25D:
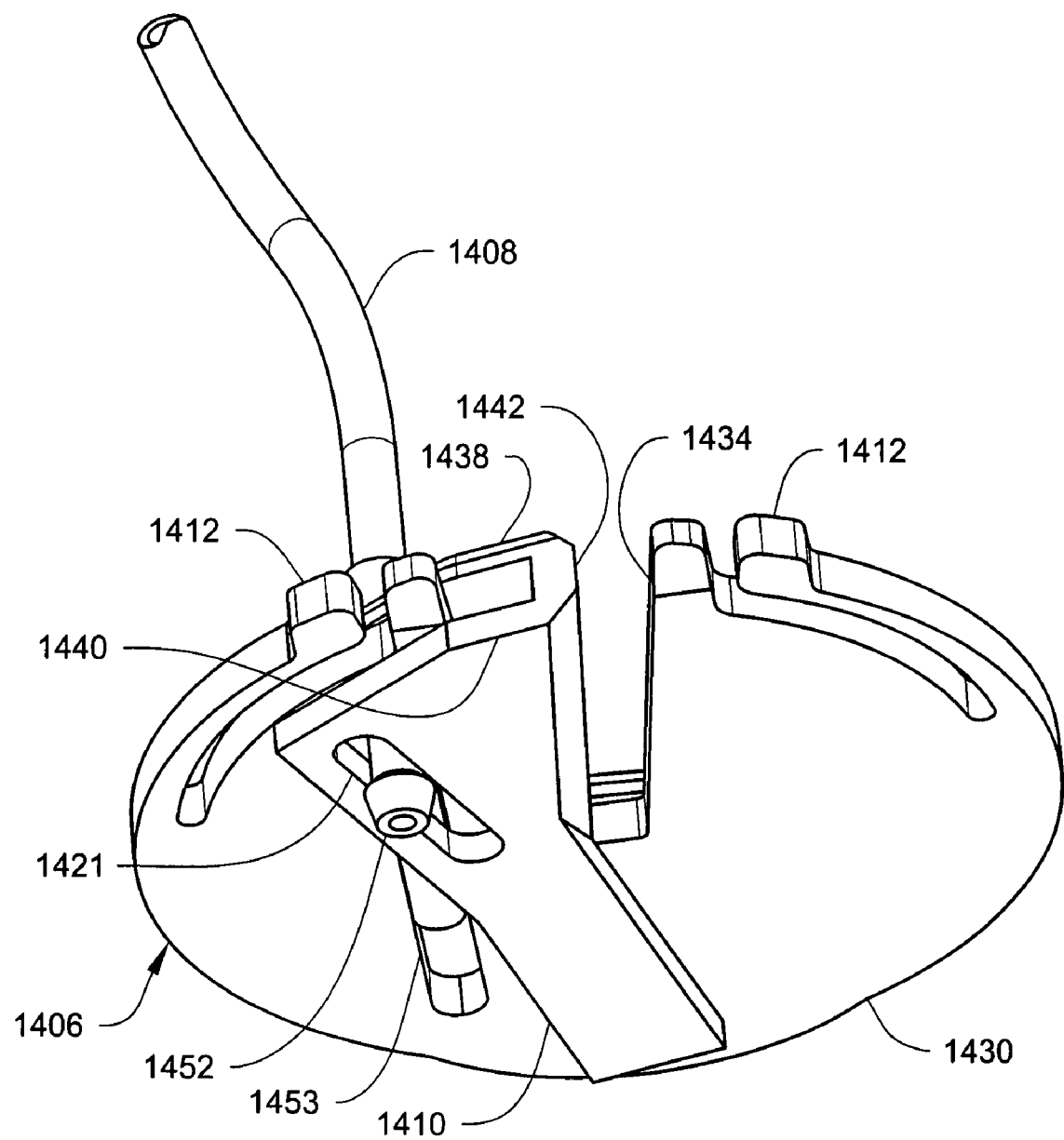

To move the arm 1410 to the second or locked position, the tab member 1451 may be slid within the slot 1453 in the direction indicated in FIG. 25B. As the tab member 1451 slides along the slot 1453, it forces a first end 1452 of the lock member 1408 into contact with a ramped edge 1455 of the arm 1410, causing the arm, e.g., the second retaining surface 1442, to move towards the first retaining surface 1434. The underside of the arm 1410 may further include a slot 1421 to accommodate movement of the lock member as shown in FIG. 25D. When the tab member 1451 reaches a location along the slot 1453 corresponding to the arm 1410, e.g., second retaining surface 1442, being in the desired locked position as shown in FIG. 25B, the tab member may engage a detent (not shown) formed in the body 1430. As a result, the arm 1410 may be secured in the second position of FIG. 25B.

The lock member 108 may be withdrawn, e.g., at therapy completion, from the anchor in a manner similar to that described above with respect to the anchor 1200 and lock member 1208. With the lock member 1408 removed from the anchor 1400, the arm 1410 is free to pivot back towards the first unlocked position as indicated in FIG. 25C by arrow 1417, thereby releasing the retention force on the catheter 108. As a result, the catheter may be withdrawn from the burr hole via the application of a traction force represented by arrow 1419.

FIG. 25D is a bottom perspective view of the anchor 1400 illustrating an exemplary configuration of the arm 1410. As illustrated in this view, the second plate member 1440 may include an extension that forms the integral pin 1448 about which the arm 1410 pivots. The second plate member 1440 may further define the slot 1421 operable to receive the first end 1452 of the lock member 1408. The slot 1421 may transform the linear movement of the tab member 1451 into pivotal movement of the arm 1410. The components of the assembly 1401, as well as of the assembly 1301, may be constructed of materials similar to those discussed elsewhere herein with respect to the corresponding components of the assembly 1201.

Anchors and anchor assemblies in accordance with embodiments of the present invention may permit anchoring of a device (such as a medical catheter or an electrical lead) relative to a portal. While such anchor assemblies may be advantageous in many applications, they may be particularly useful in medical applications wherein the anchor is subdermally located as may be the case with burr hole access procedures.

Moreover, embodiments of the present invention provide anchor assemblies and methods that permit removal of the device at therapy completion without necessitating a separate surgical procedure. For example, the anchor assembly may include a lock member that protrudes outside of the skin such that it is capable of manipulation from outside the patient's body. As a result, the lock member may be manipulated and/or removed by the clinician to release the implanted device at therapy completion without surgery. This configuration is not limiting, however, as alternative anchor assemblies may use other mechanical and non-mechanical lock configurations. For example, the anchor assembly may utilize a magnetic latch that may be manipulated by a magnet positionable outside the skin but in close proximity to the anchor. Similarly, a lock that may be released by a remote radio or ultrasonic energy transmitter could be used.

U.S. patent application Ser. No. 11/799,179 to Skakoon, filed on even date herewith, may describe various exemplary systems and methods for utilizing the components described herein.

The complete disclosures of the patents, patent applications, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An implantable catheter for delivering a therapeutic agent to a body, the catheter comprising:
    an elongate tubular core comprising a first material that comprises polyetheretherketone (PEEK) tubing, the core having a distal end and a proximal end;
    an elongate tubular tip comprising a second material, the tip also having a distal end and a proximal end, wherein the proximal end of the tip is positioned to abut or be near the distal end of the core such that a generally continuous lumen extends from the proximal end of the core to the distal end of the tip, the tip defining a cylindrical outer surface of uniform diameter extending from the distal to the proximal end of the tip, and further wherein a ratio of bending stiffness of the tip to bending stiffness of the core is about 24:1;
    an elastomeric jacket surrounding and bonded to longitudinal portions of both the tip and the core, wherein the distal end of the tip protrudes beyond a distal end of the elastomeric jacket, and wherein the elastomeric jacket has an outside diameter that is larger than the uniform outside diameter of the tip and about three or more times larger than an outside diameter of the core;
    strengthening members wound about the core and at least a portion of the tip; and
    one or more longitudinal markers located along the elastomeric jacket.

2. The catheter of claim 1, wherein the strengthening members are surrounded by, or embedded within, the elastomeric jacket.

3. The catheter of claim 1, wherein the strengthening members comprise a tubular braid located coaxially about portions of the core and the tip.

4. The catheter of claim 3, wherein the tubular braid comprises a plurality of polyethylene terepthalate (PET) fibers.

5. The catheter of claim 1, further comprising one or more longitudinal members extending along portions of one or both of the core and the tip.

6. The catheter of claim 1, wherein the strengthening members terminate a distance short of the distal end of the elastomeric jacket.

7. The catheter of claim 1, wherein the strengthening members comprise a plurality of first braided members helically wound about a longitudinal portion of the catheter in a first direction, and a plurality of second braided members helically wound about the longitudinal portion of the catheter in a second, opposite direction.

8. The catheter of claim 1, wherein the tip comprises glass tubing.

9. The catheter of claim 1, wherein the tip comprises stainless steel tubing.

10. The catheter of claim 1, wherein the elastomeric jacket comprises a material selected from the group consisting of silicone and polyurethane.

* * * * *